(12) United States Patent
Piater et al.

(10) Patent No.: US 11,130,818 B2
(45) Date of Patent: Sep. 28, 2021

(54) TRANSGLUTAMINE TAG FOR EFFICIENT SITE-SPECIFIC BIOCONJUGATION

(71) Applicant: Merck Patent GmbH, Darmstadt (DE)

(72) Inventors: Birgit Piater, Darmstadt (DE); Ulrich Betz, Reinheim (DE); Harald Kolmar, Muehltal (DE); Vanessa Siegmund, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 358 days.

(21) Appl. No.: 15/750,725

(22) PCT Filed: Aug. 4, 2016

(86) PCT No.: PCT/EP2016/001344
§ 371 (c)(1),
(2) Date: Feb. 6, 2018

(87) PCT Pub. No.: WO2017/025179
PCT Pub. Date: Feb. 16, 2017

(65) Prior Publication Data
US 2019/0194344 A1 Jun. 27, 2019

(30) Foreign Application Priority Data
Aug. 7, 2015 (EP) .................................... 15180278

(51) Int. Cl.
*C07K 16/30* (2006.01)
*C07K 16/00* (2006.01)
(Continued)

(52) U.S. Cl.
CPC .......... *C07K 16/30* (2013.01); *A61K 47/6849* (2017.08); *A61P 35/00* (2018.01);
(Continued)

(58) Field of Classification Search
None
See application file for complete search history.

(56) References Cited

U.S. PATENT DOCUMENTS

| 4,816,567 A | 3/1989 | Cabilly et al. |
|---|---|---|
| 6,004,528 A | 12/1999 | Bergstein |

FOREIGN PATENT DOCUMENTS

| WO | WO 94/04678 A1 | 3/1994 |
|---|---|---|
| WO | WO 02/094852 A2 | 11/2002 |

(Continued)

OTHER PUBLICATIONS

Rachel M et al., Biomolecules 2013, vol. 3, No. 4, 2013, pp. 870-888 (Year: 2013).*

(Continued)

*Primary Examiner* — Karl J Puttlitz
(74) *Attorney, Agent, or Firm* — Womble Bond Dickinson (US) LLP

(57) ABSTRACT

The present invention provides novel peptide sequences for use in microbial transgluatminase-mediated, in particular mTG2-mediated bioconjugations, in particular for the manufacture of antibody-drug-conjugates. Further disclosed are bioconjugation methods employing mTG2 and the novel peptide sequence motifs of the invention. The present invention further provides proteins comprising the novel sequence motifs of the invention as well as polynucleotides encoding the same.

13 Claims, 16 Drawing Sheets

Specification includes a Sequence Listing.

(51) Int. Cl.
  C07K 16/28 (2006.01)
  A61K 47/68 (2017.01)
  A61P 35/00 (2006.01)
(52) U.S. Cl.
  CPC .......... C07K 16/00 (2013.01); C07K 16/2863 (2013.01); C07K 2317/24 (2013.01); C07K 2317/54 (2013.01); C07K 2317/569 (2013.01); C07K 2317/622 (2013.01)

(56) References Cited

FOREIGN PATENT DOCUMENTS

| WO | WO 2012/059882 A2 | 5/2012 | |
|----|-------------------|--------|---|
| WO | WO 2013/092983 A2 | 6/2013 | |
| WO | WO 2015/097267 A1 | 7/2015 | |
| WO | 2017106643 | * | 7/2017 |

OTHER PUBLICATIONS

Yang et al., Genome Announcements Mar.-Apr. 2013, vol. 1, No. 2, Mar. 2013 (Mar. 2013), p. eOOI4313 (Year: 2013).*
Database UniProt [Online], May 1, 2013 (May 1, 2013), Database accession No. M381Z5 (Year: 2013).*
Sarafeddinov et al., Bioscience, Biotechnology, and Biochemistry May 2009, vol. 73, No. 5, May 2009 (May 2009), pp. 993-999 (Year: 2009).*
Database UniProt [Online], Apr. 14, 2009 (Apr. 14, 2009), Database accession No. DAIP_STRMB (Year: 2009).*
Abuchowski, A., et al., "Alteration Immunological Properties of Bovine Serum Albumin by Covalent Attachment of Polyethylene Glycol," *The Journal of Biological Chemistry*, 1977, vol. 252(11), pp. 3578-3581.
Alivisatos, A. P., "Perspectives on the Physical Chemistry of Semiconductor Nanocrystals," *J. Phys. Chem.*, 1996, vol. 100, pp. 13226-13239.
Alivisatos, A. P., "Semiconductor Clusters, Nanocrystals, and Quantum Dots," *Science*, 1996, vol. 271(5251), pp. 933-937.
Ando, H., et al., "Purification and Characteristics of a Novel Transglutaminase Derived from Microorganisms," *Agric. Biol. Chem.*, 1989, vol. 53(10), pp. 2613-2617.
Binz, H., et al., "Engineering novel binding proteins from nonimmunoglobulin domains," *Nature Biotechnology*, 2005, vol. 23(10), pp. 1257-1268.
Bobek, L., et al., "Expression of Human Salivary Histatin and Cystatin/Histatin Chimeric cDNAs in *Escherichia coli*," *Critical Reviews in Oral Biology and Medicine*, 1993, vol. 4(3/4), pp. 581-590.
Clackson, T., et al., "Making antibody fragments using phage display libraries," *Nature*, 1991, vol. 352, pp. 624-628.
De Kok, S., et al., "Rapid and Reliable DNA Assembly via Ligase Cycling Reaction," *ACS Synthetic Biology*, 2014, vol. 3, pp. 97-106.
Desmyter, A., et al., "Camelid nanobodies: killing two birds with one stone," *Current Opinion in Structural Biology*, 2015, vol. 32, pp. 1-8.
Elgersma, R., et al., "Design, Synthesis, and Evaluation of Linker-Duocarmycin Payloads: Toward Selection of HER2-Targeting Antibody-Drug Conjugate SYD985," *Mol. Pharmaceutics*, 2015, vol. 12, pp. 1813-1835.
Fontana, A., et al., "Site-specific modification of PEGylation of pharmaceutical proteins mediated by transglutaminase," *Advanced Drug Delivery Reviews*, 2008, vol. 60, pp. 13-28.
Gerber, U., et al., "A rapid and simple method for the purification of transglutaminase from *Streptoverticilium mobaraense*," *Biochem. J.*, 1994, vol. 299, pp. 825-829.
Gibson, D., et al., "One-step assembly in yeast of 25 overlapping DNA fragments to form a complete synthetic *Mycoplasma genitalium* genome," *PNAS*, 2008, vol. 105(51), pp. 20404-20409.
Gibson, D., et al., "Enzymatic assembly of DNA molecules up to several hundred kilobases," *Nature Methods*, 2009, vol. 6(5), pp. 343-345.
Griffin, M., et al., "Transglutaminases: Nature's biological glues," *Biochem. J.*, 2002, vol. 368, pp. 377-396.
Hamblett, K., et al., "Effects of Drug Loading on the Antitumor Activity of a Monoclonal Antibody Drug Conujugate," *Clinical Cancer Research*, 2004, vol. 10, pp. 7063-7070.
Hamers-Casterman, C., et al., "Naturally occurring antibodies devoid of light chains," *Nature*, 1993, vol. 363, pp. 446-448.
*Handbook of Therapeutic Antibodies*, 2nd edition, edited by S. Dübel and J.M. Reichert, John Wiley & Sons, 2014, pp. 369.
Harmsen, M., et anon., "Properties, production, and applications of camelid single-domain antibodiy fragments," *Appl Microbial Biotechnol*, 2007, vol. 77, pp. 13-22.
Hemsley, A., et al., "A simple method for site-directed mutagenesis using the polymerase chain reaction," *Nucleic Acids Research*, 1989, vol. 17(16), pp. 6545-6551.
Jeger, S., et al., "Site-Specific and Stoichiometric Modification of Antibodies by Bacterial Transglutaminase," *Angew. Chem. Int. Ed.*, 2010, vol. 49, pp. 9995-9997.
Kirchhoff, et anon., "A PCR-Derived Library of Random Point Mutations within the V3 Region of Simian Immunodeficiency Virus," *PCR Methods and Applications*, 1993, vol. 2(4), pp. 301-304.
Klimatcheva, E., et al., "Lentiviral Vectors and Gene Therapy," *Frontiers in Bioscience*, 1999, vol. 4, pp. d481-d496.
Köhler, G., et anon., "Continuous cultures of fused cells secreting antibody of predefined specificity," *Nature*, 1985, vol. 256, pp. 495-497.
Kong, D., et al., "Parallel gene synthesis in a microfluidic device," *Nucleic Acids Research*, 2007, vol. 35(8), pp. 461 (9 pages).
Kornberger, P., et anon., "Sortase-catalyzed in vitro functionalization of a HER2-specific recombinant Fab for tumor targeting of the plant cytotoxin gelonin," *mAbs*, 2014, vol. 6(2), pp. 354-366.
Lin, C., et anon., Transglutaminase-Catalyzed Site-Specific Conjugation of Small-Molecule Probes to Proteins in Vitro and on the Surface of Living Cells, *J. Am. Chem. Soc.*, 2006, vol. 128, pp. 4542-4543.
Liu, F., et al., "Irreversible Sortase A-Mediated Litigation Driven by Diketopiperazine Formation," *The Journal of Organic Chemistry*, 2014, vol. 79, pp. 487-492.
Mansur, H., et al., "Biomolecule-quantum dot systems for bioconjugation applications," *Colloids and Surfaces B: Biointerfaces*, 2011, vol. 84, pp. 360-368.
Marks, J., et al., "By-passing Immunization Human Antibodies from V-gene Libraries Displayed on Phage," *J. Mol. Biol.*, 1991, vol. 22, pp. 581-597.
Marx, C., et al., Purification and activation of a recombinant histidine-tagged pro-transglutaminase after soluble expression in *Escherichia coli* and partial characterization of the active enzyme, *Enzyme and Microbial Technology*, 2008, vol. 42, pp. 568-575.
Marx, C., et al., "Random mutagenesis of a recombinant microbial transglutaminase for the generation of thermostable and heat-sensitive variants," *Journal of Biotechnology*, 2008, vol. 136, pp. 156-162.
Mauro, V., et anon., "A critical analysis of codon optimization in human therapeutics," *Trends Mol. Med.*, 2014, vol. 20(11), pp. 604-613.
Morgenstern, J., et anon., "A series of mammalian expression vectors and characterisation of their expression of a reporter gene in stably and transiently transfected cells," *Nucleic Acids Research*, 1990, vol. 18(4), p. 1068.
Ohtsuka, T., et al., "Comparision of Substrate Specificities of Transglutaminases Using Synthetic Peptides as Acyl donors," *Biosci. Biotechnol. Biochem.*, 2000, vol. 64(12), pp. 2608-2613.
Perez, H., et al., "Antibody-drug conjugates: current status and future directions," *Drug Discovery Today*, 2014, vol. 19(7), pp. 869-881.
Popp, M., et anon., "Making and Breaking Peptide Bonds: Protein Engineering Using Sortase," *Angew. Chem. Int. Ed.*, 2011, vol. 50, pp. 5024-5032.

(56) References Cited

OTHER PUBLICATIONS

Rachel, N., et anon., "Biotechnological Applications of Transglutaminases," *Biomolecules*, 2013, vol. 3, pp. 870-888.

Robinson, B., et al., "[³H]Biotin-labeled Proteins in Cultured Human Skin Fibroblastsfrom Patients with Pyruvate Carboxylase Deficiency," *The Journal of Biological Chemistry*, 1983, vol. 258(10), pp. 6660-6664.

Sanderson, R., et al., "In vivo Drug-Linker Stability of anAnti-CD30 Dipeptide-Linked Auristatin Immunoconjugate," *Clinical Cancer Research*, 2005, vol. 11, pp. 843-852.

Sarafeddinov, A., et al., "A Novel Transglutaminase Substrate from *Streptomyces mobaraensis* Triggers Autolysis of Neutral Metalloproteases," *Biosci. Biotechnol. Biochem.*, 2009, vol. 73(5), pp. 993-999.

Siegmund,V., et al., "Locked by Design: A Conformationally Constrained Transglutaminase Tag Enables Efficient Site-Specific Conjugation," *Angew. Chem. Int. Ed.*, 2015, vol. 54, pp. 13420-13424.

Skrlec, K., et al., "Non-immunoglobulin scaffolds: a focus on their targets," *Trends in Biotechnology*, 2015, vol. 33(7), pp. 408-418.

Sommer, C., et al., "Model based optimization of the fed-batch production of a highly active transglutaminase variant in *Escherichia coli*," *Protein Expression and Purification*, 2011,vol. 77, pp. 9-19.

Song, F., et anon., "Principles of conjugating quantum dots to proteins via carbodiimide chemistry," *Nanotechnology*, 2011, vol. 22, pp. 494006 (7 pages).

Sugimura, Y., et al., "Identification of preferred substrate sequences of microbial transglutaminase from *Streptomyces mobaraensis* using a phage-displayed peptide library," *Archives or Biochemisttry and Biophysics*, 2008, vol. 477, pp. 379-383.

Takaoka, Y., et al., "Protein Organic Chemistry and Applications for Labeling and Engineering in Live-Cell Systems," *Angew. Chem. Int. Ed.*, 2013, vol. 52, pp. 4088-4106.

Tian, J., et al., "Accurate multiplex gene synthesis from programmable DNA microchips," *Nature*, 2004,vol. 432, pp. 1050-1054.

Watkins, B., et al., "A Rapid Method for Site-Specific Mutagenesis Using Larger Plasmids as Templates," *Biotechniques*, 1993, vol. 15(4), pp. 700-704.

Weller, Horst, "Colloidal Semiconductor Q-Particles: Chemistry in the Transition Region Between Solid State and Molecules," *Angew. Chem. Int. Ed. Engl.*, 1993, vol. 32, pp. 41-53.

Wilm, M., et al., "Femtomole sequencing of proteins from polyacrylamide gels by nano-electrospray mass spectometry," *Nature*, 1996, vol. 379, pp. 466-469.

Yang, H., et al., "Whole-Genome Shotgun Assembly and Analysis of the Genome of *Streptomyces mobaraensis* DSM 40847, a Strain for Industrial Production of Microbial Transglutaminase," *Genome Announcements*, 2013, vol. 1(2), pp. e00143-e001413 (2 pages).

Yilmaz, Ö., et al., "SLAM family markers are conserved among hematopoietic stem cells from old and reconsituted mice and markedly increase their purity," *Blood*, 2006,vol. 107(3), pp. 924-930.

Zhang, Y, et al., "SLiCE: a novel bacterial cell extract-based DNA cloning method," *Nucleic Acids Research*, 2012, vol. 40(8),pp. e55, (10 pages).

Zheng, L., et al., "An efficient one-step site-directed and site-saturation mutagenesis protocol," *Nucleic Acids Research*, 2004,vol. 32(14), pp. e115 (5 pages).

Zielonka, S., et al., "Structural insights and biomedical potential of IgNAR scaffolds from sharks," *mAbs*, 2015, vol. 7(1), pp. 15-25.

\* cited by examiner a)
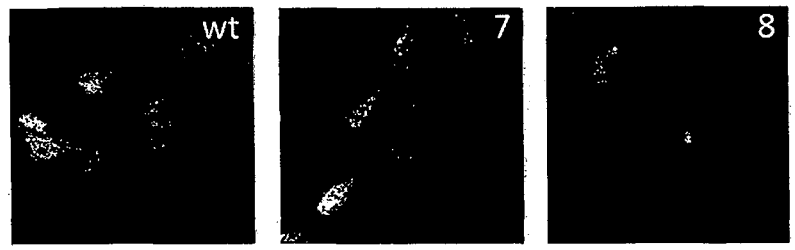
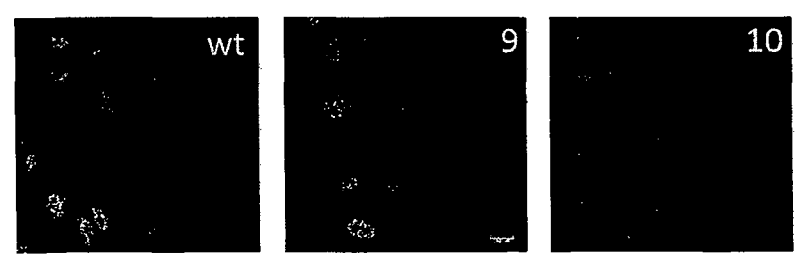
b)
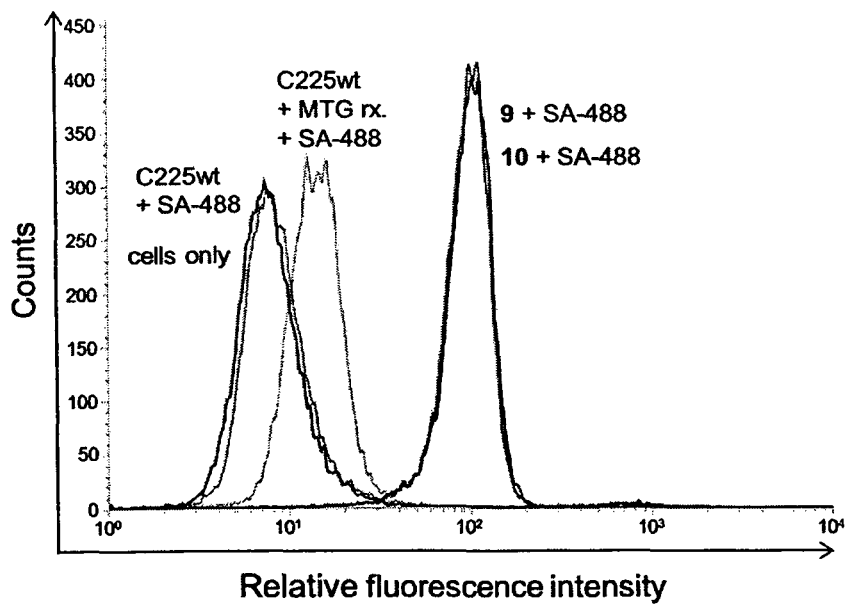
Figure 3

QVQLKQSGPGLVQPSGSLSITCTVSGFSLTNYGVHWVRQSPGKGLEWLGVIWSGGNTDYN 60
                                                        ―――――――――
                                                          magenta TPFTSRLSINKDNSKSQVFFKMNSLQSNDTAIYYCARALTYYDYEFAYWGQGTLVTVSAA 120
―――――――――――――――――――――――
        2569.22                        ―――――
                                        754.40

STKGPSVFPLAPSSKSTSGGTAALGCLVKDYFPEPVTSWNSGALTSGVHTFPAVLQSSG 180
                    ―――――
                    1185.64

LYSLSSVVTVPSSSLGTQTYICNVNHKPSNTKVDKRVEPKSPKSCDKTHTCPPCPAPELL 240
                                              ――――
                                              627.37  - - - - - cyan GGPSVFLFPPKPKDTLMSRTPEVTCVVVDVSHEDPEVKFNWYVDGVEVHNAKTKPREEQ 300
―――――――――――――      ―――――――――――――
 2727.39  3159.55    834.43              2079.99            1676.79

YNSTYRVVSVLTVLHQDWLNGKEYKCKVSNKALPAPIEKTISKAKGQPREPQVYTLPPSR 360
                       ――――――――――                          ―――
                         2227.20                          655.38  1285.67

DELTKNQVSLTCLVKGFYPSDIAVEWESNGQPENNYKTTPPVLDSDGSFFLYSKLTVDKS 420
         ―――――                     ―――――                ―――
         1102.59                   2543.12   2544.42  1904.12   1872.91

RWQQGNVFSCSVMHEALHNHYTQKSLSLSPGGENTYFQAYGNTE 464
―――――――――――――――                        ――――
 1871.96       2742.23                 2133.95

Figure 10A

Residue coverage: 56% [261 of 464]
Peptide hits: 14 [12]  Modified: 6 [6]  Not identified: 8

Peptides identified without modifications:
```
 input    found    dev.   mc  from-to  sequence
 628,400 / 627,370  -0,022  1  216-220  RVEPK
 656,400 / 655,377  -0,016  1  344-349  AKGQPR          Missed cleavage
 755,500 / 754,401  -0,091  0   76- 81  SQVFFK
 835,500 / 834,427  -0,066  0  254-260  DTLMISR         metOx missing
1186,700 / 1185,639 -0,053  0  124-135  GPSVFPLAPSSK
1286,700 / 1285,667 -0,026  0  350-360  EPQVYTLPPSR
1677,900 / 1676,795 -0,098  0  280-293  FNWYVDGVEVHNAK
1874,000 / 1872,915 -0,078  0  398-414  TTPPVLDSDGSFFLYSK
1874,000 / 1871,963 -1,030  1  350-365  EPQVYTLPPSRDELTK
1905,000 / 1904,121  0,128  3  332-349  ALPAPIEKTISKAKGQPR Missed cleavage
2229,300 / 2227,200 -1,093  1  307-325  VVSVLTVLHQDWLNGKEYK
2545,200 / 2544,422  0,230  5  323-345  EYKCKVSNKALPAPIEKTISKAK Missed cleavage
2545,200 / 2543,124 -1,069  0  376-397  GFYPSDIAVEWESNGQPENNYK
2570,290 / 2569,224 -0,059  0   44- 66  GLEWLGVIWSGGNTDYNTPFTSR
```

Peptides identified with modifications:
```
1161,700 / 1102,593 -0,070  0  366-375 CAM   NQVSLTCLVK
2139,100 / 2079,991 -0,073  0  261-279 CAM   TPEVTCVVVDVSHEDPEVK
2446,200 / 2133,949 -0,077 -1  445-464 MBC   SLSLSPGGENTYFQAYGNTE
2801,300 / 2742,231 -0,033  0  422-444 CAM   WQQGNVFSCSVMHEALHNHYTQK
2844,500 / 2727,392 -0,042  0  228-253 CAM   THTCPPCPAPEL....GPSVFLFPPKPK
3334,700 / 3159,547 -0,058  1  224-253 CAM   SCDKTHTCPPCP....GPSVFLFPPKPK
```

Mass values not identified:
```
 674,50   777,40   804,30   860,50   876,50
1208,70  3116,40  3278,50
```

**Mass list checked for modifications [3*]:**
    CAM (58,029 Da) [C]
    MBC (311,167 Da) [Q]

Figure 10 B

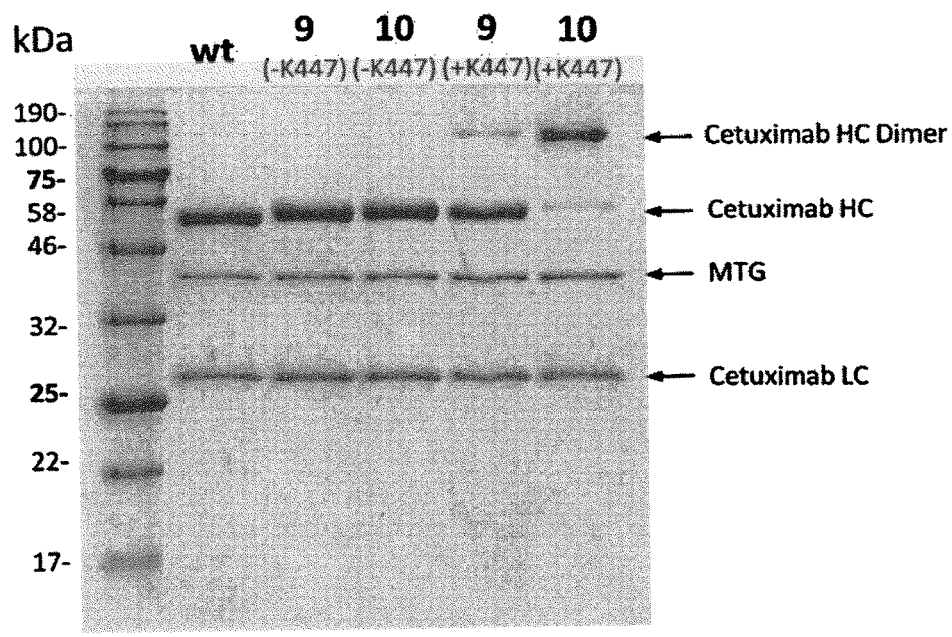

Figure 11

| Sample | 1 | 2 | 3 | Mean | Std. dev. | cThiole [mM] | cProtein [mM] | cThiole/cProtein | Thiols/Protein theoretical |
|---|---|---|---|---|---|---|---|---|---|
| Lysozyme (red.) | 0.428 | 0.493 | 0.463 | 0.461 | 0.033 | 0.497 | 0.067 | 7.459 | 8 |
| Lysozyme | 0.110 | 0.095 | 0.105 | 0.104 | 0.008 | 0.044 | 0.062 | 0.714 | 8 |
| Cetuximab wt | 0.102 | 0.088 | 0.122 | 0.104 | 0.017 | 0.045 | 0.013 | 3.334 | 32 |
| 7 | 0.085 | 0.089 | 0.093 | 0.089 | 0.004 | 0.026 | 0.016 | 1.641 | 36 |
| 8 | 0.107 | 0.091 | 0.106 | 0.102 | 0.009 | 0.042 | 0.020 | 2.131 | 32 |

Conjugation of cetuximab with GGG-substrates by microbial transglutaminase (MTG)
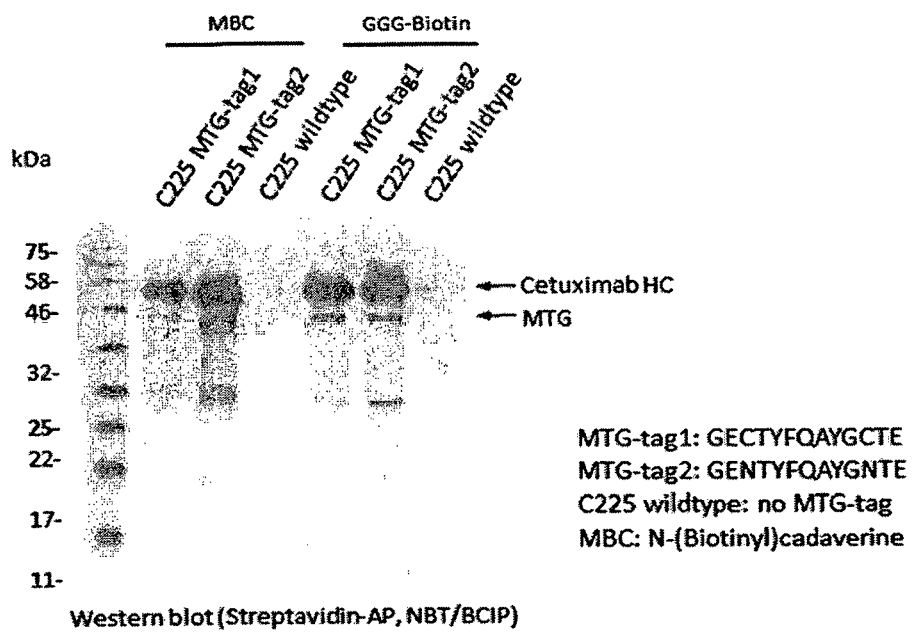
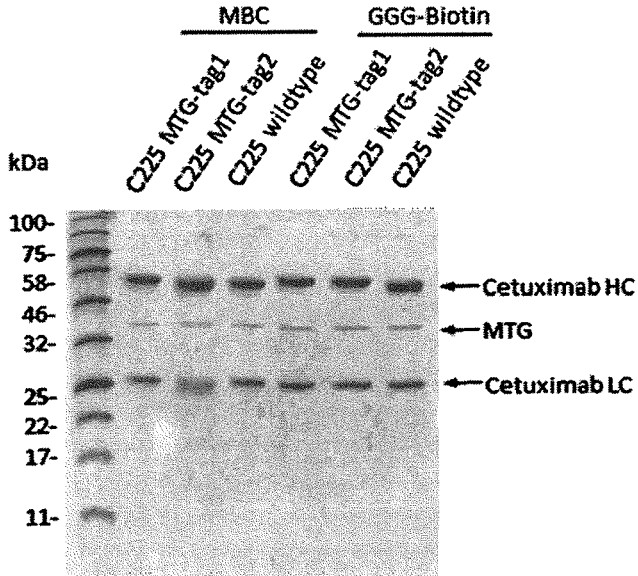
MTG-tag1: GECTYFQAYGCTE
MTG-tag2: GENTYFQAYGNTE
C225 wildtype: no MTG-tag
MBC: N-(Biotinyl)cadaverine
Figure 14 A, B

1
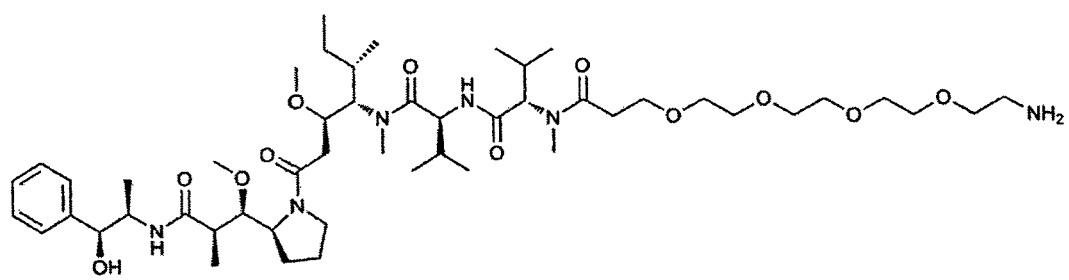
2
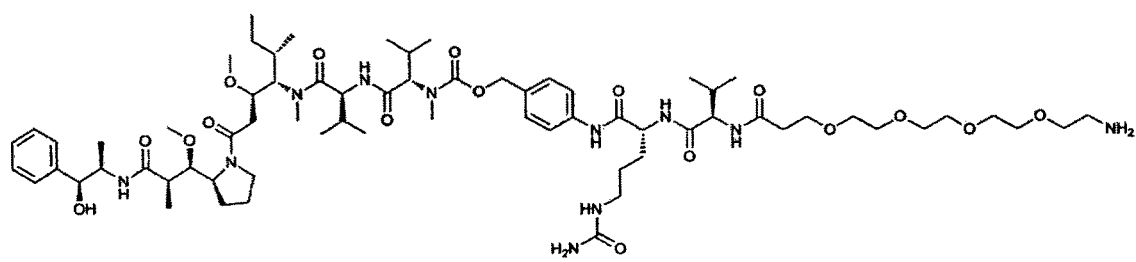
3
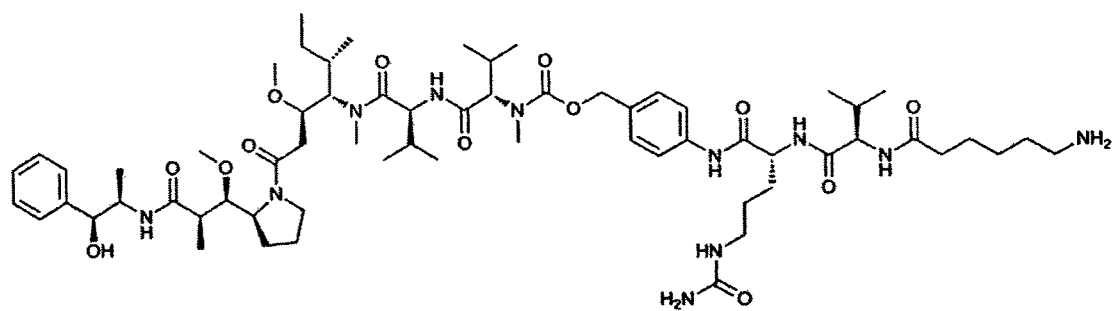
4
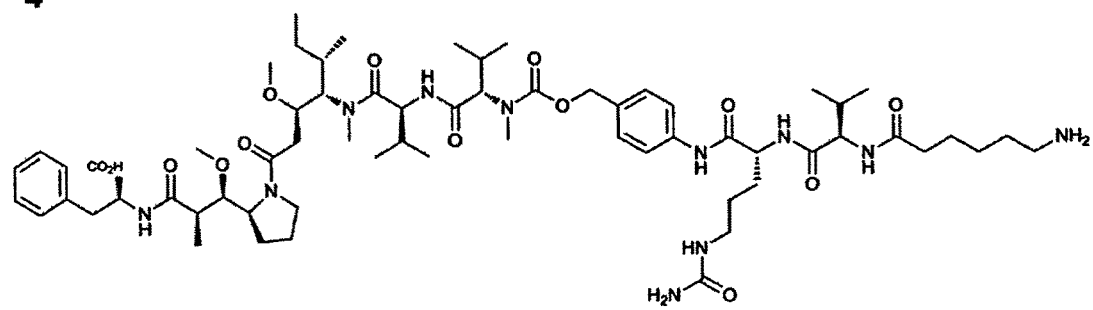
Figure 15

SEQUENCE LISTING

```
<160> NUMBER OF SEQ ID NOS: 303

<210> SEQ ID NO 1
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 1

Thr Tyr Phe Gln Ala Tyr Gly
1               5

<210> SEQ ID NO 2
<211> LENGTH: 13
<212> TYPE: PRT
<213> ORGANISM: Artificial Sequence
<220> FEATURE:
<223> OTHER INFORMATION: artificial amino acid sequence
<220> FEATURE:
<221> NAME/KEY: X1
<222> LOCATION: (1)..(1)
<223> OTHER INFORMATION: x1 is a hydrophobic amino acid (A, I, L, M, F,
      W, Y, V)
<220> FEATURE:
<221> NAME/KEY: X2
<222> LOCATION: (2)..(2)
<223> OTHER INFORMATION: X2 is a negatively charged amino acid (D, E)
<220> FEATURE:
<221> NAME/KEY: X3
<222> LOCATION: (3)..(3)
<223> OTHER INFORMATION: X3 is C or N
<220> FEATURE:
<221> NAME/KEY: X4
<222> LOCATION: (11)..(11)
<223> OTHER INFORMATION: X4 is C or N
<220> FEATURE:
<221> NAME/KEY: X5
<222> LOCATION: (12)..(12)
<223> OTHER INFORMATION: X5 is an amino acid with a polar, uncharged
      side chains (S, T, N, Q)
```

-continued

```
<220> FEATURE:
<221> NAME/KEY: X6
<222> LOCATION: (13)..(13)
<223> OTHER INFORMATION: X6 is a negatively charged amino acid (D, E)

<400> SEQUENCE: 2

Xaa Xaa Xaa Thr Tyr Phe Gln Ala Tyr Gly Xaa Xaa Xaa
1               5                   10

<210> SEQ ID NO 3
<211> LENGTH: 13
<212> TYPE: PRT
<213> ORGANISM: Artificial Sequence
<220> FEATURE:
<223> OTHER INFORMATION: artificial amino acid sequence
<220> FEATURE:
<221> NAME/KEY: X1
<222> LOCATION: (1)..(1)
<223> OTHER INFORMATION: X1 is a hydrophobic amino acid (A, I, L, M, F,
      W, Y, V)
<220> FEATURE:
<221> NAME/KEY: X2
<222> LOCATION: (2)..(2)
<223> OTHER INFORMATION: X2 is a negatively charged amino acid (D, E)
<220> FEATURE:
<221> NAME/KEY: X5
<222> LOCATION: (12)..(12)
<223> OTHER INFORMATION: X5 is an amino acid with a polar, uncharged
      side chains (S, T, N, Q)
<220> FEATURE:
<221> NAME/KEY: X6
<222> LOCATION: (13)..(13)
<223> OTHER INFORMATION: X6 is a negatively charged amino acid (D, E)

<400> SEQUENCE: 3

Xaa Xaa Cys Thr Tyr Phe Gln Ala Tyr Gly Asn Xaa Xaa
1               5                   10

<210> SEQ ID NO 4
<211> LENGTH: 13
<212> TYPE: PRT
<213> ORGANISM: Artificial Sequence
<220> FEATURE:
<223> OTHER INFORMATION: artifical amino acid sequence
<220> FEATURE:
<221> NAME/KEY: X1
<222> LOCATION: (1)..(1)
<223> OTHER INFORMATION: x1 is a hydrophobic amino acid (A, I, L, M, F,
      W, Y, V)
<220> FEATURE:
<221> NAME/KEY: X2
<222> LOCATION: (2)..(2)
<223> OTHER INFORMATION: X2 is a negatively charged amino acid (D, E)
<220> FEATURE:
<221> NAME/KEY: X5
<222> LOCATION: (12)..(12)
<223> OTHER INFORMATION: X5 is an amino acid with a polar, uncharged
      side chains (S, T, N, Q)
<220> FEATURE:
<221> NAME/KEY: X6
<222> LOCATION: (13)..(13)
<223> OTHER INFORMATION: X6 is a negatively charged amino acid (D, E)

<400> SEQUENCE: 4

Xaa Xaa Cys Thr Tyr Phe Gln Ala Tyr Gly Cys Xaa Xaa
1               5                   10

<210> SEQ ID NO 5
<211> LENGTH: 13
<212> TYPE: PRT
<213> ORGANISM: Artificial Sequence
<220> FEATURE:
<223> OTHER INFORMATION: artifical amino acid sequence
```

```
<220> FEATURE:
<221> NAME/KEY: X1
<222> LOCATION: (1)..(1)
<223> OTHER INFORMATION: X1 is a hydrophobic amino acid (A, I, L, M, F,
      W, Y, V)
<220> FEATURE:
<221> NAME/KEY: X2
<222> LOCATION: (2)..(2)
<223> OTHER INFORMATION: X2 is a negatively charged amino acid (D, E)
<220> FEATURE:
<221> NAME/KEY: X5
<222> LOCATION: (12)..(12)
<223> OTHER INFORMATION: X5 is an amino acid with a polar, uncharged
      side chains (S, T, N, Q)
<220> FEATURE:
<221> NAME/KEY: X6
<222> LOCATION: (13)..(13)
<223> OTHER INFORMATION: X6 is a negatively charged amino acid (D, E)

<400> SEQUENCE: 5

Xaa Xaa Asn Thr Tyr Phe Gln Ala Tyr Gly Asn Xaa Xaa
1               5                   10

<210> SEQ ID NO 6
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: X1
<222> LOCATION: (1)..(1)
<223> OTHER INFORMATION: X1 is a hydrophobic amino acid (A, I, L, M, F,
      W, Y, V)
<220> FEATURE:
<221> NAME/KEY: X2
<222> LOCATION: (2)..(2)
<223> OTHER INFORMATION: X2 is a negatively charged amino acid (D, E)
<220> FEATURE:
<221> NAME/KEY: X5
<222> LOCATION: (12)..(12)
<223> OTHER INFORMATION: X5 is an amino acid with a polar, uncharged
      side chains (S, T, N, Q)
<220> FEATURE:
<221> NAME/KEY: X6
<222> LOCATION: (13)..(13)
<223> OTHER INFORMATION: X6 is a negatively charged amino acid (D, E)

<400> SEQUENCE: 6

Xaa Xaa Asn Thr Tyr Phe Gln Ala Tyr Gly Cys Xaa Xaa
1               5                   10

<210> SEQ ID NO 7
<211> LENGTH: 13
<212> TYPE: PRT
<213> ORGANISM: Artificial Sequence
<220> FEATURE:
<223> OTHER INFORMATION: artifical amino acid sequence

<400> SEQUENCE: 7

Ala Asp Cys Thr Tyr Phe Gln Ala Tyr Gly Cys Ser Asp
1               5                   10

<210> SEQ ID NO 8
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 8

Val Asp Cys Thr Tyr Phe Gln Ala Tyr Gly Cys Ser Asp
1               5                   10

<210> SEQ ID NO 9
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 9

Ile Asp Cys Thr Tyr Phe Gln Ala Tyr Gly Cys Ser Asp
1               5                   10

<210> SEQ ID NO 10
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 10

Leu Asp Cys Thr Tyr Phe Gln Ala Tyr Gly Cys Ser Asp
1               5                   10

<210> SEQ ID NO 11
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 11

Met Asp Cys Thr Tyr Phe Gln Ala Tyr Gly Cys Ser Asp
1               5                   10

<210> SEQ ID NO 12
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 12

Gly Asp Cys Thr Tyr Phe Gln Ala Tyr Gly Cys Ser Asp
1               5                   10

<210> SEQ ID NO 13
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 13

Ala Glu Cys Thr Tyr Phe Gln Ala Tyr Gly Cys Ser Asp
1               5                   10

<210> SEQ ID NO 14
<211> LENGTH: 13
<212> TYPE: PRT
<213> ORGANISM: Artificial Sequence
<220> FEATURE:
<223> OTHER INFORMATION: artificial amino acid sequence
```

-continued

<400> SEQUENCE: 14

Val Glu Cys Thr Tyr Phe Gln Ala Tyr Gly Cys Ser Asp
1               5                   10

<210> SEQ ID NO 15
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 15

Ile Glu Cys Thr Tyr Phe Gln Ala Tyr Gly Cys Ser Asp
1               5                   10

<210> SEQ ID NO 16
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 16

Leu Glu Cys Thr Tyr Phe Gln Ala Tyr Gly Cys Ser Asp
1               5                   10

<210> SEQ ID NO 17
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 17

Met Glu Cys Thr Tyr Phe Gln Ala Tyr Gly Cys Ser Asp
1               5                   10

<210> SEQ ID NO 18
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 18

Gly Glu Cys Thr Tyr Phe Gln Ala Tyr Gly Cys Ser Asp
1               5                   10

<210> SEQ ID NO 19
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 19

Ala Asp Cys Thr Tyr Phe Gln Ala Tyr Gly Asn Ser Asp
1               5                   10

<210> SEQ ID NO 20
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 20

Val Asp Cys Thr Tyr Phe Gln Ala Tyr Gly Asn Ser Asp
1               5                   10

<210> SEQ ID NO 21
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 21

Ile Asp Cys Thr Tyr Phe Gln Ala Tyr Gly Asn Ser Asp
1               5                   10

<210> SEQ ID NO 22
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 22

Leu Asp Cys Thr Tyr Phe Gln Ala Tyr Gly Asn Ser Asp
1               5                   10

<210> SEQ ID NO 23
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 23

Met Asp Cys Thr Tyr Phe Gln Ala Tyr Gly Asn Ser Asp
1               5                   10

<210> SEQ ID NO 24
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 24

Gly Asp Cys Thr Tyr Phe Gln Ala Tyr Gly Asn Ser Asp
1               5                   10

<210> SEQ ID NO 25
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 25

Ala Glu Cys Thr Tyr Phe Gln Ala Tyr Gly Asn Ser Asp
1               5                   10

<210> SEQ ID NO 26
<211> LENGTH: 13
<212> TYPE: PRT
<213> ORGANISM: Artificial Sequence
<220> FEATURE:
<223> OTHER INFORMATION: artificial amino acid sequence

```
<400> SEQUENCE: 26

Val Glu Cys Thr Tyr Phe Gln Ala Tyr Gly Asn Ser Asp
1               5                   10

<210> SEQ ID NO 27
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 27

Ile Glu Cys Thr Tyr Phe Gln Ala Tyr Gly Asn Ser Asp
1               5                   10

<210> SEQ ID NO 28
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 28

Leu Glu Cys Thr Tyr Phe Gln Ala Tyr Gly Asn Ser Asp
1               5                   10

<210> SEQ ID NO 29
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 29

Met Glu Cys Thr Tyr Phe Gln Ala Tyr Gly Asn Ser Asp
1               5                   10

<210> SEQ ID NO 30
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 30

Gly Glu Cys Thr Tyr Phe Gln Ala Tyr Gly Asn Ser Asp
1               5                   10

<210> SEQ ID NO 31
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 31

Ala Asp Cys Thr Tyr Phe Gln Ala Tyr Gly Cys Ser Glu
1               5                   10

<210> SEQ ID NO 32
<211> LENGTH: 13
<212> TYPE: PRT
<213> ORGANISM: Artificial Sequence
<220> FEATURE:
<223> OTHER INFORMATION: artificial amino acid sequence
```

<400> SEQUENCE: 32

Val Asp Cys Thr Tyr Phe Gln Ala Tyr Gly Cys Ser Glu
1               5                   10

<210> SEQ ID NO 33
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 33

Ile Asp Cys Thr Tyr Phe Gln Ala Tyr Gly Cys Ser Glu
1               5                   10

<210> SEQ ID NO 34
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 34

Leu Asp Cys Thr Tyr Phe Gln Ala Tyr Gly Cys Ser Glu
1               5                   10

<210> SEQ ID NO 35
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 35

Met Asp Cys Thr Tyr Phe Gln Ala Tyr Gly Cys Ser Glu
1               5                   10

<210> SEQ ID NO 36
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 36

Gly Asp Cys Thr Tyr Phe Gln Ala Tyr Gly Cys Ser Glu
1               5                   10

<210> SEQ ID NO 37
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 37

Ala Glu Cys Thr Tyr Phe Gln Ala Tyr Gly Cys Ser Glu
1               5                   10

<210> SEQ ID NO 38
<211> LENGTH: 13
<212> TYPE: PRT
<213> ORGANISM: Artificial Sequence
<220> FEATURE:
<223> OTHER INFORMATION: artificial amino acid sequence

```
<400> SEQUENCE: 38

Val Glu Cys Thr Tyr Phe Gln Ala Tyr Gly Cys Ser Glu
1               5                   10

<210> SEQ ID NO 39
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 39

Ile Glu Cys Thr Tyr Phe Gln Ala Tyr Gly Cys Ser Glu
1               5                   10

<210> SEQ ID NO 40
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 40

Leu Glu Cys Thr Tyr Phe Gln Ala Tyr Gly Cys Ser Glu
1               5                   10

<210> SEQ ID NO 41
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 41

Met Glu Cys Thr Tyr Phe Gln Ala Tyr Gly Cys Ser Glu
1               5                   10

<210> SEQ ID NO 42
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 42

Gly Glu Cys Thr Tyr Phe Gln Ala Tyr Gly Cys Ser Glu
1               5                   10

<210> SEQ ID NO 43
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 43

Ala Asp Cys Thr Tyr Phe Gln Ala Tyr Gly Asn Ser Glu
1               5                   10

<210> SEQ ID NO 44
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 44

Val Asp Cys Thr Tyr Phe Gln Ala Tyr Gly Asn Ser Glu
1               5                   10

<210> SEQ ID NO 45
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 45

Ile Asp Cys Thr Tyr Phe Gln Ala Tyr Gly Asn Ser Glu
1               5                   10

<210> SEQ ID NO 46
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 46

Leu Asp Cys Thr Tyr Phe Gln Ala Tyr Gly Asn Ser Glu
1               5                   10

<210> SEQ ID NO 47
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 47

Met Asp Cys Thr Tyr Phe Gln Ala Tyr Gly Asn Ser Glu
1               5                   10

<210> SEQ ID NO 48
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 48

Gly Asp Cys Thr Tyr Phe Gln Ala Tyr Gly Asn Ser Glu
1               5                   10

<210> SEQ ID NO 49
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 49

Ala Glu Cys Thr Tyr Phe Gln Ala Tyr Gly Asn Ser Glu
1               5                   10

<210> SEQ ID NO 50
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 50

Val Glu Cys Thr Tyr Phe Gln Ala Tyr Gly Asn Ser Glu
1               5                   10

<210> SEQ ID NO 51
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 51

Ile Glu Cys Thr Tyr Phe Gln Ala Tyr Gly Asn Ser Glu
1               5                   10

<210> SEQ ID NO 52
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 52

Leu Glu Cys Thr Tyr Phe Gln Ala Tyr Gly Asn Ser Glu
1               5                   10

<210> SEQ ID NO 53
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 53

Met Glu Cys Thr Tyr Phe Gln Ala Tyr Gly Asn Ser Glu
1               5                   10

<210> SEQ ID NO 54
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 54

Gly Glu Cys Thr Tyr Phe Gln Ala Tyr Gly Asn Ser Glu
1               5                   10

<210> SEQ ID NO 55
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 55

Ala Asp Cys Thr Tyr Phe Gln Ala Tyr Gly Cys Thr Asp
1               5                   10

<210> SEQ ID NO 56
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 56

Val Asp Cys Thr Tyr Phe Gln Ala Tyr Gly Cys Thr Asp
1               5                   10

<210> SEQ ID NO 57
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 57

Ile Asp Cys Thr Tyr Phe Gln Ala Tyr Gly Cys Thr Asp
1               5                   10

<210> SEQ ID NO 58
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 58

Leu Asp Cys Thr Tyr Phe Gln Ala Tyr Gly Cys Thr Asp
1               5                   10

<210> SEQ ID NO 59
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 59

Met Asp Cys Thr Tyr Phe Gln Ala Tyr Gly Cys Thr Asp
1               5                   10

<210> SEQ ID NO 60
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 60

Gly Asp Cys Thr Tyr Phe Gln Ala Tyr Gly Cys Thr Asp
1               5                   10

<210> SEQ ID NO 61
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 61

Ala Glu Cys Thr Tyr Phe Gln Ala Tyr Gly Cys Thr Asp
1               5                   10

<210> SEQ ID NO 62
<211> LENGTH: 13
<212> TYPE: PRT
<213> ORGANISM: Artificial Sequence
<220> FEATURE:
<223> OTHER INFORMATION: artificial amino acid sequence
```

<400> SEQUENCE: 62

Val Glu Cys Thr Tyr Phe Gln Ala Tyr Gly Cys Thr Asp
1               5                   10

<210> SEQ ID NO 63
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 63

Ile Glu Cys Thr Tyr Phe Gln Ala Tyr Gly Cys Thr Asp
1               5                   10

<210> SEQ ID NO 64
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 64

Leu Glu Cys Thr Tyr Phe Gln Ala Tyr Gly Cys Thr Asp
1               5                   10

<210> SEQ ID NO 65
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 65

Met Glu Cys Thr Tyr Phe Gln Ala Tyr Gly Cys Thr Asp
1               5                   10

<210> SEQ ID NO 66
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 66

Gly Glu Cys Thr Tyr Phe Gln Ala Tyr Gly Cys Thr Asp
1               5                   10

<210> SEQ ID NO 67
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 67

Ala Asp Cys Thr Tyr Phe Gln Ala Tyr Gly Asn Thr Asp
1               5                   10

<210> SEQ ID NO 68
<211> LENGTH: 13
<212> TYPE: PRT
<213> ORGANISM: Artificial Sequence
<220> FEATURE:
<223> OTHER INFORMATION: artificial amino acid sequence

```
<400> SEQUENCE: 68

Val Asp Cys Thr Tyr Phe Gln Ala Tyr Gly Asn Thr Asp
1               5                   10

<210> SEQ ID NO 69
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 69

Ile Asp Cys Thr Tyr Phe Gln Ala Tyr Gly Asn Thr Asp
1               5                   10

<210> SEQ ID NO 70
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 70

Leu Asp Cys Thr Tyr Phe Gln Ala Tyr Gly Asn Thr Asp
1               5                   10

<210> SEQ ID NO 71
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 71

Met Asp Cys Thr Tyr Phe Gln Ala Tyr Gly Asn Thr Asp
1               5                   10

<210> SEQ ID NO 72
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 72

Gly Asp Cys Thr Tyr Phe Gln Ala Tyr Gly Asn Thr Asp
1               5                   10

<210> SEQ ID NO 73
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 73

Ala Glu Cys Thr Tyr Phe Gln Ala Tyr Gly Asn Thr Asp
1               5                   10

<210> SEQ ID NO 74
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 74

Val Glu Cys Thr Tyr Phe Gln Ala Tyr Gly Asn Thr Asp
1               5                   10

<210> SEQ ID NO 75
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 75

Ile Glu Cys Thr Tyr Phe Gln Ala Tyr Gly Asn Thr Asp
1               5                   10

<210> SEQ ID NO 76
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 76

Leu Glu Cys Thr Tyr Phe Gln Ala Tyr Gly Asn Thr Asp
1               5                   10

<210> SEQ ID NO 77
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 77

Met Glu Cys Thr Tyr Phe Gln Ala Tyr Gly Asn Thr Asp
1               5                   10

<210> SEQ ID NO 78
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 78

Gly Glu Cys Thr Tyr Phe Gln Ala Tyr Gly Asn Thr Asp
1               5                   10

<210> SEQ ID NO 79
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 79

Ala Asp Cys Thr Tyr Phe Gln Ala Tyr Gly Cys Thr Glu
1               5                   10

<210> SEQ ID NO 80
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 80

Val Asp Cys Thr Tyr Phe Gln Ala Tyr Gly Cys Thr Glu
1               5                   10

<210> SEQ ID NO 81
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 81

Ile Asp Cys Thr Tyr Phe Gln Ala Tyr Gly Cys Thr Glu
1               5                   10

<210> SEQ ID NO 82
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 82

Leu Asp Cys Thr Tyr Phe Gln Ala Tyr Gly Cys Thr Glu
1               5                   10

<210> SEQ ID NO 83
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 83

Met Asp Cys Thr Tyr Phe Gln Ala Tyr Gly Cys Thr Glu
1               5                   10

<210> SEQ ID NO 84
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 84

Gly Asp Cys Thr Tyr Phe Gln Ala Tyr Gly Cys Thr Glu
1               5                   10

<210> SEQ ID NO 85
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 85

Ala Glu Cys Thr Tyr Phe Gln Ala Tyr Gly Cys Thr Glu
1               5                   10

<210> SEQ ID NO 86
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 86

Val Glu Cys Thr Tyr Phe Gln Ala Tyr Gly Cys Thr Glu
1               5                   10

<210> SEQ ID NO 87
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 87

Ile Glu Cys Thr Tyr Phe Gln Ala Tyr Gly Cys Thr Glu
1               5                   10

<210> SEQ ID NO 88
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 88

Leu Glu Cys Thr Tyr Phe Gln Ala Tyr Gly Cys Thr Glu
1               5                   10

<210> SEQ ID NO 89
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 89

Met Glu Cys Thr Tyr Phe Gln Ala Tyr Gly Cys Thr Glu
1               5                   10

<210> SEQ ID NO 90
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 90

Gly Glu Cys Thr Tyr Phe Gln Ala Tyr Gly Cys Thr Glu
1               5                   10

<210> SEQ ID NO 91
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 91

Ala Asp Cys Thr Tyr Phe Gln Ala Tyr Gly Asn Thr Glu
1               5                   10

<210> SEQ ID NO 92
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 92

Val Asp Cys Thr Tyr Phe Gln Ala Tyr Gly Asn Thr Glu
1               5                   10

<210> SEQ ID NO 93
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 93

Ile Asp Cys Thr Tyr Phe Gln Ala Tyr Gly Asn Thr Glu
1               5                   10

<210> SEQ ID NO 94
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 94

Leu Asp Cys Thr Tyr Phe Gln Ala Tyr Gly Asn Thr Glu
1               5                   10

<210> SEQ ID NO 95
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 95

Met Asp Cys Thr Tyr Phe Gln Ala Tyr Gly Asn Thr Glu
1               5                   10

<210> SEQ ID NO 96
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 96

Gly Asp Cys Thr Tyr Phe Gln Ala Tyr Gly Asn Thr Glu
1               5                   10

<210> SEQ ID NO 97
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 97

Ala Glu Cys Thr Tyr Phe Gln Ala Tyr Gly Asn Thr Glu
1               5                   10

<210> SEQ ID NO 98
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 98

Val Glu Cys Thr Tyr Phe Gln Ala Tyr Gly Asn Thr Glu
1               5                   10

<210> SEQ ID NO 99
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 99

Ile Glu Cys Thr Tyr Phe Gln Ala Tyr Gly Asn Thr Glu
1               5                   10

<210> SEQ ID NO 100
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 100

Leu Glu Cys Thr Tyr Phe Gln Ala Tyr Gly Asn Thr Glu
1               5                   10

<210> SEQ ID NO 101
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 101

Met Glu Cys Thr Tyr Phe Gln Ala Tyr Gly Asn Thr Glu
1               5                   10

<210> SEQ ID NO 102
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 102

Gly Glu Cys Thr Tyr Phe Gln Ala Tyr Gly Asn Thr Glu
1               5                   10

<210> SEQ ID NO 103
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 103

Ala Asp Cys Thr Tyr Phe Gln Ala Tyr Gly Cys Asn Asp
1               5                   10

<210> SEQ ID NO 104
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 104

Val Asp Cys Thr Tyr Phe Gln Ala Tyr Gly Cys Asn Asp
1               5                   10

<210> SEQ ID NO 105
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 105

Ile Asp Cys Thr Tyr Phe Gln Ala Tyr Gly Cys Asn Asp
1               5                   10

<210> SEQ ID NO 106
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 106

Leu Asp Cys Thr Tyr Phe Gln Ala Tyr Gly Cys Asn Asp
1               5                   10

<210> SEQ ID NO 107
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 107

Met Asp Cys Thr Tyr Phe Gln Ala Tyr Gly Cys Asn Asp
1               5                   10

<210> SEQ ID NO 108
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 108

Gly Asp Cys Thr Tyr Phe Gln Ala Tyr Gly Cys Asn Asp
1               5                   10

<210> SEQ ID NO 109
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 109

Ala Glu Cys Thr Tyr Phe Gln Ala Tyr Gly Cys Asn Asp
1               5                   10

<210> SEQ ID NO 110
<211> LENGTH: 13
<212> TYPE: PRT
<213> ORGANISM: Artificial Sequence
<220> FEATURE:
<223> OTHER INFORMATION: artificial amino acid sequence
```

-continued

```
<400> SEQUENCE: 110

Val Glu Cys Thr Tyr Phe Gln Ala Tyr Gly Cys Asn Asp
1               5                   10

<210> SEQ ID NO 111
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 111

Ile Glu Cys Thr Tyr Phe Gln Ala Tyr Gly Cys Asn Asp
1               5                   10

<210> SEQ ID NO 112
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 112

Leu Glu Cys Thr Tyr Phe Gln Ala Tyr Gly Cys Asn Asp
1               5                   10

<210> SEQ ID NO 113
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 113

Met Glu Cys Thr Tyr Phe Gln Ala Tyr Gly Cys Asn Asp
1               5                   10

<210> SEQ ID NO 114
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 114

Gly Glu Cys Thr Tyr Phe Gln Ala Tyr Gly Cys Asn Asp
1               5                   10

<210> SEQ ID NO 115
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 115

Ala Asp Cys Thr Tyr Phe Gln Ala Tyr Gly Asn Asn Asp
1               5                   10

<210> SEQ ID NO 116
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 116

Val Asp Cys Thr Tyr Phe Gln Ala Tyr Gly Asn Asn Asp
1               5                   10

<210> SEQ ID NO 117
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 117

Ile Asp Cys Thr Tyr Phe Gln Ala Tyr Gly Asn Asn Asp
1               5                   10

<210> SEQ ID NO 118
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 118

Leu Asp Cys Thr Tyr Phe Gln Ala Tyr Gly Asn Asn Asp
1               5                   10

<210> SEQ ID NO 119
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 119

Met Asp Cys Thr Tyr Phe Gln Ala Tyr Gly Asn Asn Asp
1               5                   10

<210> SEQ ID NO 120
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 120

Gly Asp Cys Thr Tyr Phe Gln Ala Tyr Gly Asn Asn Asp
1               5                   10

<210> SEQ ID NO 121
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 121

Val Glu Cys Thr Tyr Phe Gln Ala Tyr Gly Asn Asn Asp
1               5                   10

<210> SEQ ID NO 122
<211> LENGTH: 13
<212> TYPE: PRT
<213> ORGANISM: Artificial Sequence
<220> FEATURE:
<223> OTHER INFORMATION: artificial amino acid sequence
```

<400> SEQUENCE: 122

Ile Glu Cys Thr Tyr Phe Gln Ala Tyr Gly Asn Asn Asp
1               5                   10

<210> SEQ ID NO 123
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 123

Leu Glu Cys Thr Tyr Phe Gln Ala Tyr Gly Asn Asn Asp
1               5                   10

<210> SEQ ID NO 124
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 124

Met Glu Cys Thr Tyr Phe Gln Ala Tyr Gly Asn Asn Asp
1               5                   10

<210> SEQ ID NO 125
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 125

Gly Glu Cys Thr Tyr Phe Gln Ala Tyr Gly Asn Asn Asp
1               5                   10

<210> SEQ ID NO 126
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 126

Ala Asp Cys Thr Tyr Phe Gln Ala Tyr Gly Cys Asn Glu
1               5                   10

<210> SEQ ID NO 127
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 127

Val Asp Cys Thr Tyr Phe Gln Ala Tyr Gly Cys Asn Glu
1               5                   10

<210> SEQ ID NO 128
<211> LENGTH: 13
<212> TYPE: PRT
<213> ORGANISM: Artificial Sequence
<220> FEATURE:
<223> OTHER INFORMATION: artificial amino acid sequence

```
<400> SEQUENCE: 128

Ile Asp Cys Thr Tyr Phe Gln Ala Tyr Gly Cys Asn Glu
1               5                   10

<210> SEQ ID NO 129
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 129

Leu Asp Cys Thr Tyr Phe Gln Ala Tyr Gly Cys Asn Glu
1               5                   10

<210> SEQ ID NO 130
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 130

Met Asp Cys Thr Tyr Phe Gln Ala Tyr Gly Cys Asn Glu
1               5                   10

<210> SEQ ID NO 131
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 131

Gly Asp Cys Thr Tyr Phe Gln Ala Tyr Gly Cys Asn Glu
1               5                   10

<210> SEQ ID NO 132
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 132

Ala Glu Cys Thr Tyr Phe Gln Ala Tyr Gly Cys Asn Glu
1               5                   10

<210> SEQ ID NO 133
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 133

Val Glu Cys Thr Tyr Phe Gln Ala Tyr Gly Cys Asn Glu
1               5                   10

<210> SEQ ID NO 134
<211> LENGTH: 13
<212> TYPE: PRT
<213> ORGANISM: Artificial Sequence
<220> FEATURE:
<223> OTHER INFORMATION: artificial amino acid sequence
```

<400> SEQUENCE: 134

Ile Glu Cys Thr Tyr Phe Gln Ala Tyr Gly Cys Asn Glu
1               5                   10

<210> SEQ ID NO 135
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 135

Leu Glu Cys Thr Tyr Phe Gln Ala Tyr Gly Cys Asn Glu
1               5                   10

<210> SEQ ID NO 136
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 136

Met Glu Cys Thr Tyr Phe Gln Ala Tyr Gly Cys Asn Glu
1               5                   10

<210> SEQ ID NO 137
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 137

Gly Glu Cys Thr Tyr Phe Gln Ala Tyr Gly Cys Asn Glu
1               5                   10

<210> SEQ ID NO 138
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 138

Ala Asp Cys Thr Tyr Phe Gln Ala Tyr Gly Asn Asn Glu
1               5                   10

<210> SEQ ID NO 139
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 139

Val Asp Cys Thr Tyr Phe Gln Ala Tyr Gly Asn Asn Glu
1               5                   10

<210> SEQ ID NO 140
<211> LENGTH: 13
<212> TYPE: PRT
<213> ORGANISM: Artificial Sequence
<220> FEATURE:
<223> OTHER INFORMATION: artificial amino acid sequence

```
<400> SEQUENCE: 140

Ile Asp Cys Thr Tyr Phe Gln Ala Tyr Gly Asn Asn Glu
1               5                   10

<210> SEQ ID NO 141
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 141

Leu Asp Cys Thr Tyr Phe Gln Ala Tyr Gly Asn Asn Glu
1               5                   10

<210> SEQ ID NO 142
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 142

Met Asp Cys Thr Tyr Phe Gln Ala Tyr Gly Asn Asn Glu
1               5                   10

<210> SEQ ID NO 143
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 143

Gly Asp Cys Thr Tyr Phe Gln Ala Tyr Gly Asn Asn Glu
1               5                   10

<210> SEQ ID NO 144
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 144

Ala Glu Cys Thr Tyr Phe Gln Ala Tyr Gly Asn Asn Glu
1               5                   10

<210> SEQ ID NO 145
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 145

Val Glu Cys Thr Tyr Phe Gln Ala Tyr Gly Asn Asn Glu
1               5                   10

<210> SEQ ID NO 146
<211> LENGTH: 13
<212> TYPE: PRT
<213> ORGANISM: Artificial Sequence
<220> FEATURE:
<223> OTHER INFORMATION: artificial amino acid sequence
```

<400> SEQUENCE: 146

Ile Glu Cys Thr Tyr Phe Gln Ala Tyr Gly Asn Asn Glu
1               5                   10

<210> SEQ ID NO 147
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 147

Leu Glu Cys Thr Tyr Phe Gln Ala Tyr Gly Asn Asn Glu
1               5                   10

<210> SEQ ID NO 148
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 148

Met Glu Cys Thr Tyr Phe Gln Ala Tyr Gly Asn Asn Glu
1               5                   10

<210> SEQ ID NO 149
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 149

Gly Glu Cys Thr Tyr Phe Gln Ala Tyr Gly Asn Asn Glu
1               5                   10

<210> SEQ ID NO 150
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 150

Ala Asp Asn Thr Tyr Phe Gln Ala Tyr Gly Cys Ser Asp
1               5                   10

<210> SEQ ID NO 151
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 151

Val Asp Asn Thr Tyr Phe Gln Ala Tyr Gly Cys Ser Asp
1               5                   10

<210> SEQ ID NO 152
<211> LENGTH: 13
<212> TYPE: PRT
<213> ORGANISM: Artificial Sequence
<220> FEATURE:
<223> OTHER INFORMATION: artificial amino acid sequence

```
<400> SEQUENCE: 152

Ile Asp Asn Thr Tyr Phe Gln Ala Tyr Gly Cys Ser Asp
1               5                   10

<210> SEQ ID NO 153
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 153

Leu Asp Asn Thr Tyr Phe Gln Ala Tyr Gly Cys Ser Asp
1               5                   10

<210> SEQ ID NO 154
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 154

Met Asp Asn Thr Tyr Phe Gln Ala Tyr Gly Cys Ser Asp
1               5                   10

<210> SEQ ID NO 155
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 155

Gly Asp Asn Thr Tyr Phe Gln Ala Tyr Gly Cys Ser Asp
1               5                   10

<210> SEQ ID NO 156
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 156

Ala Glu Asn Thr Tyr Phe Gln Ala Tyr Gly Cys Ser Asp
1               5                   10

<210> SEQ ID NO 157
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 157

Val Glu Asn Thr Tyr Phe Gln Ala Tyr Gly Cys Ser Asp
1               5                   10

<210> SEQ ID NO 158
<211> LENGTH: 13
<212> TYPE: PRT
<213> ORGANISM: Artificial Sequence
<220> FEATURE:
<223> OTHER INFORMATION: artificial amino acid sequence
```

<400> SEQUENCE: 158

Ile Glu Asn Thr Tyr Phe Gln Ala Tyr Gly Cys Ser Asp
1               5                   10

<210> SEQ ID NO 159
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 159

Leu Glu Asn Thr Tyr Phe Gln Ala Tyr Gly Cys Ser Asp
1               5                   10

<210> SEQ ID NO 160
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 160

Met Glu Asn Thr Tyr Phe Gln Ala Tyr Gly Cys Ser Asp
1               5                   10

<210> SEQ ID NO 161
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 161

Gly Glu Asn Thr Tyr Phe Gln Ala Tyr Gly Cys Ser Asp
1               5                   10

<210> SEQ ID NO 162
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 162

Ala Asp Asn Thr Tyr Phe Gln Ala Tyr Gly Asn Ser Asp
1               5                   10

<210> SEQ ID NO 163
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 163

Val Asp Asn Thr Tyr Phe Gln Ala Tyr Gly Asn Ser Asp
1               5                   10

<210> SEQ ID NO 164
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 164

Ile Asp Asn Thr Tyr Phe Gln Ala Tyr Gly Asn Ser Asp
1               5                   10

<210> SEQ ID NO 165
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 165

Leu Asp Asn Thr Tyr Phe Gln Ala Tyr Gly Asn Ser Asp
1               5                   10

<210> SEQ ID NO 166
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 166

Met Asp Asn Thr Tyr Phe Gln Ala Tyr Gly Asn Ser Asp
1               5                   10

<210> SEQ ID NO 167
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 167

Gly Asp Asn Thr Tyr Phe Gln Ala Tyr Gly Asn Ser Asp
1               5                   10

<210> SEQ ID NO 168
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 168

Ala Glu Asn Thr Tyr Phe Gln Ala Tyr Gly Asn Ser Asp
1               5                   10

<210> SEQ ID NO 169
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 169

Val Glu Asn Thr Tyr Phe Gln Ala Tyr Gly Asn Ser Asp
1               5                   10

<210> SEQ ID NO 170
<211> LENGTH: 13
<212> TYPE: PRT
<213> ORGANISM: Artificial Sequence
<220> FEATURE:
<223> OTHER INFORMATION: artificial amino acid sequence

```
<400> SEQUENCE: 170

Ile Glu Asn Thr Tyr Phe Gln Ala Tyr Gly Asn Ser Asp
1               5                   10

<210> SEQ ID NO 171
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 171

Leu Glu Asn Thr Tyr Phe Gln Ala Tyr Gly Asn Ser Asp
1               5                   10

<210> SEQ ID NO 172
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 172

Met Glu Asn Thr Tyr Phe Gln Ala Tyr Gly Asn Ser Asp
1               5                   10

<210> SEQ ID NO 173
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 173

Gly Glu Asn Thr Tyr Phe Gln Ala Tyr Gly Asn Ser Asp
1               5                   10

<210> SEQ ID NO 174
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 174

Ala Asp Asn Thr Tyr Phe Gln Ala Tyr Gly Cys Ser Glu
1               5                   10

<210> SEQ ID NO 175
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 175

Val Asp Asn Thr Tyr Phe Gln Ala Tyr Gly Cys Ser Glu
1               5                   10

<210> SEQ ID NO 176
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 176

Ile Asp Asn Thr Tyr Phe Gln Ala Tyr Gly Cys Ser Glu
1               5                   10

<210> SEQ ID NO 177
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 177

Leu Asp Asn Thr Tyr Phe Gln Ala Tyr Gly Cys Ser Glu
1               5                   10

<210> SEQ ID NO 178
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 178

Met Asp Asn Thr Tyr Phe Gln Ala Tyr Gly Cys Ser Glu
1               5                   10

<210> SEQ ID NO 179
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 179

Gly Asp Asn Thr Tyr Phe Gln Ala Tyr Gly Cys Ser Glu
1               5                   10

<210> SEQ ID NO 180
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 180

Ala Glu Asn Thr Tyr Phe Gln Ala Tyr Gly Cys Ser Glu
1               5                   10

<210> SEQ ID NO 181
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 181

Val Glu Asn Thr Tyr Phe Gln Ala Tyr Gly Cys Ser Glu
1               5                   10

<210> SEQ ID NO 182
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 182

Ile Glu Asn Thr Tyr Phe Gln Ala Tyr Gly Cys Ser Glu
1               5                   10

<210> SEQ ID NO 183
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 183

Leu Glu Asn Thr Tyr Phe Gln Ala Tyr Gly Cys Ser Glu
1               5                   10

<210> SEQ ID NO 184
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 184

Met Glu Asn Thr Tyr Phe Gln Ala Tyr Gly Cys Ser Glu
1               5                   10

<210> SEQ ID NO 185
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 185

Gly Glu Asn Thr Tyr Phe Gln Ala Tyr Gly Cys Ser Glu
1               5                   10

<210> SEQ ID NO 186
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 186

Ala Asp Asn Thr Tyr Phe Gln Ala Tyr Gly Asn Ser Glu
1               5                   10

<210> SEQ ID NO 187
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 187

Val Asp Asn Thr Tyr Phe Gln Ala Tyr Gly Asn Ser Glu
1               5                   10

<210> SEQ ID NO 188
<211> LENGTH: 13
<212> TYPE: PRT
<213> ORGANISM: Artificial Sequence
<220> FEATURE:
<223> OTHER INFORMATION: artificial amino acid sequence
```

-continued

<400> SEQUENCE: 188

Ile Asp Asn Thr Tyr Phe Gln Ala Tyr Gly Asn Ser Glu
1               5                   10

<210> SEQ ID NO 189
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 189

Leu Asp Asn Thr Tyr Phe Gln Ala Tyr Gly Asn Ser Glu
1               5                   10

<210> SEQ ID NO 190
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 190

Met Asp Asn Thr Tyr Phe Gln Ala Tyr Gly Asn Ser Glu
1               5                   10

<210> SEQ ID NO 191
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 191

Gly Asp Asn Thr Tyr Phe Gln Ala Tyr Gly Asn Ser Glu
1               5                   10

<210> SEQ ID NO 192
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 192

Ala Glu Asn Thr Tyr Phe Gln Ala Tyr Gly Asn Ser Glu
1               5                   10

<210> SEQ ID NO 193
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 193

Val Glu Asn Thr Tyr Phe Gln Ala Tyr Gly Asn Ser Glu
1               5                   10

<210> SEQ ID NO 194
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 194

Ile Glu Asn Thr Tyr Phe Gln Ala Tyr Gly Asn Ser Glu
1               5                   10

<210> SEQ ID NO 195
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 195

Leu Glu Asn Thr Tyr Phe Gln Ala Tyr Gly Asn Ser Glu
1               5                   10

<210> SEQ ID NO 196
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 196

Met Glu Asn Thr Tyr Phe Gln Ala Tyr Gly Asn Ser Glu
1               5                   10

<210> SEQ ID NO 197
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 197

Gly Glu Asn Thr Tyr Phe Gln Ala Tyr Gly Asn Ser Glu
1               5                   10

<210> SEQ ID NO 198
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 198

Ala Asp Asn Thr Tyr Phe Gln Ala Tyr Gly Cys Thr Asp
1               5                   10

<210> SEQ ID NO 199
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 199

Val Asp Asn Thr Tyr Phe Gln Ala Tyr Gly Cys Thr Asp
1               5                   10

<210> SEQ ID NO 200
<211> LENGTH: 13
<212> TYPE: PRT
<213> ORGANISM: Artificial Sequence
<220> FEATURE:
<223> OTHER INFORMATION: artificial amino acid sequence

```
<400> SEQUENCE: 200

Ile Asp Asn Thr Tyr Phe Gln Ala Tyr Gly Cys Thr Asp
1               5                   10

<210> SEQ ID NO 201
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 201

Leu Asp Asn Thr Tyr Phe Gln Ala Tyr Gly Cys Thr Asp
1               5                   10

<210> SEQ ID NO 202
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 202

Met Asp Asn Thr Tyr Phe Gln Ala Tyr Gly Cys Thr Asp
1               5                   10

<210> SEQ ID NO 203
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 203

Gly Asp Asn Thr Tyr Phe Gln Ala Tyr Gly Cys Thr Asp
1               5                   10

<210> SEQ ID NO 204
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 204

Ala Glu Asn Thr Tyr Phe Gln Ala Tyr Gly Cys Thr Asp
1               5                   10

<210> SEQ ID NO 205
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 205

Val Glu Asn Thr Tyr Phe Gln Ala Tyr Gly Cys Thr Asp
1               5                   10

<210> SEQ ID NO 206
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 206

Ile Glu Asn Thr Tyr Phe Gln Ala Tyr Gly Cys Thr Asp
1               5                   10

<210> SEQ ID NO 207
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 207

Leu Glu Asn Thr Tyr Phe Gln Ala Tyr Gly Cys Thr Asp
1               5                   10

<210> SEQ ID NO 208
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 208

Met Glu Asn Thr Tyr Phe Gln Ala Tyr Gly Cys Thr Asp
1               5                   10

<210> SEQ ID NO 209
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 209

Gly Glu Asn Thr Tyr Phe Gln Ala Tyr Gly Cys Thr Asp
1               5                   10

<210> SEQ ID NO 210
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 210

Ala Asp Asn Thr Tyr Phe Gln Ala Tyr Gly Asn Thr Asp
1               5                   10

<210> SEQ ID NO 211
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 211

Val Asp Asn Thr Tyr Phe Gln Ala Tyr Gly Asn Thr Asp
1               5                   10

<210> SEQ ID NO 212
<211> LENGTH: 13
<212> TYPE: PRT
<213> ORGANISM: Artificial Sequence
<220> FEATURE:
<223> OTHER INFORMATION: artificial amino acid sequence
```

<400> SEQUENCE: 212

Ile Asp Asn Thr Tyr Phe Gln Ala Tyr Gly Asn Thr Asp
1               5                   10

<210> SEQ ID NO 213
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 213

Leu Asp Asn Thr Tyr Phe Gln Ala Tyr Gly Asn Thr Asp
1               5                   10

<210> SEQ ID NO 214
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 214

Met Asp Asn Thr Tyr Phe Gln Ala Tyr Gly Asn Thr Asp
1               5                   10

<210> SEQ ID NO 215
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 215

Gly Asp Asn Thr Tyr Phe Gln Ala Tyr Gly Asn Thr Asp
1               5                   10

<210> SEQ ID NO 216
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 216

Ala Glu Asn Thr Tyr Phe Gln Ala Tyr Gly Asn Thr Asp
1               5                   10

<210> SEQ ID NO 217
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 217

Val Glu Asn Thr Tyr Phe Gln Ala Tyr Gly Asn Thr Asp
1               5                   10

<210> SEQ ID NO 218
<211> LENGTH: 13
<212> TYPE: PRT
<213> ORGANISM: Artificial Sequence
<220> FEATURE:
<223> OTHER INFORMATION: artificial amino acid sequence

```
<400> SEQUENCE: 218

Ile Glu Asn Thr Tyr Phe Gln Ala Tyr Gly Asn Thr Asp
1               5                   10

<210> SEQ ID NO 219
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 219

Leu Glu Asn Thr Tyr Phe Gln Ala Tyr Gly Asn Thr Asp
1               5                   10

<210> SEQ ID NO 220
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 220

Met Glu Asn Thr Tyr Phe Gln Ala Tyr Gly Asn Thr Asp
1               5                   10

<210> SEQ ID NO 221
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 221

Gly Glu Asn Thr Tyr Phe Gln Ala Tyr Gly Asn Thr Asp
1               5                   10

<210> SEQ ID NO 222
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 222

Ala Asp Asn Thr Tyr Phe Gln Ala Tyr Gly Cys Thr Glu
1               5                   10

<210> SEQ ID NO 223
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 223

Val Asp Asn Thr Tyr Phe Gln Ala Tyr Gly Cys Thr Glu
1               5                   10

<210> SEQ ID NO 224
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 224

Ile Asp Asn Thr Tyr Phe Gln Ala Tyr Gly Cys Thr Glu
1               5                   10

<210> SEQ ID NO 225
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 225

Leu Asp Asn Thr Tyr Phe Gln Ala Tyr Gly Cys Thr Glu
1               5                   10

<210> SEQ ID NO 226
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 226

Met Asp Asn Thr Tyr Phe Gln Ala Tyr Gly Cys Thr Glu
1               5                   10

<210> SEQ ID NO 227
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 227

Gly Asp Asn Thr Tyr Phe Gln Ala Tyr Gly Cys Thr Glu
1               5                   10

<210> SEQ ID NO 228
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 228

Ala Glu Asn Thr Tyr Phe Gln Ala Tyr Gly Cys Thr Glu
1               5                   10

<210> SEQ ID NO 229
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 229

Val Glu Asn Thr Tyr Phe Gln Ala Tyr Gly Cys Thr Glu
1               5                   10

<210> SEQ ID NO 230
<211> LENGTH: 13
<212> TYPE: PRT
<213> ORGANISM: Artificial Sequence
<220> FEATURE:
<223> OTHER INFORMATION: artificial amino acid sequence
```

<400> SEQUENCE: 230

Ile Glu Asn Thr Tyr Phe Gln Ala Tyr Gly Cys Thr Glu
1               5                   10

<210> SEQ ID NO 231
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 231

Leu Glu Asn Thr Tyr Phe Gln Ala Tyr Gly Cys Thr Glu
1               5                   10

<210> SEQ ID NO 232
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 232

Met Glu Asn Thr Tyr Phe Gln Ala Tyr Gly Cys Thr Glu
1               5                   10

<210> SEQ ID NO 233
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 233

Gly Glu Asn Thr Tyr Phe Gln Ala Tyr Gly Cys Thr Glu
1               5                   10

<210> SEQ ID NO 234
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 234

Ala Asp Asn Thr Tyr Phe Gln Ala Tyr Gly Asn Thr Glu
1               5                   10

<210> SEQ ID NO 235
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 235

Val Asp Asn Thr Tyr Phe Gln Ala Tyr Gly Asn Thr Glu
1               5                   10

<210> SEQ ID NO 236
<211> LENGTH: 13
<212> TYPE: PRT
<213> ORGANISM: Artificial Sequence
<220> FEATURE:
<223> OTHER INFORMATION: artificial amino acid sequence

```
<400> SEQUENCE: 236

Ile Asp Asn Thr Tyr Phe Gln Ala Tyr Gly Asn Thr Glu
1               5                   10

<210> SEQ ID NO 237
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 237

Leu Asp Asn Thr Tyr Phe Gln Ala Tyr Gly Asn Thr Glu
1               5                   10

<210> SEQ ID NO 238
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 238

Met Asp Asn Thr Tyr Phe Gln Ala Tyr Gly Asn Thr Glu
1               5                   10

<210> SEQ ID NO 239
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 239

Gly Asp Asn Thr Tyr Phe Gln Ala Tyr Gly Asn Thr Glu
1               5                   10

<210> SEQ ID NO 240
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 240

Ala Glu Asn Thr Tyr Phe Gln Ala Tyr Gly Asn Thr Glu
1               5                   10

<210> SEQ ID NO 241
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 241

Val Glu Asn Thr Tyr Phe Gln Ala Tyr Gly Asn Thr Glu
1               5                   10

<210> SEQ ID NO 242
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 242

Ile Glu Asn Thr Tyr Phe Gln Ala Tyr Gly Asn Thr Glu
1               5                   10

<210> SEQ ID NO 243
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 243

Leu Glu Asn Thr Tyr Phe Gln Ala Tyr Gly Asn Thr Glu
1               5                   10

<210> SEQ ID NO 244
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 244

Met Glu Asn Thr Tyr Phe Gln Ala Tyr Gly Asn Thr Glu
1               5                   10

<210> SEQ ID NO 245
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 245

Gly Glu Asn Thr Tyr Phe Gln Ala Tyr Gly Asn Thr Glu
1               5                   10

<210> SEQ ID NO 246
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 246

Ala Asp Asn Thr Tyr Phe Gln Ala Tyr Gly Cys Asn Asp
1               5                   10

<210> SEQ ID NO 247
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 247

Val Asp Asn Thr Tyr Phe Gln Ala Tyr Gly Cys Asn Asp
1               5                   10

<210> SEQ ID NO 248
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 248

Ile Asp Asn Thr Tyr Phe Gln Ala Tyr Gly Cys Asn Asp
1               5                   10

<210> SEQ ID NO 249
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 249

Leu Asp Asn Thr Tyr Phe Gln Ala Tyr Gly Cys Asn Asp
1               5                   10

<210> SEQ ID NO 250
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 250

Met Asp Asn Thr Tyr Phe Gln Ala Tyr Gly Cys Asn Asp
1               5                   10

<210> SEQ ID NO 251
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 251

Gly Asp Asn Thr Tyr Phe Gln Ala Tyr Gly Cys Asn Asp
1               5                   10

<210> SEQ ID NO 252
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 252

Ala Glu Asn Thr Tyr Phe Gln Ala Tyr Gly Cys Asn Asp
1               5                   10

<210> SEQ ID NO 253
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 253

Val Glu Asn Thr Tyr Phe Gln Ala Tyr Gly Cys Asn Asp
1               5                   10

<210> SEQ ID NO 254
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 254

Ile Glu Asn Thr Tyr Phe Gln Ala Tyr Gly Cys Asn Asp
1               5                   10

<210> SEQ ID NO 255
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 255

Leu Glu Asn Thr Tyr Phe Gln Ala Tyr Gly Cys Asn Asp
1               5                   10

<210> SEQ ID NO 256
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 256

Met Glu Asn Thr Tyr Phe Gln Ala Tyr Gly Cys Asn Asp
1               5                   10

<210> SEQ ID NO 257
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 257

Gly Glu Asn Thr Tyr Phe Gln Ala Tyr Gly Cys Asn Asp
1               5                   10

<210> SEQ ID NO 258
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 258

Ala Asp Asn Thr Tyr Phe Gln Ala Tyr Gly Asn Asn Asp
1               5                   10

<210> SEQ ID NO 259
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 259

Val Asp Asn Thr Tyr Phe Gln Ala Tyr Gly Asn Asn Asp
1               5                   10

<210> SEQ ID NO 260
<211> LENGTH: 13
<212> TYPE: PRT
<213> ORGANISM: Artificial Sequence
<220> FEATURE:
<223> OTHER INFORMATION: artificial amino acid sequence
```

<400> SEQUENCE: 260

Ile Asp Asn Thr Tyr Phe Gln Ala Tyr Gly Asn Asn Asp
1               5                   10

<210> SEQ ID NO 261
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 261

Leu Asp Asn Thr Tyr Phe Gln Ala Tyr Gly Asn Asn Asp
1               5                   10

<210> SEQ ID NO 262
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 262

Met Asp Asn Thr Tyr Phe Gln Ala Tyr Gly Asn Asn Asp
1               5                   10

<210> SEQ ID NO 263
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 263

Gly Asp Asn Thr Tyr Phe Gln Ala Tyr Gly Asn Asn Asp
1               5                   10

<210> SEQ ID NO 264
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 264

Ala Glu Asn Thr Tyr Phe Gln Ala Tyr Gly Asn Asn Asp
1               5                   10

<210> SEQ ID NO 265
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 265

Val Glu Asn Thr Tyr Phe Gln Ala Tyr Gly Asn Asn Asp
1               5                   10

<210> SEQ ID NO 266
<211> LENGTH: 13
<212> TYPE: PRT
<213> ORGANISM: Artificial Sequence
<220> FEATURE:
<223> OTHER INFORMATION: artificial amino acid sequence

```
<400> SEQUENCE: 266

Ile Glu Asn Thr Tyr Phe Gln Ala Tyr Gly Asn Asn Asp
1               5                   10

<210> SEQ ID NO 267
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 267

Leu Glu Asn Thr Tyr Phe Gln Ala Tyr Gly Asn Asn Asp
1               5                   10

<210> SEQ ID NO 268
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 268

Met Glu Asn Thr Tyr Phe Gln Ala Tyr Gly Asn Asn Asp
1               5                   10

<210> SEQ ID NO 269
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 269

Gly Glu Asn Thr Tyr Phe Gln Ala Tyr Gly Asn Asn Asp
1               5                   10

<210> SEQ ID NO 270
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 270

Ala Asp Asn Thr Tyr Phe Gln Ala Tyr Gly Cys Asn Glu
1               5                   10

<210> SEQ ID NO 271
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 271

Val Asp Asn Thr Tyr Phe Gln Ala Tyr Gly Cys Asn Glu
1               5                   10

<210> SEQ ID NO 272
<211> LENGTH: 13
<212> TYPE: PRT
<213> ORGANISM: Artificial Sequence
<220> FEATURE:
<223> OTHER INFORMATION: artificial amino acid sequence
```

<400> SEQUENCE: 272

Ile Asp Asn Thr Tyr Phe Gln Ala Tyr Gly Cys Asn Glu
1               5                   10

<210> SEQ ID NO 273
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 273

Leu Asp Asn Thr Tyr Phe Gln Ala Tyr Gly Cys Asn Glu
1               5                   10

<210> SEQ ID NO 274
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 274

Met Asp Asn Thr Tyr Phe Gln Ala Tyr Gly Cys Asn Glu
1               5                   10

<210> SEQ ID NO 275
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 275

Gly Asp Asn Thr Tyr Phe Gln Ala Tyr Gly Cys Asn Glu
1               5                   10

<210> SEQ ID NO 276
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 276

Ala Glu Asn Thr Tyr Phe Gln Ala Tyr Gly Cys Asn Glu
1               5                   10

<210> SEQ ID NO 277
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 277

Val Glu Asn Thr Tyr Phe Gln Ala Tyr Gly Cys Asn Glu
1               5                   10

<210> SEQ ID NO 278
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 278

Ile Glu Asn Thr Tyr Phe Gln Ala Tyr Gly Cys Asn Glu
1               5                   10

<210> SEQ ID NO 279
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 279

Leu Glu Asn Thr Tyr Phe Gln Ala Tyr Gly Cys Asn Glu
1               5                   10

<210> SEQ ID NO 280
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 280

Met Glu Asn Thr Tyr Phe Gln Ala Tyr Gly Cys Asn Glu
1               5                   10

<210> SEQ ID NO 281
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 281

Gly Glu Asn Thr Tyr Phe Gln Ala Tyr Gly Cys Asn Glu
1               5                   10

<210> SEQ ID NO 282
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 282

Ala Asp Asn Thr Tyr Phe Gln Ala Tyr Gly Asn Asn Glu
1               5                   10

<210> SEQ ID NO 283
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 283

Val Asp Asn Thr Tyr Phe Gln Ala Tyr Gly Asn Asn Glu
1               5                   10

<210> SEQ ID NO 284
<211> LENGTH: 13
<212> TYPE: PRT
<213> ORGANISM: Artificial Sequence
<220> FEATURE:
<223> OTHER INFORMATION: artificial amino acid sequence

```
<400> SEQUENCE: 284

Ile Asp Asn Thr Tyr Phe Gln Ala Tyr Gly Asn Asn Glu
1               5                   10

<210> SEQ ID NO 285
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 285

Leu Asp Asn Thr Tyr Phe Gln Ala Tyr Gly Asn Asn Glu
1               5                   10

<210> SEQ ID NO 286
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 286

Met Asp Asn Thr Tyr Phe Gln Ala Tyr Gly Asn Asn Glu
1               5                   10

<210> SEQ ID NO 287
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 287

Gly Asp Asn Thr Tyr Phe Gln Ala Tyr Gly Asn Asn Glu
1               5                   10

<210> SEQ ID NO 288
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 288

Ala Glu Asn Thr Tyr Phe Gln Ala Tyr Gly Asn Asn Glu
1               5                   10

<210> SEQ ID NO 289
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 289

Val Glu Asn Thr Tyr Phe Gln Ala Tyr Gly Asn Asn Glu
1               5                   10

<210> SEQ ID NO 290
<211> LENGTH: 13
<212> TYPE: PRT
<213> ORGANISM: Artificial Sequence
<220> FEATURE:
<223> OTHER INFORMATION: artificial amino acid sequence
```

```
<400> SEQUENCE: 290

Ile Glu Asn Thr Tyr Phe Gln Ala Tyr Gly Asn Asn Glu
1               5                   10

<210> SEQ ID NO 291
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 291

Leu Glu Asn Thr Tyr Phe Gln Ala Tyr Gly Asn Asn Glu
1               5                   10

<210> SEQ ID NO 292
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 292

Met Glu Asn Thr Tyr Phe Gln Ala Tyr Gly Asn Asn Glu
1               5                   10

<210> SEQ ID NO 293
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 293

Gly Glu Asn Thr Tyr Phe Gln Ala Tyr Gly Asn Asn Glu
1               5                   10

<210> SEQ ID NO 294
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 294

Ala Glu Cys Thr Tyr Phe Gln Ala Tyr Gly Asn Asn Asp
1               5                   10

<210> SEQ ID NO 295
<211> LENGTH: 8
<212> TYPE: PRT
<213> ORGANISM: Artificial Sequence
<220> FEATURE:
<223> OTHER INFORMATION: artificial amino acid sequence

<400> SEQUENCE: 295

Gly Gly Gly Ser Leu Leu Gln Gly
1               5

<210> SEQ ID NO 296
<211> LENGTH: 21
<212> TYPE: DNA
<213> ORGANISM: Artificial Sequence
<220> FEATURE:
<223> OTHER INFORMATION: PCR primer
```

```
<400> SEQUENCE: 296
tggctgaacg gcaaagagta c                                         21

<210> SEQ ID NO 297
<211> LENGTH: 40
<212> TYPE: DNA
<213> ORGANISM: Artificial Sequence
<220> FEATURE:
<223> OTHER INFORMATION: PCR primer

<400> SEQUENCE: 297
cctgaaagta ggtgcactcg ccgccagggc tcagggacag                     40

<210> SEQ ID NO 298
<211> LENGTH: 50
<212> TYPE: DNA
<213> ORGANISM: Artificial Sequence
<220> FEATURE:
<223> OTHER INFORMATION: PCR primer

<400> SEQUENCE: 298
cgggggatcc tcattcggtg cagccgtagg cctgaaagta ggtgcactcg          50

<210> SEQ ID NO 299
<211> LENGTH: 39
<212> TYPE: DNA
<213> ORGANISM: Artificial Sequence
<220> FEATURE:
<223> OTHER INFORMATION: PCR primer

<400> SEQUENCE: 299
ctgaaagtag gtgttctcgc cgccagggct cagggacag                      39

<210> SEQ ID NO 300
<211> LENGTH: 50
<212> TYPE: DNA
<213> ORGANISM: Artificial Sequence
<220> FEATURE:
<223> OTHER INFORMATION: PCR primer

<400> SEQUENCE: 300
cgggggatcc tcattcggta ttgccgtagg cctgaaagta ggtgttctcg          50

<210> SEQ ID NO 301
<211> LENGTH: 39
<212> TYPE: DNA
<213> ORGANISM: Artificial Sequence
<220> FEATURE:
<223> OTHER INFORMATION: artificial nucleotide sequence
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (30)..(39)
<223> OTHER INFORMATION: n is a, c, g, or t

<400> SEQUENCE: 301
nnnnnnnnna cntayttyca rgcntayggn nnnnnnnnn                      39
```

```
<210> SEQ ID NO 302
<211> LENGTH: 5
<212> TYPE: PRT
<213> ORGANISM: Artificial Sequence
<220> FEATURE:
<223> OTHER INFORMATION: artificial amino acid sequence
<220> FEATURE:
<221> NAME/KEY: X
<222> LOCATION: (3)..(3)
<223> OTHER INFORMATION: X = D, E, A, N, Q, or K

<400> SEQUENCE: 302

Leu Pro Xaa Thr Gly
1               5

<210> SEQ ID NO 303
<211> LENGTH: 5
<212> TYPE: PRT
<213> ORGANISM: Artificial Sequence
<220> FEATURE:
<223> OTHER INFORMATION: artifical amino acid sequence
<220> FEATURE:
<221> NAME/KEY: MISC_FEATURE
<222> LOCATION: (5)..(5)
<223> OTHER INFORMATION: lysine covalently bound to biotin

<400> SEQUENCE: 303

Gly Gly Gly Tyr Lys
1               5
```

TRANSGLUTAMINE TAG FOR EFFICIENT SITE-SPECIFIC BIOCONJUGATION

CROSS REFERENCE TO RELATED APPLICATIONS

This application is a national stage filing under 35 U.S.C. 371 of International Application No. PCT/EP2016/001344, filed Aug. 4, 2016, which claims the benefit of European Patent Application No. 15180278.2, filed Aug. 7, 2015 each of which is incorporated herein by reference in its entirety.

FIELD OF THE INVENTION

The present invention pertains to the field of bioconjugation, in particular to the field of microbial transglutaminase-mediated bioconjugation and its use for the manufacture of bioconjugates, such as e.g. antibody-drug conjugates.

BACKGROUND

Protein modification with synthetic or naturally occurring molecules is a valuable technique to study protein function or to add additional properties to a protein. Bioconjugations involving natural or synthetic macromolecules, particularly proteins, emerged as a powerful tool to tailor their architecture and engineer functional properties (see e.g. Perez et al. Drug Discovery Today, 2014 Vol 19 (7):869-881). Protein modification or bioconjugation is typically done by either chemical linkage of a further molecule to the protein of interest or enzymatically.

Chemical strategies that are currently utilized for conjugation of biomolecules, make use of the fact that cysteine and lysine residues can be readily be modified. Cysteine residues can be alkylated by reacting them with α-haloketones or Michael acceptors, such as maleimide derivates. The modification of lysine residues is the oldest and most straightforward method for labeling proteins via the primary lysine amino groups. The 6-amino group of lysine within the protein of interest can be readily reacted with activated esters, sulfonyl chlorides, isocyanates and isothiocyanates to result in the corresponding amides, sulfonamides, ureas and thioureas (see e.g. Takaoka et al., Angew. Chem. Int. Ed. 2013, 52, 4088-4106). Although very efficient for bioconjugation these chemical approaches inevitably result in heterogenous mixtures. This effect becomes more pronounced in smaller molecules with fewer lysines, e.g. in antibody fragments lacking an Fc region compared to IgG type molecules. Further examples for bioconjugation include the conjugation of fluorescent proteins, dyes, or the tethering with functional molecules, e.g. PEGs, porphyrins, peptides, peptide nucleic acids, and drugs (Takaoka et al., Angew. Chem. Int. Ed. 2013, 52, 4088-4106).

The preparation of protein bioconjugates may involve varying levels of difficulty depending on the desired outcome. For example bioconjugation can range from the simple and non-specific attachment of polyethylene glycol (PEG) to serum albumin (Abuchowski et al. J. of Biological Chemistry (1977) Vol. 252 (11):3578-3581) to the very demanding preparation of homogenous antibody drug bioconjugates.

This challenge can be addressed, among other approaches, by applying enzyme-mediated conjugations. For example, WO 2014/001325 A1 discloses the use of sortase A for site-specific bioconjugation to Fc regions of an antibody. Sortase A (SrtA) is a bacterial integral membrane protein first described in Staphylococcus aureus. SrtA catalyzes a transpeptidation reaction anchoring proteins to the bacterial cell wall. Upon recognition of a sorting signal LPXTG, (X=D, E, A, N, Q, or K) a catalytic cysteine cleaves the peptide bond between residues T and G which results in the formation of a thioacyl intermediate. This thioacyl intermediate subsequently then can reacts with an amino-terminal glycine acting as a nucleophile. SrtA accepts N-terminal (oligo)glycine as a nucleophiles, creating a new peptide bond between two molecules. SrtA functions at physiological conditions and has been used for bioconjugation reactions to label proteins with e.g. biotin, or to functionalize a HER2-specific recombinant Fab with the plant cytotoxin gelonin (see e.g. Popp et al. (2011) Angew Chemie Int. Ed. 50: 5024-5032; Kornberger et al (2014) mAbs 6 (2): 354-366). Typically, target proteins are labeled carboxyterminally with the LPXTG motif followed by a purification tag such that the SrtA-mediated transpeptidation removes the purification tag and generates the labeled protein.

One of the major drawbacks in the use of SrtA in bioconjugation reactions is the high concentration of the enzyme that is required to catalyze the transpeptidase reaction. Attempts have been made to improve the reaction kinetics using SrtA molecular evolution which has resulted in an increase of the affinity of the enzyme to the LPXTG motif by about 140-fold (see e.g. Proc Natl Acad Sci USA. 2011 Jul. 12; 108(28): 11399-11404). Another disadvantage to the use of SrtA-mediated bioconjugation reactions is the reversibility of catalyzed reactions. Also here attempts have been made to overcome this limitation through the use of chemically modified SrtA substrates LPETGG-isoacyl-serine and LPETGG-isoacyl-homoserine, which can be irreversibly ligated to amino-terminal glycine-containing moieties via the deactivation of SrtA-excised peptide fragments throught the formation of diketopeperazines (see e.g. Liu et al. J. Org. Chem. 2014, 79, 487-492).

Another prominent enzyme-mediated bioconjugation approach involves the use of transglutaminases (TGases), in particular microbial transglutaminases (mTGases). TGases are a large family of enzymes detected in several organisms including mammals, invertebrates, plants and microorganisms. Transglutaminases are protein-glutamine γ-glutamyl-transferases (E.C. 2.3.2.13), which typically catalyze pH-dependent transamidation of glutamine residues to lysine residues. Most TGases appear to be promiscuous with respect to the lysine substrate and may even accept 5-aminopentyl groups as lysine surrogates to serve as the amine donor. However, the selectivity of TGases to recognize a glutamine residue as a substrate appear to be much more stringent in that for a glutamine residue to be accepted by TGases the residue has to be located in a flexible region of the protein (see e.g. Jeger et al. Angew. Chem Int. Ed. 2010, 49, 9995-9997; Fontana et al. Adv Drug Deliv Rev. 2008 Jan. 3; 60(1)13-28).

Transglutaminases are widely distributed in most tissues and body fluids and are thought to be involved in a variety of physiological functions. One example for a transglutaminase-mediated reaction is the termination of bleeding during blood coagulation by factor XIIIa, which is an activated form of plasma transglutaminase which catalyzes the cross-linking between fibrin molecules (see e.g. Griffin et al. Biochem. J. (2002) 368, 377-396). The biological function of bacterial transglutaminases, however, remains largely unknown. It has been speculated that the mTGase of *Streptomyces mobaraensis* cross-links inhibitory proteins during development of aerial hyphae and spores.

The transglutaminase from *S. mobaraensis* exhibits no significant homology to mammalian TGases and has a unique structure compared to human TG2 being the best characterized member of the human TGase family. In contrast to its mammalian orthologue mTG2 of *S. mobaraensis* is calcium-independent and has only a molecular weight of 37.9 kDa, which is only about half of the molecular weight of factor XIII-like TGases. mTG2 is also characterized by a higher reaction rate than its mammalian orthologue. Another aspect that has contributed to the widespread use of mTG2 is the fact that the enzyme can be easily produced in larger quantities as a recombinant protein which in conjunction with its biochemical properties has led to a wide use of mTG2 also in food industry (see e.g. Sommer at al. (2011) Protein Expression and Purification 77:9-19; Marx et al (2008) Enzyme and Microbial technology 42:568-575). Random mutagenesis of mTG2 has also been employed to increase the thermodynamic stability of the enzyme (see e.g. Journal of Biotechnology 136 (2008) 156-162). Notably, all mutations that have resulted in an increased stability of mTG2 at elevated temperatures are located within the amino-terminal region of the enzyme.

Microbial Transglutaminase mTG2 has also been used for site-specific and stoichiometric PEGylation of proteins such as α-lactalbumin, human growth hormone and interleukin-2 or for site-specific and stoichiometric modification of antibodies (see e.g. Jeger et al. Angew. Chem Int. Ed. 2010, 49, 9995-9997; Fontana et al. Adv Drug Deliv Rev. 2008 Jan. 3; 60(1):13-28). Overall, the number of reactive glutamines was found to be low in comparison to the total number of surface-exposed glutamines.

mTG2, when used to catalyze transglutamination on native, fully glycosylated monoclonal antibodies, was found to not recognize any glutamine residues in the respective monoclonal antibody as substrate. Only de- or aglycosylated antibodies were found to be recognized as substrates by mTG2. Interestingly, only one glutamine residue was found to serve as a acyl-glutamine substrate in the de- or aglycosylated antibodies (Q295). This strongly limits the use of mTG2 for site-specific bioconjugation of antibodies for the generation of antibody-drug conjugates, in particular for use in humans. Interestingly, when a Fc mutant (N297Q) antibody was used, this second glutamine residue was also found to be modified by mTG2 with the respective substrate (Fontana et al. Adv Drug Deliv Rev. 2008 Jan. 3; 60(1):13-28).

One of the best characterized proteins for mTG-mediated PEGylation is human growth hormone (hGH). For hGH, two glutamine residues were identified as major conjugation sites, namely Q40 and Q141. Mutagenesis of mTG resulted in an mTG variant with increased selectivity toward Q141. In another study, it was found that, for salmon calcitonin and human growth hormone, a change in the solvent which presumably results in a change in the secondary structure surrounding the reactive glutamine can be used to limit the conjugation to a single glutamine residue, and therefore increase selectivity.

In the case of human interleukin 2 (hIL-2), a single reactive glutamine (Gln74) was found and conjugated with 12 kDa PEG or galactose-terminated triantennary glycosides.

Artificial peptide sequences have been used in the past to further examine the substrate specificity of mTG2. For example, the sequence effects around the substrate Gln residue were first investigated in context of the heptapeptide substrate (GGGQGGG), where each glycine was individually substituted to several amino acids (Ohtsuka et al. Biosci., Biotechnol., Biochem. 64, 2608-13). It was found that hydrophobic residues at the N-terminus of the Gln accelerated the reaction relative to the GGGQGGG peptide (at the −3, −2, and −1 positions), however the overall reaction kinetics were low.

The preferred substrate sequence of mTG was also assessed using a phage-displayed peptide library utilizing a much larger library of about $10^{11}$ linear peptides. Most identified clones contained an aromatic amino acid (VV, F, or Y) at the −5 to −3 positions, an arginine or hydrophobic residue at the +1 or +2 positions, and hydrophobic residues at the −2 and −1 positions (see e.g. Sugimura et al., Archives of Biochemistry and Biophysics 477 (2008) 379-383).

The use of mTG2 for the generation of antibody-drug-conjugates requires the bioconjugation of a functional payload with a monoclonal antibody counterpart. In antibody-drug conjugates (ADCs) the antibody specifically directs the uptake and release of a highly potent toxin to a cancer cell, a technology which has attracted much attention in recent years as a novel and effective new treatment option for cancer patients.

Examples of ADCs which have received market approval include Kadcyla® (trastuzumab Emtansin) and Adcetris® (brentuximab vedotin) for the treatment of metastatic breast cancer and Hodkin lymphoma. These antibodies as well as other antibody candidates that are currently in clinical development have not been obtained by bioconjugation using e.g. mTG2, but rely on chemical conjugation methods for their production that result in heterogenous mixtures of antibodies with varying numbers of drug molecules attached to them (see e.g. Handbook of Therapeutic Antibodies, $2^{nd}$ edition, edited by S. Dübel and J. M. Reichert, John Wiley & Sons (2014), pp. 369).

It has been shown that heterogeneity of ADCs can negatively impact drug efficacy, in particular if significant fractions of the material are insufficiently conjugated: Insufficiently conjugated antibodies will compete with ADCs for target binding resulting in a reduced efficacy of the properly conjugated ADCs. Increased drug loading to antibodies can also negatively impact the efficacy of the ADC. Data have demonstrated that ADCs with high drug:antibody ratios are cleared more rapidly from the blood stream resulting in reduced efficacy (see e.g. Sanderson et al. Clin. Cancer Res. 2005; 11:843-52). Studies with anti-CD30 monoclonal antibody—auristatin E (MMAE) conjugates have shown that the ADCs with a antibody:drug stoichiometry of 1:2-1:4 are most effective, with a ratio of 1:4 being most preferable (see e.g. Hamblett et al. Clinical Cancer Research (2004) Vol. 10, 7063-7070).

WO 2013/092983, discloses methods of functionalization of immunoglobulins with drugs employing TGase. This approach, describes the method to obtain new site by directed mutagenesis to generate a Q-donor inside the heavy chain of the antibody. This empiric method needs to test high number of mutants as the rules which govern selection by TGases of glutamine residues for modification are still largely unknown. Consequently, using this method to develop new antibodies bearing Q-donor is time consuming and cost intensive.

WO 2012/059882 further discloses specific engineered polypeptide conjugates and methods of making such conjugates using transglutaminases.

WO 2015/097267 discloses peptide sequences which selectively react as glutamine donors with transglutaminase, such as mTG2 of *S. mobaraensis* which may be utilized for mTG2-mediated conjugation reactions.

Despite the studies on bioconjugation of proteins with mTG2 and exploration of new sequence motifs which may be utilized as glutamine donors for bioconjugation reactions, neither the sequences nor the structural environment of natural MTG substrate sites are known.

There is thus a need to expand the repertoire of substrates recognized by mTG2 for a more efficient production of bioconjugates, in particular for the manufacture of ADCs with a well defined antibody:drug stoichiometry

SUMMARY OF THE INVENTION

The present inventors have surprisingly found that a acyl glutamine-containing donor sequence derived from the dispase autolysis inducing protein of *Streptomyces mobaraensis* strain 40847 comprising at least the amino acid sequence TYFQAYG can be efficiently used in mTG2-mediated transglutamination reactions.

Accordingly, the present invention provides in a first embodiment a protein comprising at least one acyl glutamine-containing amino donor sequence, which is covalently linked via a γ-glutamyl-amide bond to an amino donor-comprising substrate, wherein the at least one acyl glutamine-containing amino acid donor sequence comprises the amino acid sequence according to SEQ ID NO: 1 (SEQ ID NO: 1 (TYFQAYG)).

According to one embodiment the amino donor-comprising substrate according to the present invention comprises at least an s-amino group, or at least one tripeptide having the sequence of GGG with a primary aminoterminal amino group.

In one embodiment the amino donor-comprising substrate according to the invention is a lysine residue, a lysine derivative, lysine drug-conjugate, a polypeptide comprising at least one lysine residue.

According to one embodiment the amino donor-comprising substrate according to any one of the above embodiments of the invention is covalently bound to a further molecule.

According to one embodiment the tripeptide GGG of the amino donor-comprising substrate is covalently bound via its carboxy terminus to a further molecule.

In one embodiment the further molecule according to the invention is one of a dye, radioisotope, drug, ribozyme, nanobody, enzyme, or linker.

In one embodiment the further molecule according to the invention is a linker, which is cleavable or non-cleavable.

According to one embodiment the linker according to the invention is coupled or covalently bound to a dye, radioisotope, or cytotoxin.

In a preferred embodiment, the protein of the invention according to any one of the above embodiments comprises an acyl glutamine-containing amino acid donor sequence, which comprises an amino acid sequence according to SEQ ID NO: 2 ($X_1X_2X_3$TYFQAYG $X_4X_5X_6$), wherein.
X1 is a hydrophobic amino acid,
X2 is a negatively charged amino acid,
X3 is C or N,
X4 is C or N,
X5 is one of an amino acid with a polar, uncharged side chains, and
X6 is a negatively charged amino acid.

In a preferred embodiment the acyl glutamine-containing amino acid donor sequence of the invention according to any one of the above embodiments comprises an amino acid sequence according to SEQ ID NO: 2, wherein
X1 is any one of A, V, I, L, M or G,
X2 is one of D or E,
X3 is C,
X4 is C or N,
X5, is S, T, or N,
X6 is one of D, or E.

According to a preferred embodiment the acyl glutamine-containing amino acid donor sequence of the invention comprises an amino acid sequence according to SEQ ID NO:2, wherein
X1 is any one of A, V, I, L, M or G,
X2 is one of D or E,
X3 is C,
X4 is C,
X5, is S, T, or N,
X6 is one of D, or E.

According to a more preferred embodiment the acyl glutamine-containing amino acid donor sequence of the invention comprises the amino acid sequence according to SEQ ID NO: 2, wherein
X1 is any one of A, V, I, L, M or G,
X2 is E,
X3 is C,
X4 is C,
X5 is T, and
X6 is E.

According to an even more preferred embodiment the acyl glutamine-containing amino acid donor sequence of the invention comprises an amino acid sequence according to SEQ ID NO: 90.

In one embodiment the protein according to the invention is one of an antibody, antigen-binding antibody fragment, Fc domain, enzyme, a non-immunoglobulin scaffold.

In one embodiment the protein according to the invention is a monoclonal antibody, bivalent antibody, VHH, Fab, F(ab)$_2$, or scFv.

According to a preferred embodiment the protein according to the invention is a human or humanized monoclonal antibody or fragment thereof.

In one aspect the present invention provides for a method of covalently coupling an amino donor comprising substrate of the invention to an acyl glutamine-containing amino acid donor comprising a polypeptide sequence according to SEQ ID NO:2, whereby the method comprises the step of:
contacting an amino donor-comprising substrate according to the invention and an acyl glutamine-containing amino acid donor according to the invention in the presence of transglutaminase, preferably mTG2, to obtain a protein of the invention according to any one of the above embodiments.

In one embodiment the acyl glutamine-containing amino acid donor of the inventive method is an antibody, antigen-binding antibody fragment, enzyme, or a non-immunoglobulin scaffold.

According to one embodiment, the amino donor-comprising substrate of the inventive method is coupled or covalently bound to a dye, drug, ribozyme, nanobody, enzyme, or linker.

According to one embodiment of the invention the linker is cleavable or non-cleavable and is coupled to a dye, radioisotope, or cytotoxin.

In one embodiment the present invention provides for a protein obtainable by the inventive method as disclosed herein.

In one embodiment the present invention provides for the use of a polypeptide sequence according to any one of SEQ ID NO: 2 in the inventive method according to any one of the embodiments as disclosed herein.

According to one embodiment the present invention provides for a protein comprising the polypeptide comprising the amino acid sequence according to SEQ ID NO:2.

In one embodiment the present invention provides for a polypeptide according to SEQ ID NO:2.

In one embodiment the present invention provides for a polynucleotide encoding a polypeptide sequence according to SEQ ID NO: 2 of the invention.

In one embodiment the present invention provides for a vector comprising the polynucleotide encoding the polypeptide sequence according to SEQ ID NO:2.

In one embodiment the present invention provides a host cell which comprises the polynucleotide of the invention or a vector according to the invention as disclosed herein.

In one embodiment the present invention provides an antibody or antigen-binding fragment thereof, bivalent antibody, or VHH antibody according to the invention which comprises at least one amino acid sequence according to SEQ ID NO:2.

Accordingly, the antibody or antigen-binding fragment thereof, bivalent antibody, or VHH antibody of the invention is humanized or human.

In a preferred embodiment the antibody or antigen-binding fragment thereof according to the invention as disclosed above is a humanized or human monoclonal antibody.

In a preferred embodiment the antibody of the invention as disclosed above is an IgG1, IgG2, IgG3, IgG4, or IgM type antibody.

In one embodiment the inventive antibody as disclosed above is covalently coupled to at least one linker as disclosed above according to the inventive method as disclosed above.

According to one embodiment the at least one linker of the monoclonal antibody of the invention is further coupled to a dye, radioisotope, or cytotoxin.

In a preferred embodiment the inventive monoclonal antibody as disclosed herein specifically binds to cancer cell surface antigens.

In a more preferred embodiment the monoclonal antibody of the invention as disclosed above is the monoclonal antibody c225 (cetuximab).

In a more preferred embodiment the antibody of the invention as disclosed herein is for use in the treatment of cancer, more preferably the inventive antibody as disclosed above is for use in the treatment of breast cancer, prostate cancer, ovarian cancer, cervical cancer, skin cancer, pancreatic cancer, preferably colorectal cancer, metastatic (mCRC), non-resectable liver metastases, Squamous Cell Carcinoma of the Head and Neck, Non-Small Cell Lung Cancer (NSCLC), Head and Neck Squamous Cell Carcinoma (HNSCC).

According to one embodiment the present invention provides for a composition comprising the inventive antibody and at least one further pharmaceutically active ingredient.

In one embodiment the present invention provides a pharmaceutical comprising the inventive antibody as disclosed herein or which comprises the composition according to the invention and at least one further ingredient.

In one embodiment the present invention pertains to a method of treating a subject in need thereof inflicted with cancer, wherein the treatment comprises administering to said patient a therapeutically effective amount of the pharmaceutical composition according to to the invention.

BRIEF DESCRIPTION OF DRAWINGS

FIG. 3: Binding of biotinylated cetuximab studied in cell assays and by flow cytometry. a) Cell binding assays of biotinylated cetuximab variants 9 and 10 compared to cetuximab wt using EGFR-positive EBC-1 cells and EGFRnegative CHO-K1 cells (+MTG rx., middle and lower panels). Cells were mounted using ProLong® Diamond Antifade Mountant with DAPI (blue) and biotinylation visualized by labelling with Streptavidin-AF488 (green). Cells were scanned using a confocal microscope. Merged pictures are shown with differential interference contrast (DIC). b) Flow cytometry of EGFR-positive EBC-1 cells incubated with biotinylated cetuximab variants 9. Cells bound to biotinylated cetuximab were fluorescence labelled by the addition of Streptavidin Alexa Fluor® 488 conjugate.

FIG. 10: (A) Peptides derived from trypsin digestion were analyzed by using the bioinformatics tool GPMAW. Peptides modified by either carbamidomethyl (CAM) at cysteine residues or monobiotinyl-cadaverine (MBC) at glutamine residues are underlined in cyan, peptides identified without modifications are underlined in magenta. (B) Statistical analysis of residue coverage indicating that a 56% coverage of the residues was achieved.

FIG. 11: SDS-PAGE gel analysis of cetuximab wild-type (wt) and variants 9 and 10 comparing antibodies with C-terminal lysine from the wild-type sequence of cetuximab (+K447) and antibodies tacking this C-terminal lysine (−K447). Intramolecular cross-linking catalyzed by MTG has been observed in preliminary experiments between the MTG-tags and the C-terminal Lys residue from the wild-type sequence of cetuximab (+K447). This cross-linkage could be completely abolished by omitting this lysine (−K447).

FIG. 15: Cytotoxic payloads with different primary amines used in transglutaminase-mediated conjugation reactions. (1) Monomethyl auristatin E (MMAE) with non-cleavable polyethylene glycol (PEG) linker and primary amino group, (2) Monomethyl auristatin E (MMAE) with cleavable valine-citrulline-p-aminobenzylcarbamate (vc-PABC) linker, PEG-spacer and primary amine, (3) Monomethyl auristatin E (MMAE) with cleavable valine-citrulline-p-aminobenzylcarbamate (vc-PABC) linker and aliphatic amino group, (4) Monomethyl auristatin F (MMAF) with cleavable valine-citrulline-p-aminobenzylcarbamate (vc-PABC) linker and aliphatic amino group.

SEQUENCE LISTING

Figure 1:
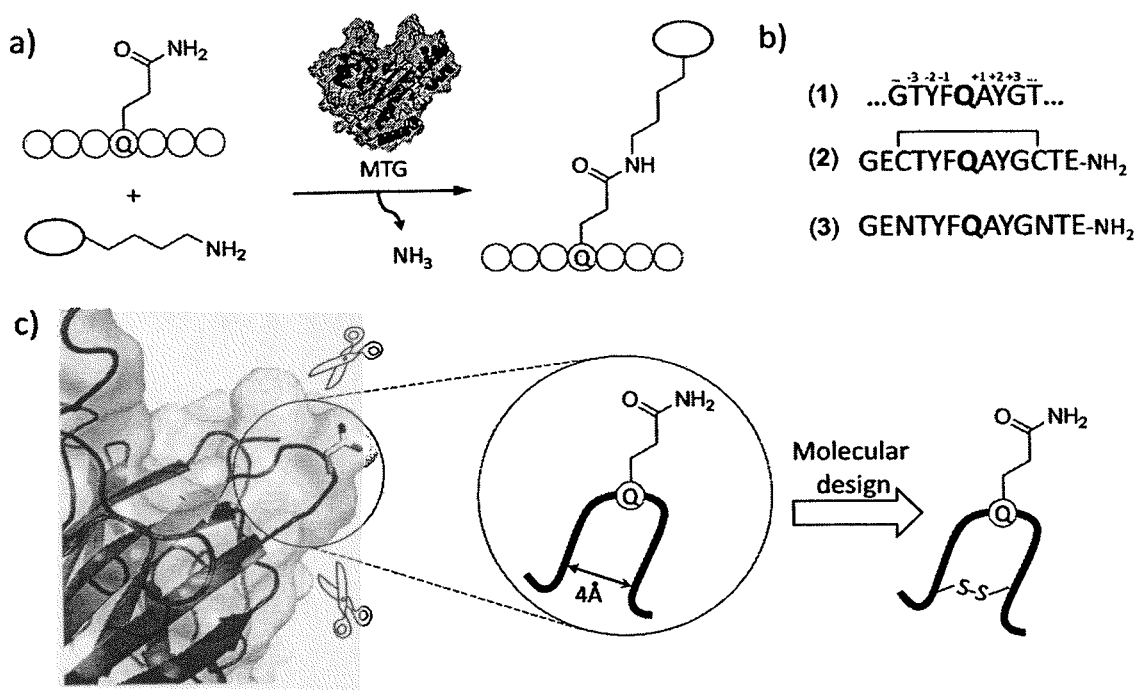
FIG. 1: a) Transglutaminase-mediated conjugation of glutamine (Q) with an amine-donor substrate. b) Amino acid sequence of a natural transglutaminase recognition sequence taken from the substrate protein DAIP (1) and engineered sequences (2) and (3) used in this study for conjugation. c) Schematic depiction of the design of an engineered transglutaminase recognition sequence (MTGtag) mimicking the functional Q298 loop in DAIP.
Figure 2:
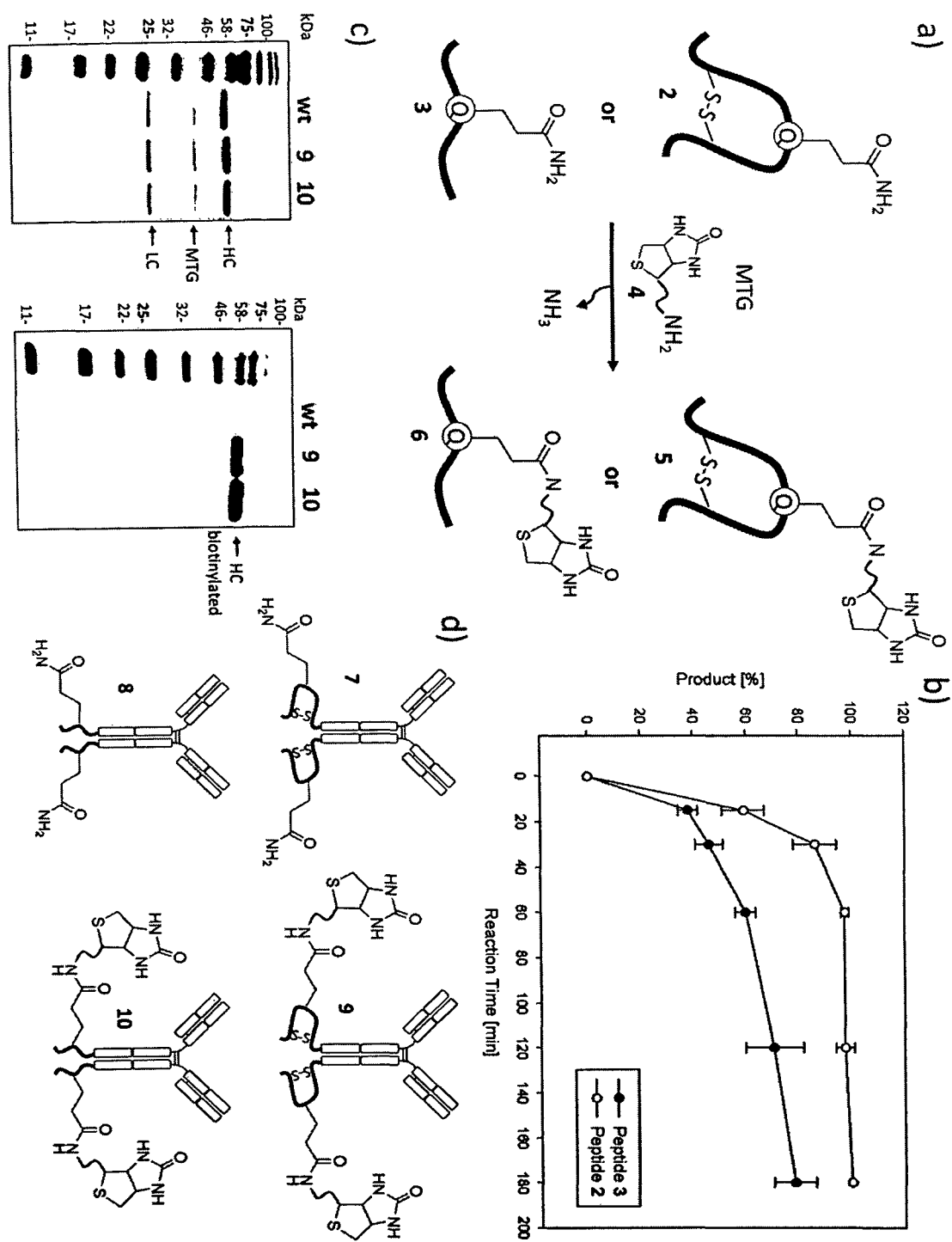
FIG. 2: MTG-mediated conjugation of engineered model peptides and full length monoclonal antibodies. a) Engineered model peptides 2 and 3 containing a transglutaminase recognition motif were biotinylated in MTG-catalyzed reaction with monobiotinylcadaverine (4, MBC). b) Biotinylation kinetics comparing conformationally constrained peptide 2 (○) (e.g. with an inventive peptide according to SEQ ID NO:4) with linear peptide 3 (●) (e.g. with inventive peptides according to SEQ ID NO:3 or SEQ ID NO:5). Error bars representing standard deviation were calculated from triplicates. SDS-PAGE gel and western blot analysis of biotinylated cetuximab variants with C-terminal MTG-tags (9: with inventive MTG-tag according to SEQ ID NO:90, 10: with inventive MTG-tag according to SEQ ID NO:246). Biotinylation was visualized using streptavidin-alkaline phosphatase conjugate and NBT/BCIP (right panel). d) Overview of cetuximab variants with C-terminal MTG-tags used for MTG-promoted biotinylation (7 and 8) and the respective conjugated antibodies (9 and 10).

Sequences according to SEQ ID NO:1-SEQ ID NO:294 are according to the invention and may be used in in accordance with the embodiments of the present invention:

| | |
|---|---|
| TYFQAYG | SEQ ID NO: 1 |
| $X_1X_2X_3$ TYFQAYG $X_4X_5X_6$ | SEQ ID NO: 2 |
| $X_1X_2C$ TYFQAYG $NX_5X_6$ | SEQ ID NO: 3 |
| $X_3X_2C$ TYFQAYG $CX_5X_6$ | SEQ ID NO: 4 |
| $X_3X_2N$ TYFQAYG $NX_5X_6$ | SEQ ID NO: 5 |
| $X_3X_2N$ TYFQAYG $CX_5X_6$ | SEQ ID NO: 6 |
| ADC TYFQAYG CSD | SEQ ID NO: 7 |
| VDC TYFQAYG CD | SEQ ID NO: 8 |
| IDC TYFQAYG CSD | SEQ ID NO: 9 |
| LDC TYFQAYG CSD | SEQ ID NO: 10 |
| MDC TYFQAYG CSD | SEQ ID NO: 11 |
| GDC TYFQAYG CSD | SEQ ID NO: 12 |
| AEC TYFQAYG CSD | SEQ ID NO: 13 |
| VEC TYFQAYG CSD | SEQ ID NO: 14 |
| IEC TYFQAYG CSD | SEQ ID NO: 15 |
| LEC TYFQAYG CSD | SEQ ID NO: 16 |
| MEC TYFQAYG CSD | SEQ ID NO: 17 |
| GEC TYFQAYG CSD | SEQ ID NO: 18 |
| ADC TYFQAYG NSD | SEQ ID NO: 19 |
| VDC TYFQAYG NSD | SEQ ID NO: 20 |
| IDC TYFQAYG NSD | SEQ ID NO: 21 |
| LDC TYFQAYG NSD | SEQ ID NO: 22 |
| MDC TYFQAYG NSD | SEQ ID NO: 23 |
| GDC TYFQAYG NSD | SEQ ID NO: 24 |
| AEC TYFQAYG NSD | SEQ ID NO: 25 |
| VEC TYFQAYG NSD | SEQ ID NO: 26 |
| IEC TYFQAYG NSD | SEQ ID NO: 27 |
| LEC TYFQAYG NSD | SEQ ID NO: 28 |
| MEC TYFQAYG NSD | SEQ ID NO: 29 |
| GEC TYFQAYG NSD | SEQ ID NO: 30 |
| ADC TYFQAYG CSE | SEQ ID NO: 31 |
| VDC TYFQAYG CSE | SEQ ID NO: 32 |
| IDC TYFQAYG CSE | SEQ ID NO: 33 |
| LDC TYFQAYG CSE | SEQ ID NO: 34 |
| MDC TYFQAYG CSE | SEQ ID NO: 35 |
| GDC TYFQAYG CSE | SEQ ID NO: 36 |
| AEC TYFQAYG CSE | SEQ ID NO: 37 |
| VEC TYFQAYG CSE | SEQ ID NO: 38 |
| IEC TYFQAYG CSE | SEQ ID NO: 39 |
| LEC TYFQAYG CSE | SEQ ID NO: 40 |

| SEQ ID | Sequence | SEQ ID | Sequence |
|---|---|---|---|
| SEQ ID NO: 41 | MEC TYFQAYG CSE | SEQ ID NO: 81 | IDC TYFQAYG CTE |
| SEQ ID NO: 42 | GEC TYFQAYG CSE | SEQ ID NO: 82 | LDC TYFQAYG CTE |
| SEQ ID NO: 43 | ADC TYFQAYG NSE | SEQ ID NO: 83 | MDC TYFQAYG CTE |
| SEQ ID NO: 44 | VDC TYFQAYG NSE | SEQ ID NO: 84 | GDC TYFQAYG CTE |
| SEQ ID NO: 45 | IDC TYFQAYG NSE | SEQ ID NO: 85 | AEC TYFQAYG CTE |
| SEQ ID NO: 46 | LDC TYFQAYG NSE | SEQ ID NO: 86 | VEC TYFQAYG CTE |
| SEQ ID NO: 47 | MDC TYFQAYG NSE | SEQ ID NO: 87 | IEC TYFQAYG CTE |
| SEQ ID NO: 48 | GDC TYFQAYG NSE | SEQ ID NO: 88 | LEC TYFQAYG CTE |
| SEQ ID NO: 49 | AEC TYFQAYG NSE | SEQ ID NO: 89 | MEC TYFQAYG CTE |
| SEQ ID NO: 50 | VEC TYFQAYG NSE | SEQ ID NO: 90 | GEC TYFQAYG CTE |
| SEQ ID NO: 51 | IEC TYFQAYG NSE | SEQ ID NO: 91 | ADC TYFQAYG NTE |
| SEQ ID NO: 52 | LEC TYFQAYG NSE | SEQ ID NO: 92 | VDC TYFQAYG NTE |
| SEQ ID NO: 53 | MEC TYFQAYG NSE | SEQ ID NO: 93 | IDC TYFQAYG NTE |
| SEQ ID NO: 54 | GEC TYFQAYG NSE | SEQ ID NO: 94 | LDC TYFQAYG NTE |
| SEQ ID NO: 55 | ADC TYFQAYG CTD | SEQ ID NO: 95 | MDC TYFQAYG NTE |
| SEQ ID NO: 56 | VDC TYFQAYG CTD | SEQ ID NO: 96 | GDC TYFQAYG NTE |
| SEQ ID NO: 57 | IDC TYFQAYG CTD | SEQ ID NO: 97 | AEC TYFQAYG NTE |
| SEQ ID NO: 58 | LDC TYFQAYG CTD | SEQ ID NO: 98 | VEC TYFQAYG NTE |
| SEQ ID NO: 59 | MDC TYFQAYG CTD | SEQ ID NO: 99 | IEC TYFQAYG NTE |
| SEQ ID NO: 60 | GDC TYFQAYG CTD | SEQ ID NO: 100 | LEC TYFQAYG NTE |
| SEQ ID NO: 61 | AEC TYFQAYG CTD | SEQ ID NO: 101 | MEC TYFQAYG NTE |
| SEQ ID NO: 62 | VEC TYFQAYG CTD | SEQ ID NO: 102 | GEC TYFQAYG NTE |
| SEQ ID NO: 63 | IEC TYFQAYG CTD | SEQ ID NO: 103 | ADC TYFQAYG CND |
| SEQ ID NO: 64 | LEC TYFQAYG CTD | SEQ ID NO: 104 | VDC TYFQAYG CND |
| SEQ ID NO: 65 | MEC TYFQAYG CTD | SEQ ID NO: 105 | IDC TYFQAYG CND |
| SEQ ID NO: 66 | GEC TYFQAYG CID | SEQ ID NO: 106 | LDC TYFQAYG CND |
| SEQ ID NO: 67 | ADC TYFQAYG NTD | SEQ ID NO: 107 | MDC TYFQAYG CND |
| SEQ ID NO: 68 | VDC TYFQAYG NTD | SEQ ID NO: 108 | GDC TYFQAYG CND |
| SEQ ID NO: 69 | IDC TYFQAYG NTD | SEQ ID NO: 109 | AEC TYFQAYG CND |
| SEQ ID NO: 70 | LDC TYFQAYG NTD | SEQ ID NO: 110 | VEC TYFQAYG CND |
| SEQ ID NO: 71 | MDC TYFQAYG NTD | SEQ ID NO: 111 | IEC TYFQAYG CND |
| SEQ ID NO: 72 | GDC TYFQAYG NTD | SEQ ID NO: 112 | LEC TYFQAYG CND |
| SEQ ID NO: 73 | AEC TYFQAYG NTD | SEQ ID NO: 113 | MEC TYFQAYG CND |
| SEQ ID NO: 74 | VEC TYFQAYG NTD | SEQ ID NO: 114 | GEC TYFQAYG CND |
| SEQ ID NO: 75 | IEC TYFQAYG NTD | SEQ ID NO: 115 | ADC TYFQAYG NND |
| SEQ ID NO: 76 | LEC TYFQAYG NTD | SEQ ID NO: 116 | VDC TYFQAYG NND |
| SEQ ID NO: 77 | MEC TYFQAYG NTD | SEQ ID NO: 117 | IDC TYFQAYG NND |
| SEQ ID NO: 78 | GEC TYFQAYG NTD | SEQ ID NO: 118 | LDC TYFQAYG NND |
| SEQ ID NO: 79 | ADC TYFQAYG CTE | SEQ ID NO: 119 | MDC TYFQAYG NND |
| SEQ ID NO: 80 | VDC TYFQAYG CTE | SEQ ID NO: 120 | GDC TYFQAYG NND |

| | |
|---|---|
| AEC TYFQAYG NND | SEQ ID NO: 121 |
| VEC TYFQAYG NND | SEQ ID NO: 122 |
| IEC TYFQAYG NND | SEQ ID NO: 123 |
| LEC TYFQAYG NND | SEQ ID NO: 124 |
| MEC TYFQAYG NND | SEQ ID NO: 125 |
| GEC TYFQAYG NND | SEQ ID NO: 126 |
| ADC TYFQAYG CNE | SEQ ID NO: 127 |
| VDC TYFQAYG CNE | SEQ ID NO: 128 |
| IDC TYFQAYG CNE | SEQ ID NO: 129 |
| LDC TYFQAYG CNE | SEQ ID NO: 130 |
| MDC TYFQAYG CNE | SEQ ID NO: 131 |
| GDC TYFQAYG CNE | SEQ ID NO: 132 |
| AEC TYFQAYG CNE | SEQ ID NO: 133 |
| VEC TYFQAYG CNE | SEQ ID NO: 134 |
| IEC TYFQAYG CNE | SEQ ID NO: 135 |
| LEC TYFQAYG CNE | SEQ ID NO: 136 |
| MEC TYFQAYG CNE | SEQ ID NO: 137 |
| GEC TYFQAYG CNE | SEQ ID NO: 138 |
| ADC TYFQAYG NNE | SEQ ID NO: 139 |
| VDC TYFQAYG NNE | SEQ ID NO: 140 |
| IDC TYFQAYG NNE | SEQ ID NO: 141 |
| LDC TYFQAYG NNE | SEQ ID NO: 142 |
| MDC TYFQAYG NNE | SEQ ID NO: 143 |
| GDC TYFQAYG NNE | SEQ ID NO: 144 |
| AEC TYFQAYG NNE | SEQ ID NO: 145 |
| VEC TYFQAYG NNE | SEQ ID NO: 146 |
| IEC TYFQAYG NNE | SEQ ID NO: 147 |
| LEC TYFQAYG NNE | SEQ ID NO: 148 |
| MEC TYFQAYG NNE | SEQ ID NO: 149 |
| GEC TYFQAYG NNE | SEQ ID NO: 150 |
| ADN TYFQAYG CSD | SEQ ID NO: 151 |
| VDN TYFQAYG CSD | SEQ ID NO: 152 |
| IDN TYFQAYG CSD | SEQ ID NO: 153 |
| LDN TYFQAYG CSD | SEQ ID NO: 154 |
| MDN TYFQAYG CSD | SEQ ID NO: 155 |
| GDN TYFQAYG CSD | SEQ ID NO: 156 |
| AEN TYFQAYG CSD | SEQ ID NO: 157 |
| VEN TYFQAYG CSD | SEQ ID NO: 158 |
| IEN TYFQAYG CSD | SEQ ID NO: 159 |
| LEN TYFQAYG CSD | SEQ ID NO: 160 |
| MEN TYFQAYG CSD | SEQ ID NO: 161 |
| GEN TYFQAYG CSD | SEQ ID NO: 162 |
| ADN TYFQAYG NSD | SEQ ID NO: 163 |
| VDN TYFQAYG NSD | SEQ ID NO: 164 |
| IDN TYFQAYG NSD | SEQ ID NO: 165 |
| LDN TYFQAYG NSD | SEQ ID NO: 166 |
| MDN TYFQAYG NSD | SEQ ID NO: 167 |
| GDN TYFQAYG NSD | SEQ ID NO: 168 |
| AEN TYFQAYG NSD | SEQ ID NO: 169 |
| VEN TYFQAYG NSD | SEQ ID NO: 170 |
| IEN TYFQAYG NSD | SEQ ID NO: 171 |
| LEN TYFQAYG NSD | SEQ ID NO: 172 |
| MEN TYFQAYG NSD | SEQ ID NO: 173 |
| GEN TYFQAYG NSD | SEQ ID NO: 174 |
| ADN TYFQAYG CSE | SEQ ID NO: 175 |
| VDN TYFQAYG CSE | SEQ ID NO: 176 |
| IDN TYFQAYG CSE | SEQ ID NO: 177 |
| LDN TYFQAYG CSE | SEQ ID NO: 178 |
| MDN TYFQAYG CSE | SEQ ID NO: 179 |
| GDN TYFQAYG CSE | SEQ ID NO: 180 |
| AEN TYFQAYG CSE | SEQ ID NO: 181 |
| VEN TYFQAYG CSE | SEQ ID NO: 182 |
| IEN TYFQAYG CSE | SEQ ID NO: 183 |
| LEN TYFQAYG CSE | SEQ ID NO: 184 |
| MEN TYFQAYG CSE | SEQ ID NO: 185 |
| GEN TYFQAYG CSE | SEQ ID NO: 186 |
| ADN TYFQAYG NSE | SEQ ID NO: 187 |
| VDN TYFQAYG NSE | SEQ ID NO: 188 |
| IDN TYFQAYG NSE | SEQ ID NO: 189 |
| LDN TYFQAYG NSE | SEQ ID NO: 190 |
| MDN TYFQAYG NSE | SEQ ID NO: 191 |
| GDN TYFQAYG NSE | SEQ ID NO: 192 |
| AEN TYFQAYG NSE | SEQ ID NO: 193 |
| VEN TYFQAYG NSE | SEQ ID NO: 194 |
| IEN TYFQAYG NSE | SEQ ID NO: 195 |
| LEN TYFQAYG NSE | SEQ ID NO: 196 |
| MEN TYFQAYG NSE | SEQ ID NO: 197 |
| GEN TYFQAYG NSE | SEQ ID NO: 198 |
| AND TYFQAYG CTD | SEQ ID NO: 199 |
| VDN TYFQAYG CTD | SEQ ID NO: 200 |

-continued

IDN TYFQAYG CTD SEQ ID NO: 201
LDN TYFQAYG CTD SEQ ID NO: 202
MDN TYFQAYG CTD SEQ ID NO: 203
GDN TYFQAYG CTD SEQ ID NO: 204
AEN TYFQAYG CTD SEQ ID NO: 205
VEN TYFQAYG CTD SEQ ID NO: 206
IEN TYFQAYG CTD SEQ ID NO: 207
LEN TYFQAYG CTD SEQ ID NO: 208
MEN TYFQAYG CTD SEQ ID NO: 209
GEN TYFQAYG CTD SEQ ID NO: 210
ADN TYFQAYG NTD SEQ ID NO: 211
VDN TYFQAYG NTD SEQ ID NO: 212
IDN TYFQAYG NTD SEQ ID NO: 213
LDN TYFQAYG NTD SEQ ID NO: 214
MDN TYFQAYG NTD SEQ ID NO: 215
GDN TYFQAYG NTD SEQ ID NO: 216
AEN TYFQAYG NTD SEQ ID NO: 217
VEN TYFQAYG NTD SEQ ID NO: 218
IEN TYFQAYG NTD SEQ ID NO: 219
LEN TYFQAYG NTD SEQ ID NO: 220
MEN TYFQAYG NTD SEQ ID NO: 221
GEN TYFQAYG NTD SEQ ID NO: 222
ADN TYFQAYG CTE SEQ ID NO: 223
VDN TYFQAYG CTE SEQ ID NO: 224
IDN TYFQAYG CTE SEQ ID NO: 225
LDN TYFQAYG CTE SEQ ID NO: 226
MDN TYFQAYG CTE SEQ ID NO: 227
GDN TYFQAYG CTE SEQ ID NO: 228
AEN TYFQAYG CTE SEQ ID NO: 229
VEN TYFQAYG CTE SEQ ID NO: 230
IEN TYFQAYG CTE SEQ ID NO: 231
LEN TYFQAYG CTE SEQ ID NO: 232
MEN TYFQAYG CTE SEQ ID NO: 233
GEN TYFQAYG CTE SEQ ID NO: 234
ADN TYFQAYG NTE SEQ ID NO: 235
VDN TYFQAYG NTE SEQ ID NO: 236
IDN TYFQAYG NTE SEQ ID NO: 237
LDN TYFQAYG NTE SEQ ID NO: 238
MDN TYFQAYG NTE SEQ ID NO: 239
GDN TYFQAYG NTE SEQ ID NO: 240
AEN TYFQAYG NTE SEQ ID NO: 241
VEN TYFQAYG NTE SEQ ID NO: 242
IEN TYFQAYG NTE SEQ ID NO: 243
LEN TYFQAYG NTE SEQ ID NO: 244
MEN TYFQAYG NTE SEQ ID NO: 245
GEN TYFQAYG NTE SEQ ID NO: 246
ADN TYFQAYG CND SEQ ID NO: 247
VDN TYFQAYG CND SEQ ID NO: 248
IDN TYFQAYG CND SEQ ID NO: 249
LDN TYFQAYG CND SEQ ID NO: 250
MDN TYFQAYG CND SEQ ID NO: 251
GDN TYFQAYG CND SEQ ID NO: 252
AEN TYFQAYG CND SEQ ID NO: 253
VEN TYFQAYG CND SEQ ID NO: 254
IEN TYFQAYG CND SEQ ID NO: 255
LEN TYFQAYG CND SEQ ID NO: 256
MEN TYFQAYG CND SEQ ID NO: 257
GEN TYFQAYG CND SEQ ID NO: 258
ADN TYFQAYG NND SEQ ID NO: 259
VDN TYFQAYG NND SEQ ID NO: 260
IDN TYFQAYG NND SEQ ID NO: 261
um TYFQAYG NND SEQ ID NO: 262
MDN TYFQAYG NND SEQ ID NO: 263
GDN TYFQAYG NND SEQ ID NO: 264
AEN TYFQAYG NND SEQ ID NO: 265
VEN TYFQAYG NND SEQ ID NO: 266
IEN TYFQAYG NND SEQ ID NO: 267
LEN TYFQAYG NND SEQ ID NO: 268
MEN TYFQAYG NND SEQ ID NO: 269
GEN TYFQAYG NND SEQ ID NO: 270
ADN TYFQAYG CNE SEQ ID NO: 271
VDN TYFQAYG CNE SEQ ID NO: 272
IDN TYFQAYG CNE SEQ ID NO: 273
LDN TYFQAYG CNE SEQ ID NO: 274
MDN TYFQAYG CNE SEQ ID NO: 275
GDN TYFQAYG CNE SEQ ID NO: 276
AEN TYFQAYG CNE SEQ ID NO: 277
VEN TYFQAYG CNE SEQ ID NO: 278
IEN TYFQAYG CNE SEQ ID NO: 279
LEN TYFQAYG CNE SEQ ID NO: 280

```
                                    SEQ ID NO: 281
MEN TYFQAYG CNE

SEQ ID NO: 282
GEN TYFQAYG CNE

SEQ ID NO: 283
ADN TYFQAYG NNE

SEQ ID NO: 284
VDN TYFQAYG NNE

SEQ ID NO: 285
IDN TYFQAYG NNE

SEQ ID NO: 286
LDN TYFQAYG NNE

SEQ ID NO: 287
MDN TYFQAYG NNE

SEQ ID NO: 288
GDN TYFQAYG NNE

SEQ ID NO: 289
AEN TYFQAYG NNE

SEQ ID NO: 290
VEN TYFQAYG NNE

SEQ ID NO: 291
IEN TYFQAYG NNE

SEQ ID NO: 292
LEN TYFQAYG NNE

SEQ ID NO: 293
MEN TYFQAYG NNE

SEQ ID NO: 294
GEN TYFQAYG NNE

SEQ ID NO: 295
GGGSLLQG

SEQ ID NO: 296
5'-TGGCTGAACGGCAAAGAGTAC

SEQ ID NO: 297
5'-CCTGAAAGTAGGTGCACTCGCCGCCAGGGCTCAGGGACAG

SEQ ID NO: 298
5'-CGGGGGATCCTCATTCGGTGCAGCCGTAGGCCTGAAAGTAGGTGC
ACTCG

SEQ ID NO: 299
5'-CTGAAAGTAGGTGTTCTCGCCGCCAGGGCTCAGGGACAG

SEQ ID NO: 300
5'-CGGGGGATCCTCATTCGGTATTGCCGTAGGCCTGAAAGTAGGTGT
TCTCG

SEQ ID NO: 301
5'-NNN$_1$NNN$_2$NNN$_3$ACNTAYTTYCARGCNTAYGGNNNN$_4$NNN$_5$NNN$_6$

SEQ ID NO: 302
LPXTG, with X = D, E, A, N, Q, or K

SEQ ID NO: 303
GGGYK
```

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention wilt be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of".

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The described objectives are solved by the present invention, preferably by the subject matter of the appended claims. More preferably, the present invention is solved according to a first embodiment by a protein which comprises at least one acyl glutamine-containing amino acid donor sequence covalently linked via a y-glutamyl-amid bond to an amino donor-comprising substrate, wherein the at least one acyl glutamine-containing amino acid donor sequence comprises at least the amino acid sequence according to SEQ ID NO: 1 (SEQ ID NO: 1 (TYFQAYG)). Accordingly, the present invention provides for a protein which comprises at least one, e.g. 1, 2, 3, 4, 5, 6, 7, or 8, preferably 1-6 (e.g. 1, 2, 3, 4, 5, 6), more preferably 1-4 (e.g. 1, 2, 3, 4) acyl glutamine-containing amino acid donor sequences, whereby the at least one acyl glutamine-containing amino acid donor sequence according to the invention is covalently linked via a γ-glutamyl-amid bond to an amino donor-comprising substrate and wherein the at least one acyl glutamine-containing amino acid donor sequence comprises at least the amino acid sequence according to SEQ ID NO: 1 (TYFQAYG). The term "acyl glutamine-containing amino acid donor sequence" according to the invention pertains to an amino acid sequence, which is at least 7 amino acids in length, e.g. at least 7, 8, 9, 10, 11, 12, 13, 14, or 15 amino acids in length and which comprises at least the amino acid sequence according to SEQ ID NO:1. The acyl glutamine-containing amino acid donor sequence according to the invention may e.g. in addition the amino acid sequence according to SEQ ID NO: 1 comprise natural or non-natural amino acids, or naturally occurring amino acid derivates. For example, the inventive acyl glutamine-containing amino acid donor sequence may comprise 1, 2, 3, 4, 5, 6, 7 or 8 non-natural amino acids, or naturally occurring amino acid derivates.

For example, non-natural amino acids which may be comprised in the acyl glutamine-containing amino acid donor sequence of the invention may include azidonorleucine, 3-(1-naphthyl)alanine, 3-(2-naphthyl)alanine, p-ethynyl-phenylalanine, p-propargyl-oxy-phenylalanine, m-ethynyl-phenylalanine, 6-ethynyl-tryptophan, 5-ethynyl-tryptophan, (R)-2-amino-3-(4-ethynyl-1 H-pyrrol-3-yl) propanoic acid, p-bromophenylalanine, p-idiophenylalanine, p-azidophenylalanine, 3-(6-chloroindolyl)alanine, 3-(6-bromoindoyl)alanine, 3-(5-bromoindolyl)alanine, azidohomoalanine, and p-chlorophenylalanine. For example, naturally occurring amino acid derivatives may include 4-hydroxyproline, ε-N,N,N-trimethyllysine, 3-methylhistidine, 5-hydroxylysine, O-phosphoserine, γ-carboxyglutamate, ε-N-acetyllysine, ω-N-methylarginine, N-acetylserine, N,N,N-trimethylalanine.

The term "γ-glutamyl-amid bond" according to the invention refers to an isopeptide bond, e.g. an amide bond, which does not form part of the peptide-bond backbone of the respective polypeptide or protein, which is formed between the gamma-carbon of the glutamyl residue of the inventive acyl glutamine-containing amino acid donor sequence and a primary (1°) amine of the amino donor-comprising substrate according to the invention.

According to one embodiment the amino donor-comprising substrate according to the invention comprises at least an s-amino group or at least one tripeptide having the sequence of GGG with a primary aminoterminal amino group. For example, the amino donor-comprising substrate according to the invention may be lysine, such as L-lysine, or a lysine derivative, or structural mimetics thereof, such as e.g. diaminobutyric acid (DAB), 2,3-diaminopropanoic acid, (2S)-2,8-diaminooctanoic acid, ornithinem, thialysine, 1,5-diaminopentane, or N-(biotinyl)cadaverine. The amino donor-comprising substrate according to the invention may e.g. also comprise lysine derivatives which have been coupled to a dye (e.g. TAMRA, or Alexa-Fluor® dyes), or other molecule such as e.g. biotin. The amino donor-comprising substrate according to the invention may e.g. also be a GGG tripeptide, which e.g. may further be coupled to a dye or molecule, such as TAMRA-ethylenediamine or biotin, e.g.:

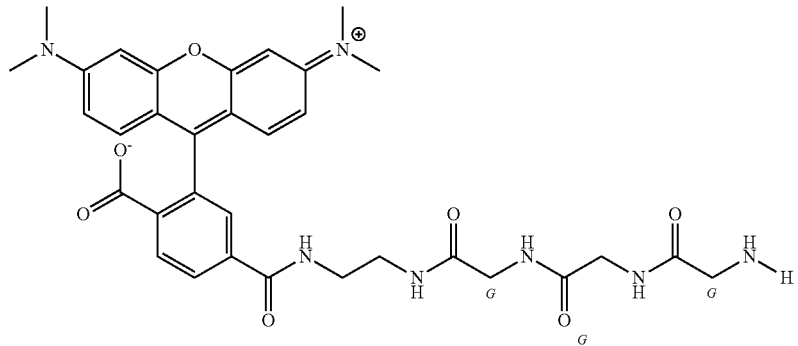 [SMILES: CN(C)c1ccc2c(-c3cc(C(=O)NCCNC(=O)CNC(=O)CNC(=O)CN)ccc3C(=O)[O-])c3ccc(=[N+](C)C)cc-3oc2c1]

or e.g.:

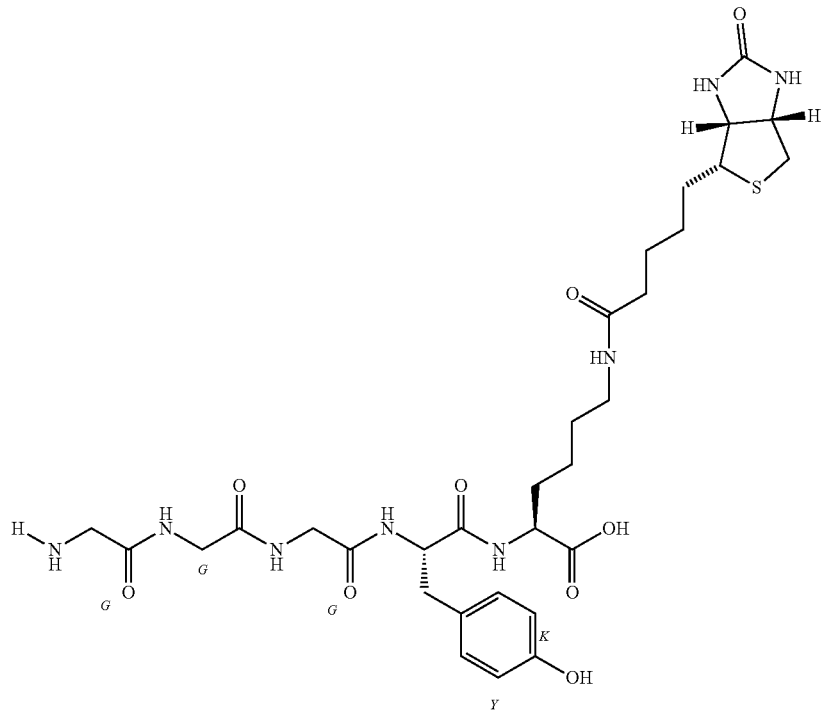

In one embodiment the amino donor-comprising substrate according to the invention may e.g. also include polypeptides comprising at least one lysine residue.

According to one embodiment the amino donor-comprising substrate of the invention is covalently bound to a further molecule. For example, the amino donor-comprising substrate according to the invention as disclosed above, such as the tripeptide as disclosed above, may be covalently bound to a further molecule, preferably via its carboxyterminus. For example, the further molecule may be covalently bound via a peptide bond, isopeptide bond, or any other covalent bond, such as e.g. a disulfide bond.

According to one embodiment the further molecule according to the invention as disclosed above is one of a dye, radioisotope, drug, ribozyme, nanobody, enzyme, or linker. For example, a dye which may be covalently bound to the amino donor-comprising substrate according to the invention may be a fluorophore. Accordingly, the amino donor-comprising substrate according to the invention may be covalently bound to a fluorophore. The term "fluorophore" as used in the present invention refers to a chemical compound, which when excited by exposure to a particular wavelength of light, emits light at a different wavelength, e.g. fluorophores that may be covalently bound to the amino donor-comprising substrate according to the invention may include 1,8-ANS, 4-methylumbelliferone, 7-amino-4-methylcoumarin, 7-hydroxy-4-methylcoumarin, Acridine, Alexa Fluor 350™, Alexa Fluor 405™, AMCA, AMCA-X, ATTO Rho6G, ATTO Rho11, ATTO Rho12, ATTO Rho13, ATTO Rho14, ATTO Rho101, Pacific Blue, Alexa Fluor 430™, Alexa Fluor 480™, Alexa Fluor 488™, BODIPY 492/515, Alexa Fluor 532™, Alexa Fluor 546™, Alexa Fluor 555™, Alexa Fluor 594™, BODIPY 505/515, Cy2, cyQUANT GR, FITC, Fluo-3, Fluo-4, GFP (EGFP), mHoneydew, Oregon Green™ 488, Oregon Green 514, EYFP, DsRed, DsRed2, dTomato, Cy3.5, Phycoerythrin (PE), Rhodamine Red, mTangerine, mStrawberry, mOrange, mBanana, Tetramethylrhodamine (TRITC), R-Phycoerythrin, ROX, DyLight 594, Calcium Crimson, Alexa Fluor 594™, Alexa Fluor 610™, Texas Red, mCherry, mKate, Alexa Fluor 660™, Alexa Fluor 680™ allophycocyanin, DRAQ-5, carboxynaphthofluorescein, C7, DyLight 750, Cellvue NIR780, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxy coumarin, Naphtho fluorescein, PyMPO, 5-carboxy-4',5'-dichloro-2', 7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, or La Jolla blue dye. Fluorophores according to the invention may e.g. also include quantum dots. The term quantum dot as used in the present invention refers to a single spherical nanocrystal of semiconductor material where the radius of the nanocrystal is less than or equal to the size of the exciton Bohr radius for that semiconductor material (the value for the exciton Bohr radius can be calculated from data found in handbooks containing information on semiconductor properties, such as the CRC Handbook of Chemistry and Physics, 83rd ed., Lide, David R. (Editor), CRC Press, Boca Raton, Fla. (2002)). Quantum dots are known in the art, as they are described in references, such as Weller, Angew. Chem. Int. Ed. Engl. 32: 41-53 (1993), Alivisatos, J. Phys. Chem. 100: 13226-13239 (1996), and Alivisatos, Science 271: 933-937 (1996). Quantum dots may e.g. be from about 1 nm to about 1000 nm diameter, e.g. 10 nm, 20 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, or 500 nm, preferably at least about 2 nm to about 50 nm, more preferably QDs are at least about 2 nm to about 20 nm in diameter (for example about 2, 3, 4, 5, 6, 7, 8, 9, 10, 11, 12, 13, 14, 15, 16, 17, 18, 19, or 20 nm). ODs are characterized by their substantially uniform nanometer size, frequently exhibiting approximately a 10% to 15% polydispersion or range in size. A QD is capable of emitting electromagnetic radiation upon excitation (i.e., the QD is photoluminescent) and includes a "core" of one or more first semiconductor materials, and may be surrounded by a "shell" of a second semiconductor material. A QD core surrounded by a semiconductor shell is referred to as a "core/shell" QD. The surrounding "shell" material will preferably have a bandgap energy that is larger than the bandgap energy of the core material and may be chosen to have an atomic spacing close to that of the "core" substrate. The core and/or the shell can be a semiconductor material including, but not limited to, those of the groups II-VI (ZnS, ZnSe, ZnTe, US, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, PbS, PbSe, and an alloy or a mixture thereof. Preferred shell materials include ZnS. Quantum dots may be coupled to the inventive linker, enzyme, or protein by any method known in the art such as e.g. the methods disclosed in Nanotechnology. 2011 Dec. 9; 22(49):494006; Colloids and Surfaces B: Biointerfaces 84 (2011) 360-368.

According to one embodiment the amino donor-comprising substrate of the invention may be covalently bound to a radioisotope such as e.g. $^{47}Ca$, $^{14}C$, $^{137}Cs$, $^{157}Cr$, $^{57}Co$, $^{60}Co$, $^{67}Cu$, $^{67}Ga$, $^{123}I$, $^{125}I$, $^{129}I$, $^{131}I$, $^{32}P$, $^{75}Se$, $^{85}Sr$, $^{35}S$, $^{201}Th$, $^{3}H$, preferably, the radioisotopes are incorporated into a further molecule, such as e.g. a chelator. Typical chelators that may e.g. be used as a further molecule covalently bound to the amino donor-comprising substrate of the invention are DPTA, EDTA (Ethylenediamine-tetraacetic acid), EGTA (Ethyleneglycol-O,O'-bis(2-aminoethyl)-N,N,N',N'-tetraacetic acid, NTA (Nitrilotriacetic acid), HEDTA (N-(2-Hydroxyethyl)-ethylenediamine-N,N',N'-triacetic acid), DTPA (2-[Bis[2-[bis(carboxymethyl)amino]-ethyl]amino] acetic acid), or DOTA (1,4,7,10-tetraazacyclo-dodecane-1, 4,7,10-tetraacetic acid).

For example, in one embodiment the amino donor-comprising substrate according to the invention may be covalently bound to a drug. The term "drug" as used in the present invention refers to any chemical compound or molecule which interferes with the physiological function of a cell, e.g. a cancer or tumor cell. Drugs which may be linked to the amino donor-comprising substrate according to the invention may include cytostatic agents, or cytotoxic agents. For example, cytostatic agents that may be used for covalent coupling to the amino donor-comprising substrate according to the invention include alkylating agents, antimetabolites, antibiotics, mitotic inhibitors, hormones, or hormone antagonists. Alkylating agents may e.g. include Busulfan (Myleran), Carboplatin (Paraplatin), Chlorambucil, Cisplatin, Cyclophosphamide (Cytoxan), Dacarbazine (DTIC- Dome), Estramustine Phosphate, Ifosphamide, Mechlorethamine (Nitrogen Mustard), Melphalan (Phenylalanine Mustard), Procarbazine, Thiotepa, Uracil Mustard, antimetabolites may e.g. include Cladribine, Cytarabine (Cytosine Arabinoside), Floxuridine (FUDR, 5-Fluorodeoxyuridine), Fludarabine, 5-Fluorouracil (5FU), Gemcitabine, Hydroxyurea, 6-Mercaptopurine (6MP), Methotrexate (Amethopterin), 6-Thioguanine, Pentostatin, Pibobroman, Tegafur, Trimetrexate, Glucuronate, antibiotics may e.g. include Aclarubicin, Bleomycin, Dactinomycin (Actinomycin D), Daunorubicin, Doxorubicin (Adriamycin), Epirubicin, Idarubicin, Mitomycin C, Mitoxantrone, Plicamycin (Mithramycin), or mitotic inhibitors may e.g. include Etoposide (VP-16, VePesid), Teniposide (VM-26, Vumon), Vinblastine, Vincristine, Vindesine, hormones, or hormone antagonists which may e.g. be used include Buserelin, Conjugate Equine Estrogen (Premarin), Cortisone, Chlorotriansene (Tace), Dexamethasone (Decadron), Diethylstilbestrol (DES), Ethinyl Estradiol (Estinyl), Fluoxymesterone (Halotestin), Flutamide, Goserelin Acetate (Zoladex), Hydroxyprogesterone Caproate (Delalutin), Leuprolide, Medroxyprogesterone Acetate (Provera), Megestrol Acetate (Megace), Prednisone, Tamoxifen (Nolvadex), Testolactone (Teslac), Testosterone. Cytostatic or antineoplastic compounds such as those disclosed above are known in prior art and may e.g. be found in D. S. Fischer & T. M. Knobf (1989), The cancer chemotherapy handbook (3rd ed.). Chicago: Year Book Medical and Association of Community Cancer Centers (Spring, 1992), Compendia-based drug bulletin, Rockville, Md.

For example, in one embodiment the amino donor-comprising substrate according to the invention may be covalently bound to an enzyme, such as L-Asparaginase.

According to one embodiment the amino donor-comprising substrate of the invention may e.g. be covalently bound to a ribozyme or nanobody. The term "ribozyme" as used in the present invention refers to an enzymatically active RNA molecule having trans-splicing activity and self-splicing activity. For the purpose of the present invention, the ribozyme can serve to inhibit the activity of the cancer-specific gene by a trans-splicing reaction, thereby exhibiting a selective anticancer effect. Any ribozyme may be used in the present invention, as long as it can inactivate a cancer-specific gene and activate the cancer therapeutic gene.

In one embodiment the amino donor-comprising substrate of the invention may e.g. be covalently bound to a nanobody. As used herein, the term "nanobody" refers to an antibody comprising a small single variable domain such as e.g. VHH of antibodies obtained from camelids and dromedaries, e.g. *Camelus baclrianus* and *Calelus dromaderius* including new world members such as llama species (*Lama paccos, Lama glama* and *Lama vicugna*). Antibodies from the species have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals (see e.g. W094/04678, Hamers-Casterman C, Nature 363: 446-448; Harmsen (2007) Appl Microb Biotechnol 77: 13-22).

According to one embodiment the amino donor-comprising substrate of the invention may e.g. be covalently bound to a linker. The term "linker" or "linker peptide" refers to a synthetic or artificial amino acid sequence that connects or links two molecules, such as e.g. two polypeptide sequences that link two polypeptide domains, or e.g. a protein and a cytostatic drug, or toxin. The term "synthetic" or "artificial" as used in the present invention refers to amino acid sequences that are not naturally occurring.

According to one embodiment the linker which is covalently bound to the amino donor-comprising substrate of the invention is cleavable or non-cleavable. The term "cleavable" as used in the present invention refers to linkers which may be cleaved by proteases, acids, or by reduction of a disulfide body (e.g. glutathione-mediated or glutathione sensitive). For example, cleavable linkers may comprise valine-citrulline linkers, hydrazone linkers, or disulfide linkers. Non-cleavable linkers which may e.g. be covalently bound to the amino donor-comprising substrate of the invention comprise maleimidocaproyl linker to MMAF (mc-MMAF), N-maleimidomethylcyclohexane-1-carboxylate (MCC), or mercapto-acetamidocaproyl linkers.

According to one embodiment the linker according to the invention is coupled or covalently bound to a dye, radioisotope, or cytotoxin. Accordingly, the linker according to the invention which is covalently bound to the amino donor-comprising substrate of the invention may be e.g. coupled or covalently bound to a dye, radioisotope, or cytotoxin. The term "coupled" as used for the linker according to the invention refers to the fact that the dye, radioisotope or cytoxin is non-covalently attached to the linker molecule according to the invention, e.g. via ionic, or hydrophobic interactions. For example, the linker may comprise streptavidin and the dye, radioisotope or cytotoxin may be covalently bound to biotin. For example, in case of radioisotopes, the radioisotope may be chelated to one of the chelators as disclosed above, which may be covalently bound to biotin. Alternatively, the radioisotope may e.g. be incorporated into the biotin, e.g. [8,9-3H]biotin (see e.g. Robinson et al., J Biol Chem. 1983 May 25; 258(10):6660-4.).

Preferably, the linker may e.g. be covalently bound to a cytotoxin, which may e.g. also be referred to as "payloads" (see e.g. Perez et al. Drug Discovery Today Vol 19 (7), July 2014). Cytotoxins which are suited for covalent attachment to linker molecules include those e.g. disclosed above and may be grouped into two main classes: The first class includes cytotoxins which disrupt microtubule assembly and the second class cytotoxins which target DNA structure. Accordingly, cytotoxins which may e.g. be covalently bound to the linker according to the invention include doxorubicin, calicheamicin, auristatin, maytansine duocarmycin and analogs thereof, α-amanitin, tubulysin and analogs thereof. Methods for covalently attaching cytotoxins to linkers are known in the art and may e.g. be done according to the method disclosed in Mol. Pharmaceutics 2015, 12, 1813-1835. Accordingly, the amino donor-comprising substrate of the invention which is coupled to a cleavable or non-cleavable linker as disclosed above and which are further coupled to a cytotoxin as disclosed above, may e.g. be used in transglutaminase-mediated bioconjugation reactions, preferably, the bioconjugation reaction is catalyzed by mTG2. The bioconjugation reaction may e.g. include at least one acyl glutamine-containing amino acid donor sequence substrate according to the invention as disclosed above comprising at least the amino acid sequence according to SEQ ID NO:1 (TYFQAYG) and the amino donor-comprising substrate of the invention as disclosed above in the presence of mTG2 under conditions which allow the mTG2 catalyzed reaction.

According to one embodiment the acyl glutamine-containing amino acid donor sequence of the invention comprises an amino acid sequence according to SEQ ID NO: 2 ($X_1X_2X_3$TYFQAYG $X_4X_5X_6$), wherein $X_1$ is a hydrophobic amino acid,
$X_2$ is a negatively charged amino acid,
$X_3$ is C or N,
$X_4$ is C or N,
$X_5$ is one of an amino acid with a polar, uncharged side chains, and $X_6$ is a negatively charged amino acid.

Accordingly, in the acyl glutamine-containing amino acid donor sequence of the invention $X_1$ may comprise any one of the amino acids A, I, L, M, F, W, Y, V, $X_2$ may comprise the amino acids D, E, $X_3$, $X_4$ may be one of C or N, $X_5$ may be one of S, T, N or Q and $X_6$ may be one of D, or E. Accordingly, the acyl glutamine-containing amino acid donor sequence of the invention may comprise an amino acid sequence according to any one of SEQ ID NO:1-SEQ ID NO:294, e.g. the acyl glutamine-containing amino acid donor sequence of the invention may comprise any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294.

According to one embodiment in the acyl glutamine-containing amino acid donor sequence of the invention $X_1$ may comprise any one of the amino acids A, V, I, L, M or G, $X_2$ may comprise the amino acids D, E, $X_3$ may be C, $X_4$ may be C or N, $X_5$ may be one of S, T, or N and $X_6$ may be one of D, or E. Accordingly, the acyl glutamine-containing amino acid donor sequence of the invention may comprise an amino acid sequence according to any one of SEQ ID NO:7, SEQ ID NO:8, SEQ ID NO:9, SEQ ID NO:10, SEQ ID NO:11, SEQ ID NO:19, SEQ ID NO:20, SEQ ID NO:21, SEQ ID NO:22, SEQ ID NO:23, SEQ ID NO:67, SEQ ID NO:68, SEQ ID NO:69, SEQ ID NO:70, SEQ ID NO:71, SEQ ID NO:115, SEQ ID NO:116, SEQ ID NO:117, SEQ ID NO:118, SEQ ID NO:119, SEQ ID NO:139, SEQ ID NO:140, SEQ ID NO:141, SEQ ID NO:142, SEQ ID NO:143, SEQ ID NO:55, SEQ ID NO:56, SEQ ID NO:57, SEQ ID NO:58, SEQ ID NO:59, SEQ ID NO:103, SEQ ID NO:104, SEQ ID NO:105, SEQ ID NO:106, SEQ ID NO:107, SEQ ID NO:127, SEQ ID NO:128, SEQ ID NO:129, SEQ ID NO:130, SEQ ID NO:131, SEQ ID NO:13, SEQ ID NO:14, SEQ ID NO:15, SEQ ID NO:16, SEQ ID NO:17, SEQ ID NO:18, SEQ ID NO:85, SEQ ID NO:86, SEQ ID NO:87, SEQ ID NO:88, SEQ ID NO:89, SEQ ID NO:90, SEQ ID NO:109, SEQ ID NO:110, SEQ ID NO:111, SEQ ID NO:112, SEQ ID NO:113, SEQ ID NO:114, SEQ ID NO:133, SEQ ID NO:134, SEQ ID NO:135, SEQ ID NO:136, SEQ ID NO:137, SEQ ID NO:138, SEQ ID NO:25, SEQ ID NO:26, SEQ ID NO:27, SEQ ID NO:28, SEQ ID NO:29, SEQ ID NO:30, SEQ ID NO:73, SEQ ID NO:74, SEQ ID NO:75, SEQ ID NO:76, SEQ ID NO:77, SEQ ID NO:78, SEQ ID NO:121, SEQ ID NO:122, SEQ ID NO:123, SEQ ID NO:124, SEQ ID NO:125, SEQ ID NO:126, SEQ ID NO:145, SEQ ID NO:146, SEQ ID NO:147, SEQ ID NO:148, SEQ ID NO:149, SEQ ID NO:150.

According to a preferred embodiment the acyl glutamine-containing amino acid donor sequence of the invention comprises an amino acid sequence according to SEQ ID NO:4 ($X_1X_2C$ TYFQAYG $CX_5X_6$) in which both $X_3$ and $X_4$ are C such that a disulfide bond may be formed between the two cysteine residues X3 and X4 which will form a loop-like structure, with amino residues TYFQAG forming the loop-like structure. In the inventive acyl glutamine-containing amino acid donor sequence $X_1$ may be any one of the amino acids A, V, I, L, M or G, $X_2$ may be D, or E, $X_3$ and $X_4$ are both C, $X_5$ may be one of S, T or N and $X_6$ may be one of the amino acids D, or E. Accordingly, the acyl glutamine-containing amino acid donor sequence of the invention may comprise an amino acid sequence according to any one of SEQ ID NO:7, SEQ ID NO:8, SEQ ID NO:9, SEQ ID NO:10, SEQ ID NO:11, SEQ ID NO:55, SEQ ID NO:56, SEQ ID NO:57, SEQ ID NO:58, SEQ ID NO:59, SEQ ID NO:103, SEQ ID NO:104, SEQ ID NO:105, SEQ ID NO:106, SEQ ID NO:107, SEQ ID NO:31, SEQ ID NO:32, SEQ ID NO:33, SEQ ID NO:34, SEQ ID NO:35, SEQ ID NO:36, SEQ ID NO:79, SEQ ID NO:80, SEQ ID NO:81, SEQ ID NO:82, SEQ ID NO:83, SEQ ID NO:84, SEQ ID NO:127, SEQ ID NO:128, SEQ ID NO:129, SEQ ID NO:130, SEQ ID NO:131, SEQ ID NO:13, SEQ ID NO:14, SEQ ID NO:15, SEQ ID NO:16, SEQ ID NO:17, SEQ ID NO:18, SEQ ID NO:61, SEQ ID NO:62, SEQ ID NO:63, SEQ ID NO:64, SEQ ID NO:65, SEQ ID NO:66, SEQ ID NO:109, SEQ ID NO:110, SEQ ID NO:111, SEQ ID NO:112, SEQ ID NO:113, SEQ ID NO:114, SEQ ID NO:37, SEQ ID NO:38, SEQ ID NO:39, SEQ ID NO:40, SEQ ID NO:41, SEQ ID NO:42, SEQ ID NO:85, SEQ ID NO:86, SEQ ID NO:87, SEQ ID NO:88, SEQ ID NO:89, SEQ ID NO:90, SEQ ID NO:133, SEQ ID NO:134, SEQ ID NO:135, SEQ ID NO:136, SEQ ID NO:137, SEQ ID NO:138.

The peptides of the invention may be synthesized according to any known method in the art, e.g. according to the methods disclosed in Atherton, E.; Sheppard, R. C. (1989). Solid Phase peptide synthesis: a practical approach. Oxford, England: IRL Press. ISBN 0-19-963067-4, or Stewart, J. M.; Young, J. D. (1984). *Solid phase peptide synthesis* (2nd ed.), ISBN 0-935940-03-0). Peptides may e.g. also be synthesized on an AmphiSpheres 40 RAM resin (Agilent, 0.27 mmol/g) by microwave-assisted Fmoc-SPPS using a Liberty Blue™ Microwave Peptide Synthesizer at a 0.1 mmol scale. Activation of the respective carboxyfunctional amino acid may e.g. be performed by Oxyma/N,N'-Diisopropylcarbodiimide (DIC). Deprotection of the aminoterminal Fmoc-group may e.g. be done using 20% piperidine in DMF in the presence of Oxyma. During the synthesis cycles all amino acids may e.g. be heated to 90° C. (cysteines to 50° C.). Peptides may then e.g. cleaved from the resin by a standard cleavage cocktail of 94% TFA, 2% triethylsilane, 2% anisole, 2% $H_2O$. For example, upon synthesis of the acyl glutamine-containing amino acid donor peptide according to SEQ ID NO:4, under non-oxidative synthesis and cleavage conditions, such as e.g. in the presence of dithiothreitol (DTT) in a concentration of e.g. from about 1 mM to about 50 mM, or from about 10 mM to about 40 mM. Disulfide bridge formation between residues $X_3$ and $X_4$ may be achieved under oxidizing conditions, e.g. 1 mg ml$^{-1}$ in 100 mM $(NH_4)_2CO_3$ aq. pH 8.4, whereby the oxidation reaction may be monitored by RP-HPLC.

In a more preferred embodiment in the acyl glutamine-containing amino acid donor sequence of the invention $X_1$ may be any one of amino acids A, V, I, L, M or G, $X_2$ is E, $X_3$, $X_4$ are both C, $X_5$ is T and $X_6$ is E. Accordingly, the acyl glutamine-containing amino acid donor sequence of the invention may comprise any one of SEQ ID NO:85, SEQ ID NO:86, SEQ ID NO:87, SEQ ID NO:88, SEQ ID NO:89, or SEQ ID NO:90.

According to a more preferred embodiment, in the acyl glutamine-containing amino acid donor sequence of the invention comprises the amino acid sequence according to SEQ ID NO:90 (GECTYFQAYGCTE).

The acyl glutamine-containing amino acid donor sequence according to the invention as disclosed above may e.g. be covalently bound to a protein of interest, such as e.g. enzymes or antibodies. For example, polynucleotides encoding the acyl glutamine-containing amino acid donor sequence of the invention may be added to cDNA constructs encoding light or heavy chains of antibodies by way of polymerase chain reaction (PCR). For example, SOE-PCR may be used according to the principle disclosed in PCR Methods Appl. 1993 May; 2(4):301-4, or e.g. in Critical Reviews in Oral Biology and Medicine, 4(314):581-590 (1993).

In one embodiment the protein comprising the acyl glutamine-containing amino acid donor sequence according to the invention as disclosed above may be an antibody, antigen-binding antibody fragment, Fc domain, enzyme, a non-immunoglobulin scaffold. Accordingly, the acyl glutamine-containing amino acid donor sequence of the invention may be covalently bound to an antibody, antigen-binding fragment, Fc domain, enzyme, a non-immunoglobulin scaffold.

For example, the protein according to the invention comprising the inventive acyl glutamine-containing amino acid donor sequence may be an antibody, whereby the term "antibody" refers to an immunoglobulin molecule capable of specific binding to a target, such as a carbohydrate, polynucleotide, lipid, polypeptide, etc., through at least one antigen recognition site, located in the variable region of the immunoglobulin molecule. As used in the present invention, the term "antibody" encompasses not only intact polyclonal or monoclonal antibodies, but also, unless otherwise specified, any antigen binding fragment thereof that competes with the intact antibody for specific binding, fusion proteins comprising an antigen binding portion, any other modified configuration of the immunoglobulin molecule that comprises an antigen recognition site, antibody compositions with polyepitopic specificity, multispecific antibodies (e.g., bispecific antibodies).

The term "monoclonal antibody" as used for the protein according to the invention refers to antibodies displaying a single binding specificity and indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma (e.g. murine or human) method first described by Köhler et at., Nature, 256:495 (1975), or may be made by recombinant DNA methods (see, e.g., U.S. Pat. No. 4,816, 567). A "monoclonal antibody" may also be isolated from phage antibody libraries using the techniques described in Clackson et at., Nature, 352:624-628 (1991) and Marks et at., J. Mol. Biol., 222:581-597 (1991).

The term "human monoclonal antibodies" as used for the protein according to the invention refers to monoclonal antibodies, which have variable and constant regions derived from human germline immunoglobulin sequences. The term "humanized" as used in the context of the present invention preferably refers to a monoclonal antibody in which the amino acid sequence is essentially identical to that of a human variant, despite the non-human origin of some of its complementarity determining region (CDR) segments responsible for the ability of the antibody to bind to its target antigen. The term "chimeric monoclonal antibody" as used in the present invention refers to a monoclonal antibody in which murine Fab fragments are spliced to human Fc.

In one embodiment the protein according to the invention as disclosed above is an antigen-binding fragment. The term "antigen binding fragment" as used for the inventive protein refers to, for example, Fab, Fab', F(ab')$_2$, Fd, Fv, domain antibodies, also referred to as "nanobodies" (dAbs, or VHH, e.g., shark and camelid antibodies, see e.g. mAbs (2015) 7:1, 15-25; Current Opinion in Structural Biology 2015, 32:1-8), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. A "bispecific antibody" as used according to the invention is an antibody that can bind two different target molecules, "bivalent antibody" as according to the invention is an antibody that can bind two different sites of one target molecule. The term "scFv" as used in the present invention refers to a molecule comprising an antibody heavy chain variable domain (or region; VH) and an antibody light chain variable domain (or region; VL) connected by a linker, and lacks constant domains. For example, the inventive protein may be a nanobody which comprise the acyl glutamine-containing amino acid donor sequence according to the invention, e.g. fused to the carboxyterminus of the nanobody. The nanobody according to the invention may then e.g. be used in a mTG2-mediated bioconjugation, whereby the amino donor-comprising substrate may e.g. be further coupled to a linker-cytotoxin as disclosed above, or may e.g. be further coupled to a radioisotope, or dye as disclosed above. The nanobodies of the invention may e.g. be used for cancer treatment, or imaging purposes. For example, nanobodies of the invention coupled to $^{68}$Ga which specifically bind EGFR, or HER2, may be used for Pet imaging to detect or image EGFR or HER2 expressing tumors. The term "specific binding" or any grammatical variation thereof refers to the ability of the inventive antibody, antigen-binding fragment (e.g. Fab, Fab', F(ab')$_2$, Fd, Fv), monoclonal antibody, single-chain antibody (scFv) or nanobody to bind to bind to its respective target (e.g. EGFR, or HER2) with an $K_D$ of at least about $1\times10^{-6}$, e.g. $1\times10^{-6}$ M, $1\times10^{-6}$ M, $1\times10^{-8}$ M, $1\times10^{-9}$ M, $1\times10^{-10}$ M, $1\times10^{-11}$ M, $1\times10^{-12}$ M, $1\times10^{-13}$ M, $1\times10^{-4}$ M, $1\times10^{-15}$ M, preferably between $1\times10^{-10}$ M and $1\times10^{-15}$ M, more preferably between about $1\times10^{-12}$ M to about $1\times10^{-19}$ M.

The term "immunoglobulin" (Ig) as used in the present invention may be used interchangeably with the term "antibody". The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four CH domains for p and s isotypes. Each L chain has at the N-terminus, a variable domain (VL) followed by a constant domain at its other end. The VL is aligned with the VH and the CL is aligned with the first constant domain of the heavy chain ($C_{H1}$). Particular amino acid residues are believed to form an interface between the light chain and heavy chain variable domains. The pairing of a VH and VL together forms a single antigen-binding site. For the structure and properties of the different classes of antibodies, see e.g., Basic and Clinical Immunology, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2A, IgG2B, IgG3, IgG4, IgA1 and Igκ1 IgG comprises the major class as it normally exists as the second most abundant protein found in plasma. In immunoglobulin fusion proteins, Fc domains of the IgG1 subclass are often used as the immunoglobulin moiety, because IgG1 has the longest serum half-life of any of the serum proteins. The Fc moiety may, e.g., also comprise Fc variants such as those disclosed in WO 02/094852 (e.g. Fc amino acid sequence with variants Fc-488, Fc4, Fc5, Fe6, Fc7, and Fc8 as disclosed therein) to reduce effector function of the Fc moeity.

For example, the protein according to the invention may be a fusion protein comprising the acyl glutamine-containing amino acid donor sequence according to the invention and a Fc domain to extend its serum half-life, whereby the acyl glutamine-containing amino acid donor sequence according to the invention is fused to the carboxyterminus of the Fc moiety. The terminal lysine (K) residue may e.g. be removed in Fc moieties e.g. in IgG-type antibodies, or in Fc-fusion proteins, by PCR-based site-directed mutagenesis to avoid intermolecular crosslinking. PCR-based site-directed mutagenesis may e.g. be done according to the method disclosed in Nucleic Acids Res. 1989 Aug. 25; 17(16):6545-51, Biotechniques. 1993 October; 15(4):700-4, Nucl. Acids Res., 32:e115, 2004 For example, primer pairs which may be used for the site-directed mutagenesis may e.g. also be selected according to the web-based automated tool available at: http://bioinformatics.org/primerx. Alternatively, the corresponding cDNAs which encode the protein according to the invention lacking a terminal lysine residue may be obtained by custom gene synthesis (see e.g. Nature 432, 1050-1054 (23 Dec. 2004); Nucleic Acids Res. 2007 April; 35(8): e61.; ACS Synth. Biol. 3, 97-106 (2014); Nat.

Methods 6, 343-345 (2009); Nucleic Acids Res. 40, e55 (2012); Proc. Natl. Acad. Sci. USA 105, 20404-20409 (2008)).

In one embodiment the protein according to the invention is a non-immunoglobulin scaffold comprising the inventive acyl glutamine-containing amino acid donor sequence. The term non-immunoglobulin scaffold as used for the protein according to the invention refers to affinity proteins that are not based on Ig molecules. Non-immunoglobulin scaffold proteins include e.g. those disclosed in Nature Biotechnology 23, 1257-1268, 2005, Trends Biotechnol. 2015 July; 33(7):408-18. For example, the protein according to the invention may be an albumin binding domain, phytocystaton protein (Adhiron), adnectin, Z-domain of S. aureus protein A, γ-B-crystallin (affilin), stefin A, DNA-binding protein Sac7a, alphabodym lipocalins (anticalins), or homologs of β-catenin (e.g. armadillo protein). For example, the protein according to the invention as disclosed herein may comprise the inventive acyl glutamine-containing amino acid donor sequence, whereby the inventive acyl glutamine-containing amino acid donor sequence may be present at the aminoterminus or at the carboxyterminus of the protein according to the invention. A determining factor in positioning the acyl glutamine-containing amino acid donor sequence of the invention to the amino- or carboxyterminus of the inventive protein as disclosed above is whether or not it will interfere with the intended use of the protein. For example, in case the protein according to the invention is an antibody, e.g. a monoclonal antibody, carboxyterminal fusion proteins with the inventive acyl glutamine-containing amino acid donor sequence are preferred, whereby the acyl glutamine-containing amino acid donor sequence according to SEQ ID NO:2 may be fused to the light chain, or heavy chain, or both heavy and light chain, thereby providing an monoclonal antibody comprising 2 (e.g. on both light chains (LCs), or on both heavy chains (HCs)) or 4 acyl glutamine-containing amino acid donor sequences according to the invention.

In one embodiment the present invention provides for a method of covalently coupling an amino donor-comprising substrate according to the invention as disclosed above to a acyl glutamine-containing amino acid donor of the invention which comprises a polypeptide sequence according to SEQ ID NO:2, whereby the method comprises the step of:

Contacting the amino donor-comprising substrate according to the invention and the acyl glutamine-containing amino acid donor according to the invention in the presence of transglutaminase, preferably mTG2, to obtain the inventive protein as disclosed above. Accordingly, in the inventive method the amino donor-comprising substrate according to the invention as disclosed above and the acyl glutamine-containing amino acid donor according to the invention, e.g. any of SEQ ID NO:7-294 as disclosed herein, are contacted in the presence of mTG2 to obtain the inventive protein as disclosed above. The term "contacted" as used in the inventive method refers to any situation in which two or more molecules, such as the amino donor-comprising substrate and the acyl glutamine-containing amino acid donor in accordance with the invention, are brought into intimate physical contact with one another, e.g. form part of the same reaction mixture or aqueous solution. For example, the mTG2-mediated reaction according to the inventive method may comprise reacting the acyl glutamine-containing amino acid donor according to the invention with an 1-60 molar equivalent, or 1-50 molar equivalent of the amino donor-comprising substrate according to the invention, e.g. with an 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 molar equivalent, or e.g. with a molar equivalent of about 2 molar to about 45 molar, from about 5 molar to about 40 molar, from about 10 molar to about 35 molar, from about 12.5 molar to about 30 molar, from about 15 molar to about 32.5 molar, from about 7.5 molar to about 27.5 molar, from about 17.5 molar to about 25 molar, from about 0.5 molar to about 1 molar. The concentration of the acyl glutamine-containing amino acid donor according to the invention may be from about 0.1 mg/ml to about 100 mg/ml, e.g. from about 0.5 mg/ml to about 75 mg/ml, from about 1 mg/ml to about 50 mg/ml, from about 2.5 mg/ml to about 45 mg/ml, from about 5 mg/ml to about 40 mg/ml, from about 10 mg/ml to about 35 mg/ml, from about 12.5 mg/ml to about 30 mg/ml, from about 15 mg/ml to about 25 mg/ml, from about 17.5 to about 20 mg/ml, e.g. 0.15 mg/ml, 0.2 mg/ml, 0.25 mg/ml, 0.3 mg/ml, 0.35 mg/ml, 0.4 mg/ml, 0.45 mg/ml, 0.5 mg/ml, 0.55 mg/mi, 0.6 mg/ml, 0.7 mg/ml, 0.8 mg/ml, 0.9 mg/mi, 2 mg/ml, 3 mg/ml, 4, mg/ml, 6 mg/ml, 7 mg/mi, 8 mg/ml, 9 mg/ml, 11 mg/ml, 12 mg/ml, 13 mg/ml, 14 mg/ml, 16 mg/ml, 19 mg/ml, 23 mg/ml, 27 mg/ml, 31 mg/ml, 33 mg/ml, 37.5 mg/mi, 41 mg/ml, 42 mg/ml, 43 mg/ml, 44 mg/ml, 46 mg/ml, 47 mg/ml, 48 mg/ml, 49 mg/ml.

In the inventive method mTG2 may be e.g. present in an amount from about 0.01 mol equivalents to about 2 mol equivalents to the substrate, e.g. to the protein comprising the acyl glutamine-containing amino acid donor sequence, from about 0.05 mol equivalents to about 1.5 mol equivalents, from about 0.1 mol equivalents to about 1.125 mol equivalents, from about 0.125 mol equivalents to about 1.75 mol equivalents, from about 0.25 mol equivalents, 0.3 mol equivalents, 0.4 mol equivalents, 0.5 mol equivalents, 0.6 mol equivalents, 0.7 mol equivalents, 0.8 mol equivalents to about 1 mol equivalents, or from about 1 mol equivalents to about 2.5 mol equivalents, preferably mTG2 is used in the inventive method in an amount of about 1 mol equivalents. In the inventive method the reaction may e.g. be allowed to proceed 25° C.-37° C. for about 1-5 hours, or for about 2-4 hours, or for about 2.5 hours to about 3.5h, or for about 1 hour, 2 hours, 3 hours, 4 hours. The inventive method may e.g. be carried out in any suitable buffer such as HEPES (4-2-hydroxyethyl-1-piperazineethanesuifonic acid), MOPS (3-(N-morpholino)propanesulfonic acid), or PIPES (piperazine-N,N-bis(2-ethanesulfonic acid) at a pH of about pH7.0.

According to one embodiment the acyl glutamine-containing amino acid donor according to the invention which may be used in the inventive method may be as disclosed above, e.g. the inventive acyl glutamine-containing amino acid donor may be an antibody, antigen-binding antibody fragment, enzyme, or a non-immunoglobulin scaffold as disclosed above.

Microbial transglutaminase, such as e.g. mTG2 which may be used according to the embodiments of the present invention, may be obtained from *Streptoverticillium mobaraense*, or any of its substrains, such as e.g. 40847, according to the method disclosed in Biochem. J. (1994) 299:825-829. For example, *Streptoverticillium mobaraense* may e.g. cultivated as described by Ando et al. (1989) Agric. Biol. Chem. 53, 2613-2617: In 2L Erlenmeyer flasks, 0.1 ml of the spore suspension may be grown in 500 ml of a medium containing: polypeptone, 2.0%; yeast extract, 0.2%; $K_2HPO_4$, 0.2%; $MgSO_4$, $7H_2O$, 0.1% ; potato starch, 2.0%; glucose, 0.5%; pH 7.0. Cultivation may be continued at 30° C., and the culture may be aerated and shaken at 90 rev./min for 9-11 days until the maximum of enzyme activity was reached. The culture fluid may then be separated from the mycel by centrifugation at 10000 g for 10 min and subsequent filtration over a folded filter paper. The supernatant may directly be utilized in chromatography or stored at −20° C. for later use. For scaled-up production, 1.0 ml of the cell suspension may be transferred to 3.5 L of a medium containing 2.5% potato starch instead of 2.0%, and 1.0% glucose instead of 0.5%. The culture may be grown with aeration (2 litres/min) and stirring at 140-180 rev./min for the first day and subsequently at 300-350 rev./min. Maximum of enzyme activity is typically achieved after 7 days. *Streptoverticillium mobaraense* may e.g. be obtained from ATCC® (ATCC 29032), or e.g. DSM, Braunschweig, Germany.

In one embodiment the inventive amino donor-comprising substrate which is used in the inventive method is coupled or covalently bound to a dye, drug, ribozyme, nanobody, enzyme, or linker as disclosed above. For example, the acyl glutamine-containing amino acid donor may be an antibody or antigen binding fragment as defined above which comprises at its carboxyterminus the inventive acyl glutamine-containing amino acid sequence according to SEQ ID NO:2, or e.g. according to any one of SEQ ID NO:7-294 as disclosed herein. For example, the amino donor-comprising substrate may be as defined above, e.g. may be a peptide comprising at least one lysine residue, or the tripeptide GGG as disclosed above which may e.g. be coupled to a linker, dye, drug, ribozyme, nanobody, or enzyme as disclosed above.

According to one embodiment the linker used in the inventive method may e.g. be further linked to a cytotoxic drug (payload), dye, or radioisotope as defined above. In the inventive method the acyl glutamine-containing amino acid donor and the amino donor-comprising substrate may e.g. be present in a reaction mixture in a ratio of about 1:40 molar equivalents (antibody: amino donor-comprising substrate) or in any molar equivalent disclosed above, with microbial transglutaminase 2 present in an amount as disclosed above, e.g. in a 1:1 molar equivalent to the antibody comprising the inventive acyl glutamine-containing amino acid donor sequence as disclosed above. According to the inventive method the reaction may e.g. be allowed to proceed about 1-5 hours at 25°-37° C., e.g. 1 hour, 2 hours, 2.5 hours, 3 hours, 3.5 hours, 4 hours or 5 hours at 25° C., 26° C., 27° C., 28° C., 29° C., 30° C., 31° C., 32° C., 33° C., 34° C., 35° C., 36° C., or 37° C.

In one embodiment the present invention provides for a protein according to the invention which is obtainable by the inventive method as disclosed above. Accordingly, the protein obtainable according to the present invention may be any protein as disclosed herein, e.g. an antibody, antigen binding fragment, enzyme, or a non-immunoglobulin scaffold as disclosed herein, which comprises the amino acid sequence according to SEQ ID NO:2. For example, the protein obtainable by the inventive method may comprise an antibody drug conjugate comprising the at least one acyl glutamine-containing amino acid donor sequence according to SEQ ID NO:2 as disclosed herein, preferably 2, more preferably 4 acyl glutamine-containing amino acid donor sequences as disclosed above which are covalently bound via an isopeptide bond formed between the acyl glutamine-containing amino acid donor of the invention (e.g. $X_1X_2X_3$TYFQAYG $X_4X_5X_6$), whereby the isopeptide bond is formed between the central glutamine residue (underlined) and the amino group of the amino donor-comprising substrate.

In one embodiment the present invention pertains to the use of a polypeptide sequence according to SEQ ID NO:2 in the inventive method as disclosed above. Accordingly, the present invention pertains to the use of one or more, e.g. 1, 2, 3, 4, 5, or more of the inventive polypeptide sequences disclosed herein in the inventive method. For example, the present invention pertains to the use of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, or SEQ ID NO: 294 in the inventive method.

For example, the polypeptide according to SEQ ID NO:2 may be carboxyterminally fused the HC or LC of an antibody as disclosed above. For example, sequences in which both $X_3$, $X_4$ are C as disclosed above are preferred, accordingly, the use of polypeptide sequences SEQ ID NO:7, SEQ ID NO:8, SEQ ID NO:9, SEQ ID NO:10, SEQ ID NO:11, SEQ ID NO:55, SEQ ID NO:56, SEQ ID NO:57, SEQ ID NO:58, SEQ ID NO:59, SEQ ID NO:103, SEQ ID NO:104, SEQ ID NO:105, SEQ ID NO:106, SEQ ID NO:107, SEQ ID NO:31, SEQ ID NO:32, SEQ ID NO:33, SEQ ID NO:34, SEQ ID NO:35, SEQ ID NO:36, SEQ ID NO:79, SEQ ID NO:80, SEQ ID NO:81, SEQ ID NO:82, SEQ ID NO:83, SEQ ID NO:84, SEQ ID NO:127, SEQ ID NO:128, SEQ ID NO:129, SEQ ID NO:130, SEQ ID NO:131, SEQ ID NO:13, SEQ ID NO:14, SEQ ID NO:15, SEQ ID NO:16, SEQ ID NO:17, SEQ ID NO:18, SEQ ID NO:61, SEQ ID NO:62, SEQ ID NO:63, SEQ ID NO:64, SEQ ID NO:65, SEQ ID NO:66, SEQ ID NO:109, SEQ ID NO:110, SEQ ID NO:111, SEQ ID NO:112, SEQ ID NO:113, SEQ ID NO:114, SEQ ID NO:37, SEQ ID NO:38, SEQ ID NO:39, SEQ ID NO:40, SEQ ID NO:41, SEQ ID NO:42, SEQ ID NO:85, SEQ ID NO:86, SEQ ID NO:87, SEQ ID NO:88, SEQ ID NO:89, SEQ ID NO:90, SEQ ID NO:133, SEQ ID NO:134, SEQ ID NO:135, SEQ ID NO:136, SEQ ID NO:137, or SEQ ID NO:138, more preferred is the use of any of SEQ ID NO:85, SEQ ID NO:86, SEQ ID NO:87, SEQ ID NO:88, SEQ ID NO:89, or SEQ ID NO:90.

In one embodiment the present invention also provides polynucleotides encoding an inventive polypeptide according to SEQ ID NO:2. Accordingly, the present invention provides for polynucleotides encoding the inventive polypeptide according to SEQ ID NO:2 of the following structure:

```
                                          (SEQ ID NO: 301)
5'-NNN₁ NNN₂ NNN₃ ACN TAY TTY CAR GCN TAY GGN NNN₄

NNN₅ NNN₆-3',
``` wherein N denotes any nucleotide (A, C, T, G), Y denotes a pyrimidine base (C or T), R denotes a purine base (A or G). Base nomenclature is according to the Nomenclature Committee of the International Union of Biochemistry (NC-IUB), see e.g. J. Biol. Chem., 1986, 261, 13-17. $NNN_1$-$NNN_6$ indicate codons 1-6, whereby codon $NNN_1$ encodes amino acid $X_1$ of SEQ ID NO:2, $NNN_2$ amino acid $X_2$ of SEQ ID NO:2, $NNN_3$ amino acid $X_3$ of SEQ ID NO:2, $NNN_4$ amino acid $X_4$ of SEQ ID NO:2, $NNN_5$ amino acid $X_5$ of SEQ ID NO:2 and $NNN_6$ amino acid $X_6$ of SEQ ID NO:2. For example, depending on the intended use of the polynucleotides codon usage should be optimized for the specific host, e.g. in case the polynucleotides are used for expressing the inventive peptide or inventive protein as disclosed above in a mammalian, eukaryotic or prokaryotic host the different codon usage by the respective host should be considered. For example, if the inventive polynucleotide is used for expression in a rodent or human cell lines, such as CHO or HEK 293 cells, for the manufacture of a therapeutic, the corresponding codon usage should be used to increase e.g. protein production (Trends in Molecular Medicine, November 2014, Vol. 20, No. 11). Codons $NNN_1$-$NNN_6$ according to the invention may not, however, code for a stop codon, e.g. TAG (amber), TAA (ochre), or TGA (opal).

Accordingly, $NNN_1$ may be any one of codons GCT, GCC, GCA, GCG, GTT, GTC, GTA, GTG, ATT, ATC, ATA CTT, CTC, CTA, CTG, TTA, TTG, ATG, GGT, GGC, GGA, GGG, $NNN_2$ may be any one of codons GAT, GAC, GAA, GAG, $NNN_3$, $NNN_4$ may be any one of codons TGT, TGC, AAT, AAC, $NNN_5$ may be one of codons TCT, TCC, TCA, TCG, AGT, AGC, ACT, ACC, ACA, ACG, AAT, AAC, CAA, CAG, $NNN_6$ may be any one of codons GAT, GAC, GAA, GAG.

In one embodiment the present invention also provides for a vector which comprises the inventive polynucleotides as disclosed above. The vector according to the invention may e.g. be an expression vector. The term "expression vector" as used for the vector according to the invention to a nucleic acid vector that comprises a gene expression controlling region, such as a promoter or promoter component, operably linked to a nucleotide sequence encoding at least one polypeptid, e.g. at least the inventive polypeptide sequence according to any of SEQ ID NO:2-SEQ ID NO:294. Expression vectors which may e.g. include pCMV-based expression vectors, or pD912-based vectors and variants thereof, Gateway® expression vectors, pcDNA-based expression vectors, or pJΩ vectors (see e.g. Nucleic Acids Research, Vol. 18, No. 4), or vectors which may be used for retroviral or lentiviral production (see e.g. Front Biosci. 1999 Jun. 1; 4:D481-96.). In the vector according to the invention the polynucleotides may e.g. be comprised 5' or 3' to an multiple cloning site (MCS), which will allow to generate in-frame fusion proteins when a corresponding cDNA encoding e.g. an antibody light or heavy chain, is cloned into the MCS. Depending on the location of the MCS the inventive polynucleotide will be expressed as an aminoterminal or carboxyterminal fusion protein.

In one embodiment the present invention also provides a host cell which comprises the inventive polynucleotide sequence as disclosed above, e.g. according to SEQ ID NO:2, or e.g. any of SEQ ID NO:7-294, or which comprises a vector according to the invention as disclosed above. For example, a host cell according to the invention comprising the inventive polynucleotide or a vector according to the invention as disclosed above refers to any type of cell that can contain the vector according to the invention. The host cell can be a eukaryotic cell, e.g., plant, animal, fungi, or algae (e.g. *Phaeodactylum tricomutum, Chlamydomonas reinhardtii*) or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. A host cell according to the invention may e.g. include HEK293, HEK293T, HEK293E, HEK 293F, NS0, per.C6, MCF-7, HeLa, Cos-1, Cos-7, PC-12, 3T3, Vero, vero-76, PC3, U87, SAOS-2, LNCAP, DU145, A431, A549, B35, H1299, HUVEC, Jurkat, MDA-MB-231, MDA-MB-468, MDA-MB-435, Caco-2, CHO, CHO-K1, CHO-B11, CHO-DG44, BHK, AGEI.HN, Namalwa, WI-38, MRC-5, HepG2, L-929, RAB-9, SIRC, RK13, 11B11, 1D3, 2.4G2, A-10, B-35, C-6, F4/80, IEC-18, L2, MH1C1, NRK, NRK-49F, NRK-52E, RMC, CV-1, BT, MDBK, CPAE, MDCK.1, MDCK.2, D-17, or e.g. *Saccharomyces cerevisiae, Hansenula polymorpha, Schizosaccharomyces pombe, Schwanniomyces occidentalis, Kluyveromyceslactis, Yarrowia lipolytica* and *Pichia pastoris*, or e.g. Sf9, Sf21, S2, Hi5, or BTI-TN-5B1-4 cells, or e.g. DH5α *E. coli*.

In one embodiment the present invention also provides for an antibody or antigen-binding fragment thereof, bivalent antibody, or VHH antibody comprising at least one amino acid sequence according to SEQ ID NO:2. Antibodies, antigen-binding fragments thereof, bivalent antibodies, or VHH antibodies according to the invention are as disclosed above. For example, an antibody according to the invention may comprise at least one amino acid sequence according to SEQ ID NO:2 (e.g. the acyl glutamine-containing amino acid donor according to the invention), e.g. as a carboxyterminal fusion to a light or heavy chain. The antibody according to the invention preferably comprises 2, or 4 inventive amino acid sequences according to SEQ ID NO:2, e.g. the antibody of the invention may comprise two light chains, or two heavy chains which comprise at their carboxy terminus the inventive amino acid sequence according to SEQ ID NO:2. Preferably, both heavy and light chains comprise as carboxyterminal fusions the inventive amino acid sequence according to SEQ ID NO:2. The inventive antibodies may e.g. also be modified by PCR-based site directed mutagenesis as disclosed above to remove terminal lysine residues in the Fc domain.

According to one embodiment the antibody according to the invention as disclosed above is a human or humanized monoclonal antibody as disclosed above, preferably, an IgG1, IgG2, IgG3, IgG4, or IgM type antibody. The inventive antibody comprises at least one linker covalently coupled to it according to the inventive method disclosed above. For example, the inventive antibody may comprise one, two, three, or four linker (e.g. cleavable or non-cleavable as disclosed above), which have been covalently coupled to the antibody according to the inventive method disclosed herein. According to one embodiment the inventive linker is further coupled to a dye, radioisotope, or cytotoxin as disclosed above.

In one embodiment the inventive antibody as disclosed above specifically binds to cancer cell surface antigens. Cancer cell surface antigens according to the invention include, but are not limited to EGFR (epidermal growth factor receptor), HER2, HERO, AFP, $\alpha_v\beta_3$ integrin, MUC16, CD4, CD20, CD22, CD30, CD33, CD52, CD56, CD66e, CD140b, CD227, EpCam, GD3, PSMA, or VEGF. Cancer cell surface antigens according to the invention also include cancer stem cell such as e.g. CD123, CLL-1, combinations of SLAMs (signaling lymphocyte activation molecule family receptors; see Yilmaz et al., "SLAM family markers are conserved among hematopoietic stem cells from old and reconstituted mice and markedly increase their purity," Hematopoiesis 107: 924-930 (2006)), such as CD150, CD244, and CD48, and those markers disclosed in U.S. Pat. No. 6,004,528.

In a preferred embodiment the antibody according to the invention is cetuximab (c225), or e.g. a biosimilar thereof which binds to EGFR. The term "biosimilar" as used for the inventive cetuximab is used in a manner that is consistent with the working definition promulgated by the US FDA which defines a biosimilar product to be one that is "highly similar" to a reference product (despite minor differences in clinically inactive components). In practice there can be no clinically meaningful differences between the reference product and the biosimilar product in terms of safety, purity, and potency (Public Health Service (PHS) Act § 262).

For example, cetuximab (or e.g. its biosimilar) according to the invention comprises at least one, preferably at least two, more preferably four acyl glutamine-containing amino acid donor sequences according to the invention. For example, cetuximab according to the invention comprises two, or preferably four linkers as defined above further coupled to a cytotoxin as above.

According to one embodiment cetuximab (or e.g. its biosimilar) according to the invention may be used in the treatment of cancer. The term "cancer" as used in the present invention refers to a cellular disorder characterized by uncontrolled or disregulated cell proliferation, decreased cellular differentiation, inappropriate ability to invade surrounding tissue, and/or ability to establish new growth at ectopic sites. The term "cancer" further encompasses primary and metastatic cancers. The inventive antibody cetuximab may e.g. be used to treat one of breast cancer, prostate cancer, ovarian cancer, cervical cancer, skin cancer, pancreatic cancer, preferably colorectal cancer, metastatic (mCRC), non-resectable liver metastases, Squamous Cell Carcinoma of the Head and Neck, Non-Small Cell Lung Cancer (NSCLC), Head and Neck Squamous Cell Carcinoma (HNSCC). Cetuximab (c225, or its biosimilar) may e.g. be used in patients that particularly benefit from such a treatment, e.g. patients with epidermal growth factor receptor (EGFR)-expressing, RAS wild-type metastatic colorectal cancer. Cetuximab according to the invention (or its biosimilar) may also be used in combination with irinotecan-based chemotherapy, or e.g. in first-line treatment in combination with FOLFOX, or e.g. as a single agent in patients who have failed oxaliplatin- and irinotecan-based therapy and who are intolerant to irinotecan.

In one embodiment the present invention provides for a composition which comprises the inventive antibody as disclosed above, which comprises at least one further pharmaceutically active ingredient. For example, the composition according to the invention may comprise cetuximab (or e.g. its biosimilar) in aqueous or lyophilized form and at least one further chemotherapeutic agent, wherein the agent is selected from the group comprising capecitabine, 5-fluoro-2'-deoxyuridine, irinotecan, 6-mercaptopurine (6-MP), cladribine, clofarabine, cytarabine, floxuridine, fludarabine, gemcitabine, hydroxyurea, methotrexate, bleomycin, paclitaxel, chlorambucil, mitoxantrone, camptothecin, topotecan, teniposide, colcemid, colchicine, pemetrexed, pentostatin, thioguanine; leucovorin, cisplatin, carboplatin, oxaliplatin, or a combination of 5-FU, leucovorin, a combination of 5-fluorouracil/folinic acid (5-FU/FA), a combination of 5-fluorouracil/folinic acid (5-FU/FA) and oxaliplatin (FLOX), a combination of 5-FU, leucovorin, oxaliplatin (FOLFOX), or a combination of 5-FU, leucovorin, and irinotecan (FOLFIRI), or a combination of leucovorin, 5-FU, oxaliplatin, and irinotecan (FOLFOXIRI), or a combination of Capecitabine and oxaliplatin (CapeOx).

According to one embodiment the present invention provides a pharmaceutical composition which comprises the inventive antibody as disclosed above, or the composition according to the invention and at least one further ingredient. Accordingly, the present invention provides for pharmaceutical compositions which comprise the inventive antibody and which may comprise excipients and/or stabilizers and/or surfactants and/or preservatives. The term "excipients" as used herein means a component of a pharmaceutical product that is not an active ingredient such as, for example, diluents. The excipients that are useful in preparing the inventive pharmaceutical composition are generally safe and non-toxic. Surfactants that may be used with the inventive pharmaceutical composition include e.g. anionic surfactants such as e.g. a mixture of sodium alkyl sulfates, cationic surfactants, such as e.g. quaternary ammonium and pyridinium cationic surfactants, or non-ionic surfactants, such as e.g. Sorbitan esters, polysorbates, e.g. Polysorbat 20 (Polyoxyethylen-(20)-sorbitanmonolaurat), Polysorbat (Polyoxyethylen-(4)-sorbitanmonolaurat), Polysorbat 40 (Polyoxyethylen-(20)-sorbitanmonopalmitat), Polysorbat 60 (Polyoxyethylen-(20)-sorbitan-monostearat), Polysorbat (Polyoxyethylen-(4)-sorbitanmonostearat), Polysorbat 65 (Polyoxyethylen-(20)-sorbitantristearat), Polysorbat 80 (Polyoxyethylen-(20)-sorbitanmonooleat), Polysorbat 81 (Polyoxyethylen-(5)-sorbitanmonooleat) Polysorbat 85 (Polyoxyethylen-(20)-sorbitantrioleat), Polysorbat 120 (Polyoxyethylen-(20)-sorbitanmonoisostearat), or poloxamers e.g. poloxamer 105, poloxamer 108, poloxamer 122, poloxamer 124, poloxamer 105 benzoate. Preservatives which may be comprised in the pharmaceutical composition according to the invention may be benzalkonium chlorid in a concentration of 0.004% to 0.01%.

In one embodiment the present invention provides for a method of treating a subject in need thereof inflicted with cancer, wherein the treatment comprises administering to said subject (e.g. a patient, wherein the patient is preferably a human) a therapeutically effective amount of the pharmaceutical composition as disclosed herein. Accordingly, the present invention provides for a method of treating a subject in need thereof inflicted with cancer, e.g. as disclosed above, with a therapeutically effective amount of the inventive c225 (cetuximab) antibody, e.g. cetuximab according to the invention may be administered in a concentration of about 125 mg/m² to about 500 mg/m² body surface, preferably about 250 mg/m² to about 400 mg/m² body surface, whereby the dosing of cetuximab may e.g. be computed according to the Dubois method, in which the body surface area of a subject (m²) is computed using the subject's body weight: $m^2 = (wt\ kg^{0.425} \times height\ cm^{0.725}) \times 0.007184$.

EXAMPLES

The following Examples are intended to further illustrate the invention. They are not intended to limit the subject matter or scope of the invention thereto.

Example 1

Solid-Phase Synthesis of Peptides and Purification

Peptides were synthesized on an AmphiSpheres 40 RAM resin (Agilent, 0.27 mmol/g) by microwave-assisted Fmoc-SPPS using a Liberty Blue™ Microwave Peptide Synthesizer at a 0.1 mmol scale. Activation of the respective carboxyfunctional amino acid was performed by Oxyma/N,N'-Diisopropylcarbodiimide (DIC). Deprotection of the aminoterminal Fmoc-group was achieved using 20% piperidine in DMF in the presence of Oxyma. During the synthesis cycles all amino acids were heated to 90° C. (cysteines to 50° C.). Peptides were cleaved from the resin by a standard cleavage cocktail of 94% TFA, 2% triethylsilane, 2% anisole, 2% H2O. Cysteine containing peptides were cleaved in the presence of dithiothreitol (DTT) to suppress unwanted oxidation of cysteines. After 2 h of cleavage, peptides were precipitated in cold diethylether and washed twice with diethylether. The disulfide-bridged crude peptide was oxidized at 1 mg ml-1 in 100 mM $(NH_4)_2CO_3$ aq. pH 8.4 and oxidation monitored by RP-HPLC. Afterwards, peptides were isolated by preparative RP-HPLC.

RP-HPLC.

Peptides were analyzed by chromatography on an analytical RP-HPLC from Varian (920-LC) using a Phenomenex Hypersil 5u BDS C18 LC column (150×4.6 mm, 5 µm, 130 Å). Peptides were isolated by semi-preparative RP-HPLC (Varian) using a Phenomenex Luna 5u C18 LC column (250×12.2 mm, 5 µm, 100 Å). Eluent A (water) and eluent B (90% aq. MeCN) each contained 0.1% trifluoroacetic acid (TFA).

ESI-MS Analysis.

ESI mass spectra were collected on a Shimadzu LCMS-2020 equipped with a Phenomenex Jupiter 5u C4 LC column (50×1 mm, 5 µm, 300 Å) by using an eluent system of 0.1% aq. formic acid (eluent A) and acetonitrile containing 0.1% formic acid (eluent B).

Example 2

Peptide Biotinylation Assays.

Figure 4:
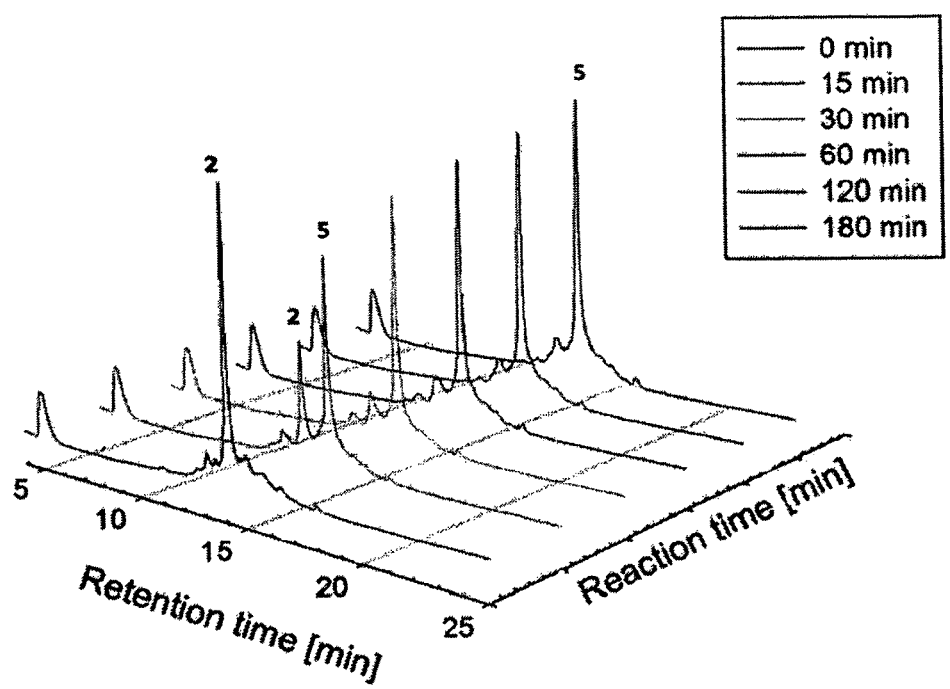
FIG. 4: RP-HPLC analysis of transglutaminase-promoted biotinylation of oxidized peptide 2 (gradient 10 to 80%). Peak areas of 2 and 5 were analyzed and background subtracted.
Figure 5:
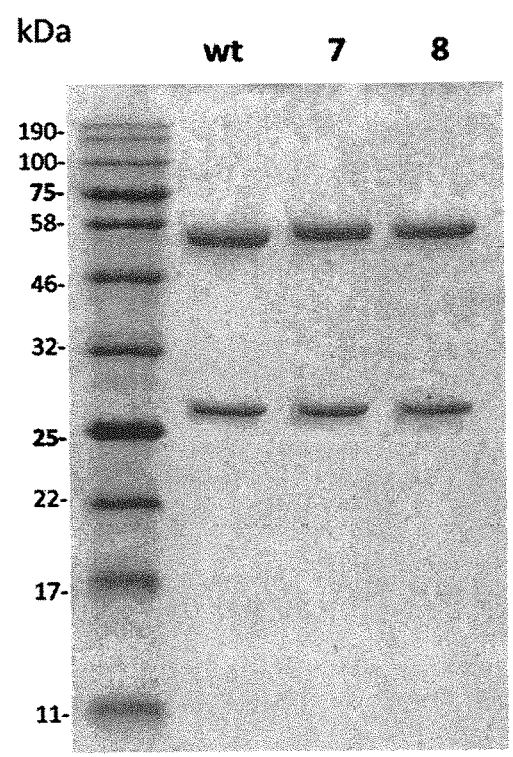
FIG. 5: Coomassie stained 15% SDS-PAGE gel analysis of purified cetuximab wildtype (lane 1) and cetuximab variants 7 and 8 (e.g. variant 7 corresponds to cetuximab according to the invention, which has been carboxyterminally fused to SEQ ID NO:90 and locked or constrained by a disulfide bridge, and variant corresponds to cetuximab carboxyterminally fused to SEQ ID NO:246 without disulfide bridge formation and not conformationally constrained. Antibodies were reduced in the presence of 2-mercaptoethanol prior to loading (2 pg/lane). Prestained protein ladder (New England Biolabs) is indicating protein sizes in kDa.
Figure 6:
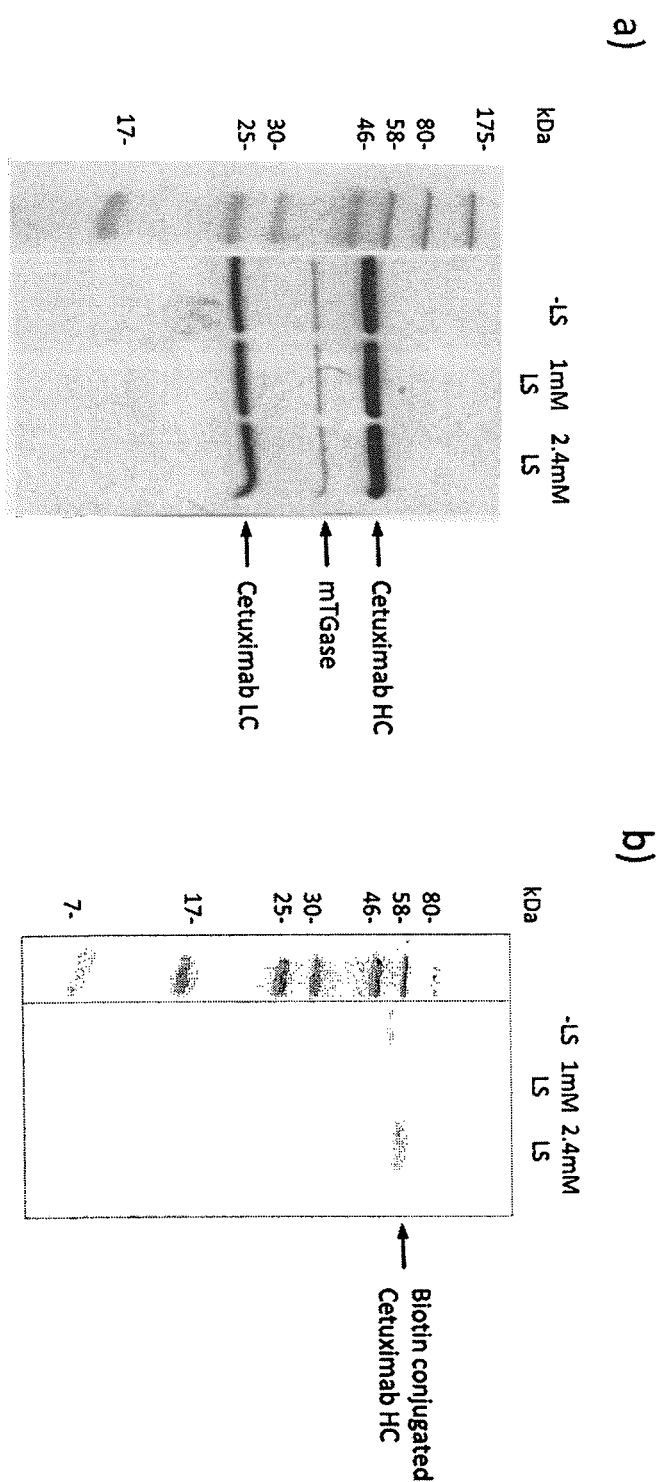
FIG. 6: Control experiment of transglutaminase-mediated cetuximab conjugation. a) Coomassie stained 15% SDS-PAGE gel analysis of transglutaminase-mediated conjugation of cetuximab wildtype with monobiotinyl cadaverine (MBC) in the presence of increasing concentration of the anionic surfactant N-lauroylsarcosin (LS), an agent described to release buried endo-glutamines from proteins making them accessible for tranglutaminase. b) Western-blot analysis of transglutaminase-mediated conjugation of cetuximab wildtype with monobiotinyl cadaverine (MBC) in the presence of increasing concentration of the anionic surfactant N-lauroylsarcosin (LS). Biotinylation was detected using streptavidin-alkaline phosphatase conjugate and NBT/BCIP. Prestained protein ladder (New England Biolabs) is indicating protein sizes in kDa.
Figure 7:
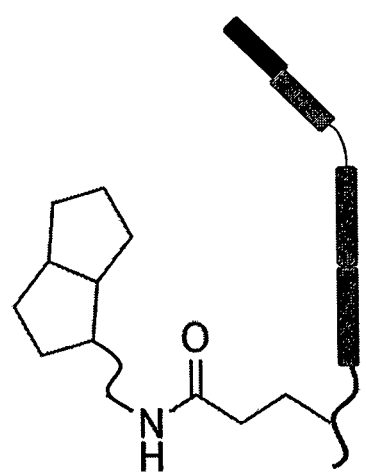
FIG. 7: Schematic representation of a heavy chain of 10 used for tryptic-digestion prior to MALDI-MS-analysis.
Figure 8:
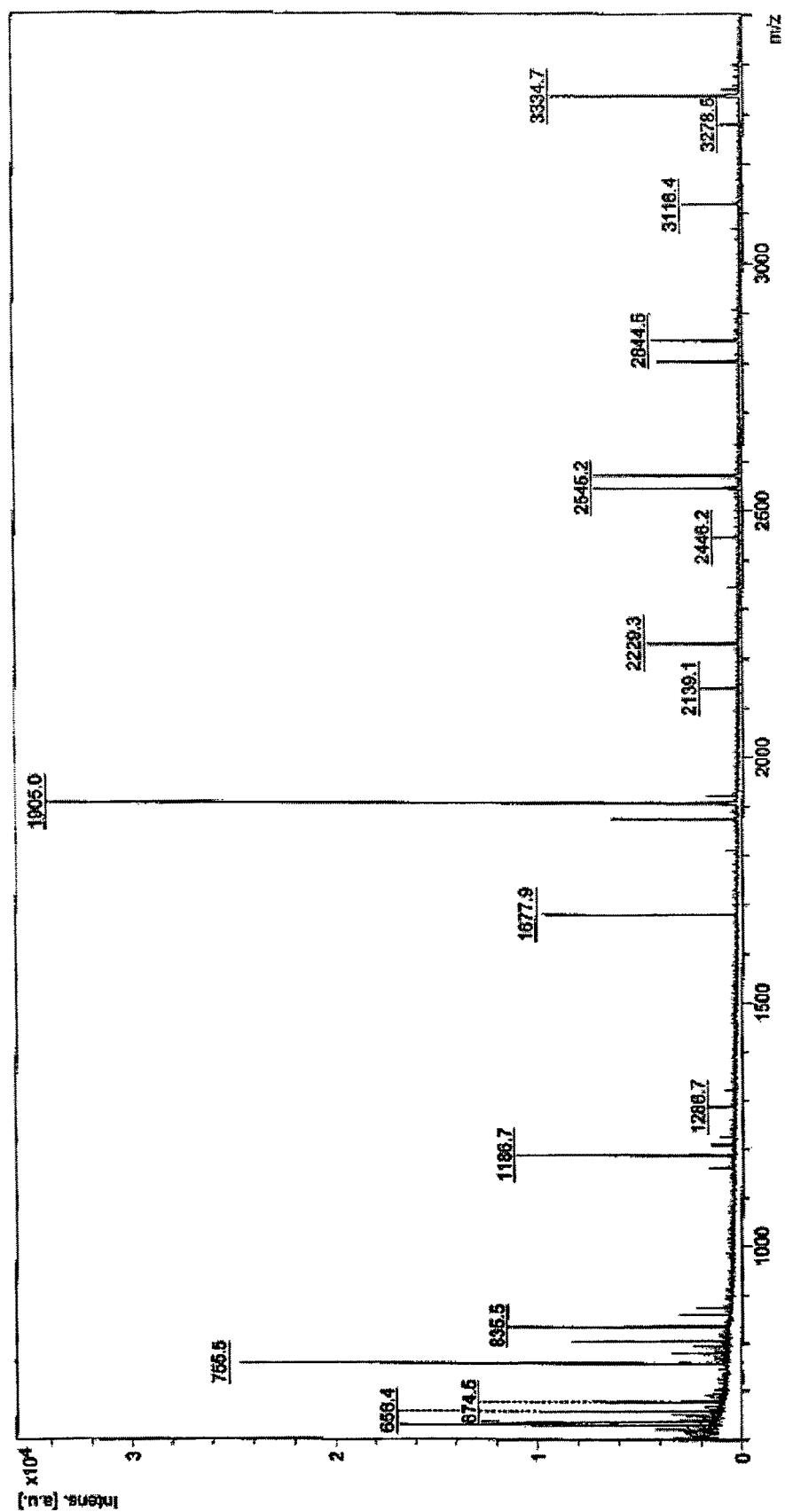
FIG. 8: MALDI-TOF-MS spectra of trypsin digested heavy chain of 10.
Figure 9:
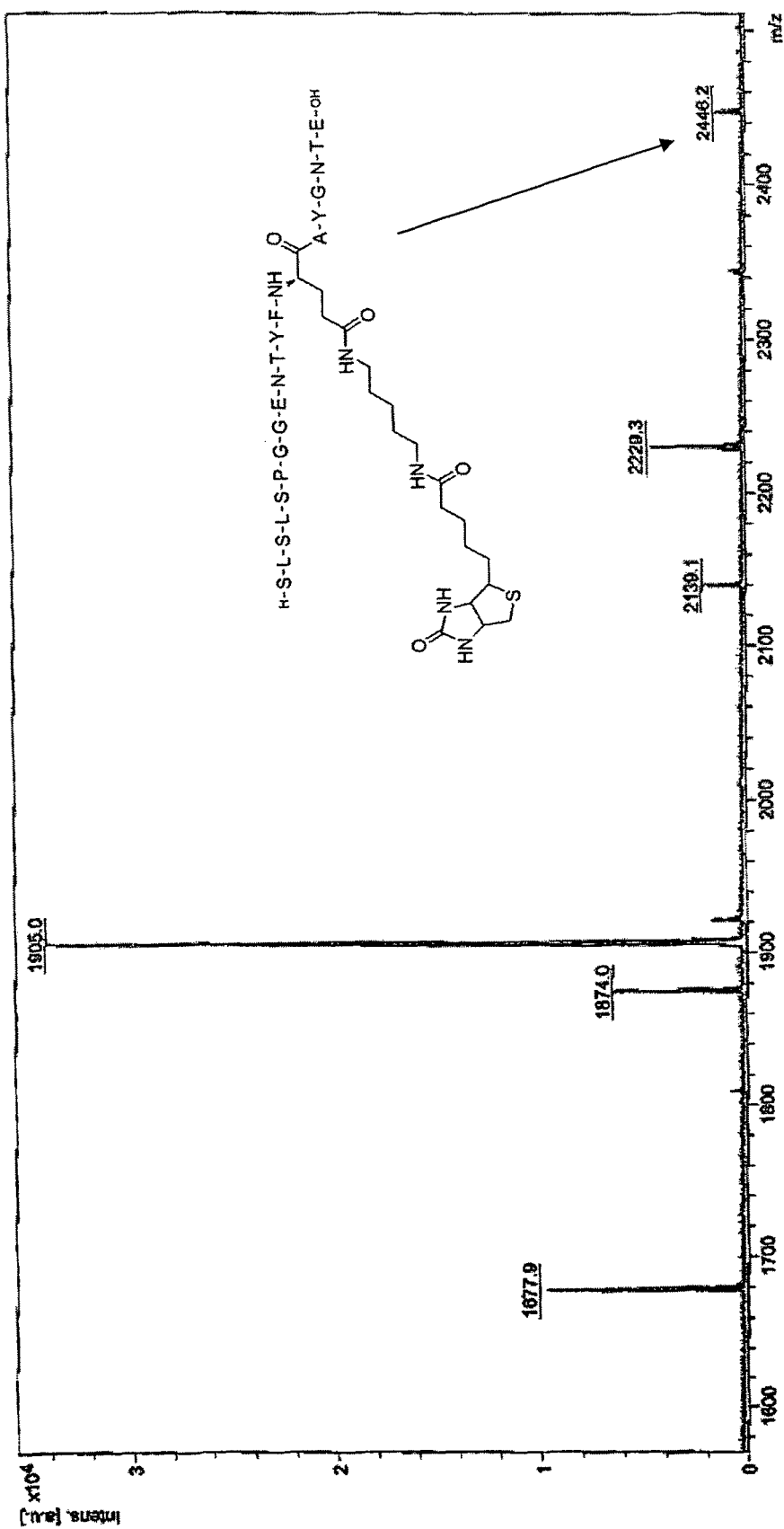
FIG. 9: MALDI-TOF-MS spectra of trypsin digested heavy chain of 10 in detail.
Figure 12:
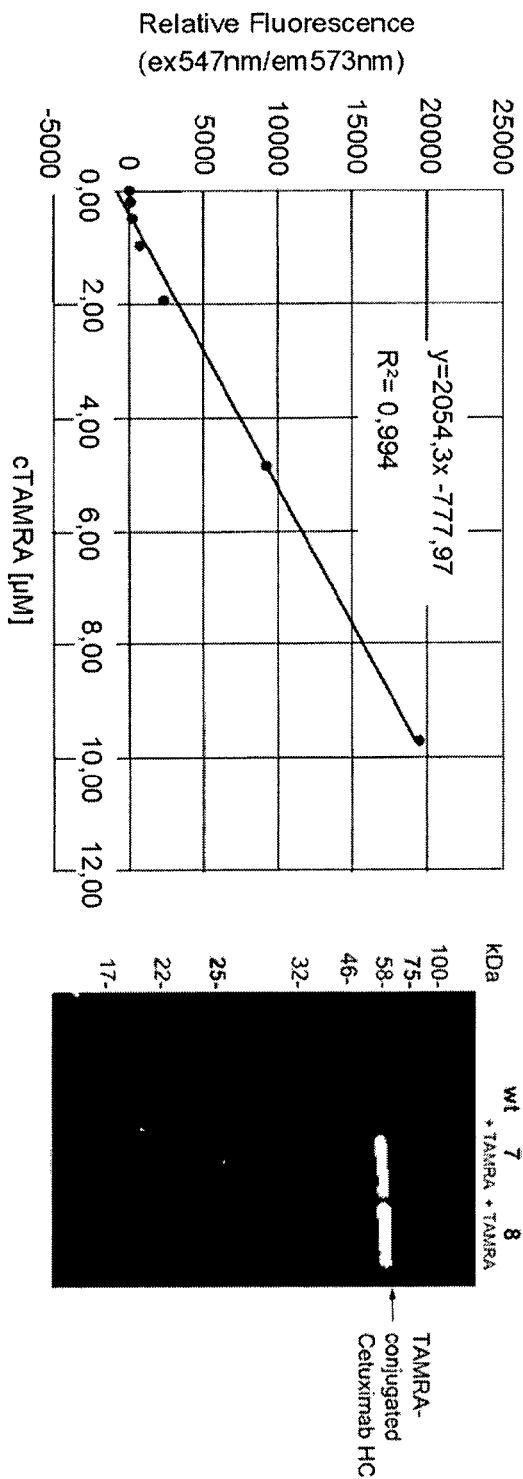
FIG. 12: Determination of antibody conjugation efficiency using TAMRA-cadaverine and fluorescence analysis.
Figure 13:
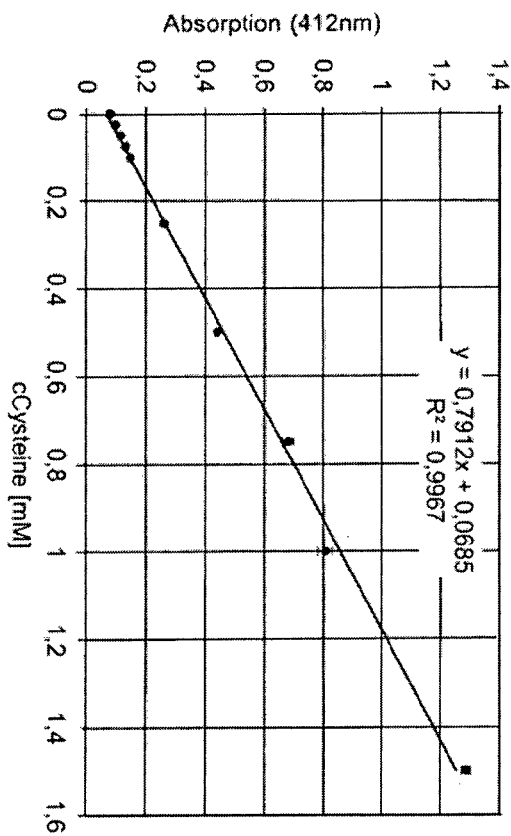
FIG. 13: Determination of free thiols in antibodies 7 and 8 using Ellman's reagent.

Peptides were dissolved at 50 mg/ml in DMSO and diluted to 1.25 mg/ml in 100 mM HEPES pH 7.0 for enzymatic conjugation. Monobiotinyl cadaverine was added at a 5 fold molar excess over peptide and enzymatic reactions initiated by addition of microbial transglutaminase at an enzyme/substrate ratio of 1/50 (w/w). For peptide biotinylation assays involving peptide 2 (SEQ ID NO: 90) and reference peptide GGGSLLQG (SEQ ID NO:295), the amount of microbial transglutaminase was reduced to an enzyme/substrate ratio of 1/385 and 1/182 (w/w), respectively. Reactions were incubated at 37° C. Aliquots of the reaction mixture were collected at 0, 15, 30, 60, 120, and 180 min and reactions stopped by transglutaminase removal using centrifugation dialysis (Microcon-10, 10.000 NMWL, Merck Millipore). Aliquots were analyzed by RP-HPLC by using a gradient from 10 to 80% eluent B (90% aq. MeCN) over 20 min at 1 ml/min (see FIG. 4). Fractions collected from the RP-HPLC analyses were further analyzed by ESI-MS.

Example 3

Enzymatic Antibody Conjugation using Transglutaminase.

Antibody expression and purification. Plasmids coding for cetuximab (Erbitux®) wildtype were kindly provided by Merck Serono (Darmstadt). Cetuximab mutants containing the TG-tags at the C-terminus of the heavy chain were prepared by standard SOE PCR techniques as described below. The C-terminal lysine was omitted in both constructs to avoid cross-reactivity of the c-amino group with transglutaminase-accessible glutamines. Antibodies were transiently expressed from HEK293F cells using the Expi293

Expression System (Life Technologies). Conditioned supernatants were applied to spin columns with PROSEP-A Media (Montage, Merck Millipore) and washed with 1.5 M Glycine/NaOH, 3 M NaCl, pH 9.0. Proteins were eluted with 0.2 M Glycine/HCl pH 2.5 and neutralized with 1M Tris/HCl pH 9.0. Eluted proteins were dialyzed in 1×DPBS (Life Technologies) and stored at 4° C.

PCR-based generation of tagged Cetuximab (lacking the terminal heavy chain lysine). PCR was used to generate c225 (Cetuximab) constructs lacking the carboxyterminal lysine residue of the heavy chain. Plasmids encoding C225 including a terminal lysine residue and the carboxyterminal amino acid sequence according to SEQ ID NO:246 were amplified using primers having the sequences according to SEQ ID NO:296, SEQ ID NO:299 (both at 1 pmole) for 10 cycles (PCR conditions: 3 min @ 98° C. (initial denaturing), 10 s @ 98° C., 30 s © 55° C., 15 s @ 72° C.), followed by 20 cycles using primers having the sequences according top SEQ ID NO:296, SEQ ID NO:300 (10 pmole primers) with the following cycling conditions: 10 s @ 98° C., 30 s @ 55° C., 15 s @ 72° C., final extension 5 min@ 72° C.

The resulting amplification product was gel purified and subsequently subjected to a restriction digest using EcoRV/BamHI (3 h @ 37° C.). The restriction fragment was then purified using a PCR purification kit. The fragment was then cloned into an EcoRV/BamHI digested pTT5_C225_HC vector (encoding the C225 heavy chain).

Antibody conjugation using transglutaminase. Antibodies were adjusted to 0.5 mg/ml and incubated with 40 mol equiv per conjugation site of monobiotinyl cadaverine (MBC) and 1 mol equiv microbial transglutaminase (mTGase) in 100 mM HEPES buffer pH 7.0 for 3 h at 25° C. For analytical issues, reactions were analyzed by 15% SDS-PAGE and biotinylated heavy chains visualized by semi-dry western blot with streptavidin-alkaline phosphatase conjugate and NBT/BCIP. For preparative production of antibody conjugates, excess substrate and mTGase were removed by size exclusion chromatography with 50 mM sodium phosphate buffer, 150 mM NaCl, pH 7.0 (Superdex S200 10/300 GL, GE Healthcare, 0.5 ml/min).

MALDI-TOF-MS analysis of conjugated antibodies. Prior to MS-analysis, antibodies (6 μg) were reduced in SDS-loading dye containing 2-mercaptoethanol and heavy and light chains separated under denaturing conditions using 15% SDS-PAGE. Proteins were visualized by Coomassie-MeOH staining. Protein bands corresponding to modified heavy chains were excised, cut into small pieces and washed twice with MQ water for 15 min to remove AcOH and MeOH from staining. Afterwards, gel pieces were washed twice with 2:3 MeCN:50 mM ammonium bicarbonate pH 8.0 for 30 min to remove stain. Gel pieces were dehydrated with MeCN and dried at 50° C. 20 mM Dithiothreitol (DTT) in 50 mM ammonium bicarbonate was added and the samples incubated at 60° C. for 45 min to reduce disulfide bonds. After the samples were cooled to room temperature, the DTT solution was removed and reduced cysteines were alkylated by the addition of 55 mM iodoacetamide (IAA) in 50 mM ammonium bicarbonate for 45 min in the dark. Excess alkylation mix was removed and the gel pieces washed twice with 50 mM ammonium bicarbonate pH 8.0. Gel pieces were then twice dehydrated with MeCN and swelled in 50 mM ammonium bicarbonate, before they were dehydrated and swelled in 50 mM ammonium bicarbonate containing 20 ng/μl trypsin (NEB, Trypsin-ultra, Mass Spectrometry grade) to give a final enzyme/substrate ratio of 1:20. Trypsin digest was performed overnight at 37° C. Peptides were extracted twice by the addition of 50% MeCN, 1% formic acid for 30 min shaking. Combined supernatants containing peptides were lyophilized and analyzed by MALDI-TOF-MS. The in-gel digestion procedure was adopted from the literature (M. Wilm, A. Shevchenko, T. Houthaeve, S. Breit, L Schweigerer, T. Fotsis, M. Mann, Nature 1996, 379, 466-469.).

Determination of antibody conjugation efficiency by fluorescence measurement. Antibody conjugation efficiency was determined by antibody labeling with N-(Tetramethylrodaminyl) cadaverine (TAMRA-cadaverine) and measurement of fluorescence at an excitation wavelength of 547 nm and an emission wavelength of 573 nm. For this purpose, antibodies were adjusted to 1.0 mg/ml and incubated with 20 mol equiv per conjugation site of TAMRA-cadaverine and 0.5 mol equiv microbial transglutaminase (MTG) in 100 mM HEPES buffer pH 7.0 for 3 h at 25° C. Unbound TAMRA-cadaverine was removed by gel filtration twice using Protein Desalting Spin Columns (Thermo Scientific) equilibrated with PBS. A non-antibody sample was incubated and treated in the same manner to exclude remaining free TAMRA-cadaverine after gel filtration. The weak fluorescence measured from this control was afterwards subtracted from the fluorescence of the antibody samples. The concentration of TAMRA-cadaverine conjugated antibodies was determined by using a standard curve of TAMRA-cadaverine ranging from 9.72 to 0.19 μM in PBS (40 μl per well) and fluorescence readout using a plate reader (Tecan Infinite M1000). The percentage of labeled/unlabeled antibodies was calculated from the total antibody concentration (determined at 280 nm, 9: MW=148211.72 g/mol ε280=223400 M-1m-1, 10: MW=148259.55 g/mol ε280=223150 M-1m-1) assuming each labeled antibody is conjugated to two TAMRA-moieties attached to the MTG-tag at the heavy chains. For analytical issues, reactions were also analyzed by 15% SDS-PAGE and TAMRA labeled heavy chains visualized by fluorescence readout.

Example 4

Cell Binding Experiments

Cell lines. EBC-1 and CHO-K1 cells were cultured in DMEM with 4 mM L-glutamine (Sigma-Aldrich) and DMEM-F12+GlutaMax™ (Gibco®), respectively, both supplemented with 10% fetal bovine (Sigma-Aldrich) at 37° C. and 5% CO2.

Cell binding experiments. Cell binding experiments were performed by using EGFR-overexpressing EBC-1[3] and EGFR-negative CHO-K1 cells in combination with confocal fluorescence microscopy and flow cytometry, respectively. Washing and incubation steps were performed at 4° C. using PBS with 1% BSA. For microscopy based experiments, cells were grown on glass coverslips followed by consecutive labelling with 100 nM of respective antibody-conjugates and 1:200 diluted Streptavidin Alexa Fluor® 488 conjugate (Life Technologies). Then, cells were fixed with 4% paraformaldehyde, mounted with ProLong® Diamond Antifade Mountant with DAPI (Life Technologies) and scanned using a Leica TCS SP5 confocal microscope equipped with a 100× objective (Leica Microsystems). For flow cytometry, 2×105 cells were incubated with 100 nM of respective antibody-conjugates and in a consecutive step with 1:200 diluted Streptavidin Alexa Fluor® 488 conjugate (Life Technologies). Cell fluorescence was determined using a BD Influx cell sorter and BD FACS Sortware with detection of 2×104 events.

Example 5

Bioconjugation of Cetuximab (c225) using mTG2 and GGG Amino Donor-Comprising Substrate Cetuximab heavy chain variants 9 and 10 (9: with inventive MTG-tag according to SEQ ID NO:90, 10: with inventive MTG-tag according to SEQ ID NO:246) with terminal lysine residues (K447) removed were conjugated to biotin-cadavarine, or GGGYK-Biotin.

Assay conditions for carrying out the mTG2-mediated conjugation reactions were as follows:

| Assay conditions | Conc [µM] |
|---|---|
| 50 mM Tris-HCl pH 7.5, 150 mM NaCl | 1x |
| mTG (0.4 eq.) | 1.364 |
| Cetuximab (according to the invention) | 0.5 mg/ml |
| MBC/GGG-Biotin/GGG-TAMRA/TAMRA-cadaverine (50 molar equivalent) | 170.4 |
| Incubation time: | 3 h@ 22° C. |

Figure 14:
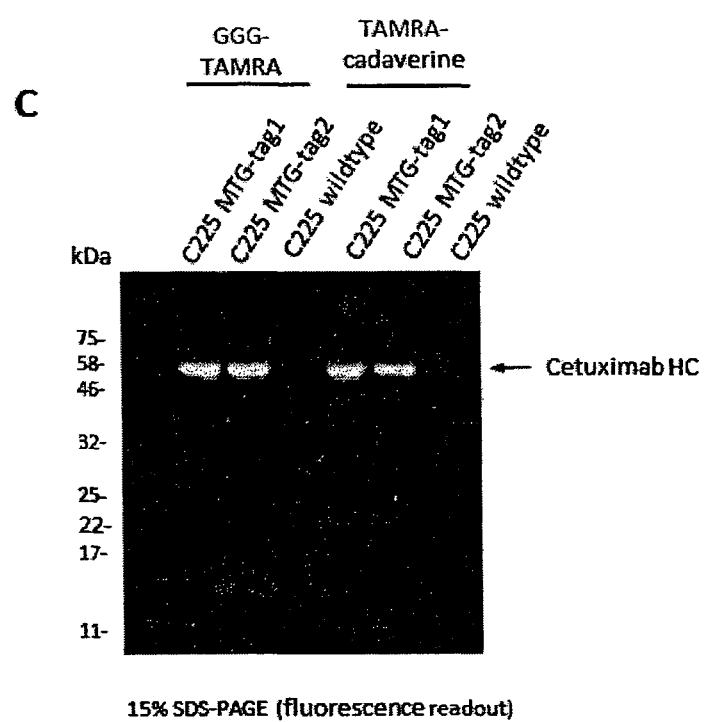
FIG. 14: (A) Western Blot using streptavidin-AP, NBT/BCIP for the detection of biotinylated cetuximab. Arrows indicate the position of cetuximab (biotinylated) and of mTG2. (B) Coomassie stained protein gel with lanes loaded as indicated (C) fluorescence readout for the detection cetuximab comprising MTG tag 1 (SEQ ID NO:90), or MTG-tag2 (SEQ ID NO:246) conjugated to fluorescent amino-donor substrates GGG-TAMRA or TAMRA-cadavarine.
Figure 16:
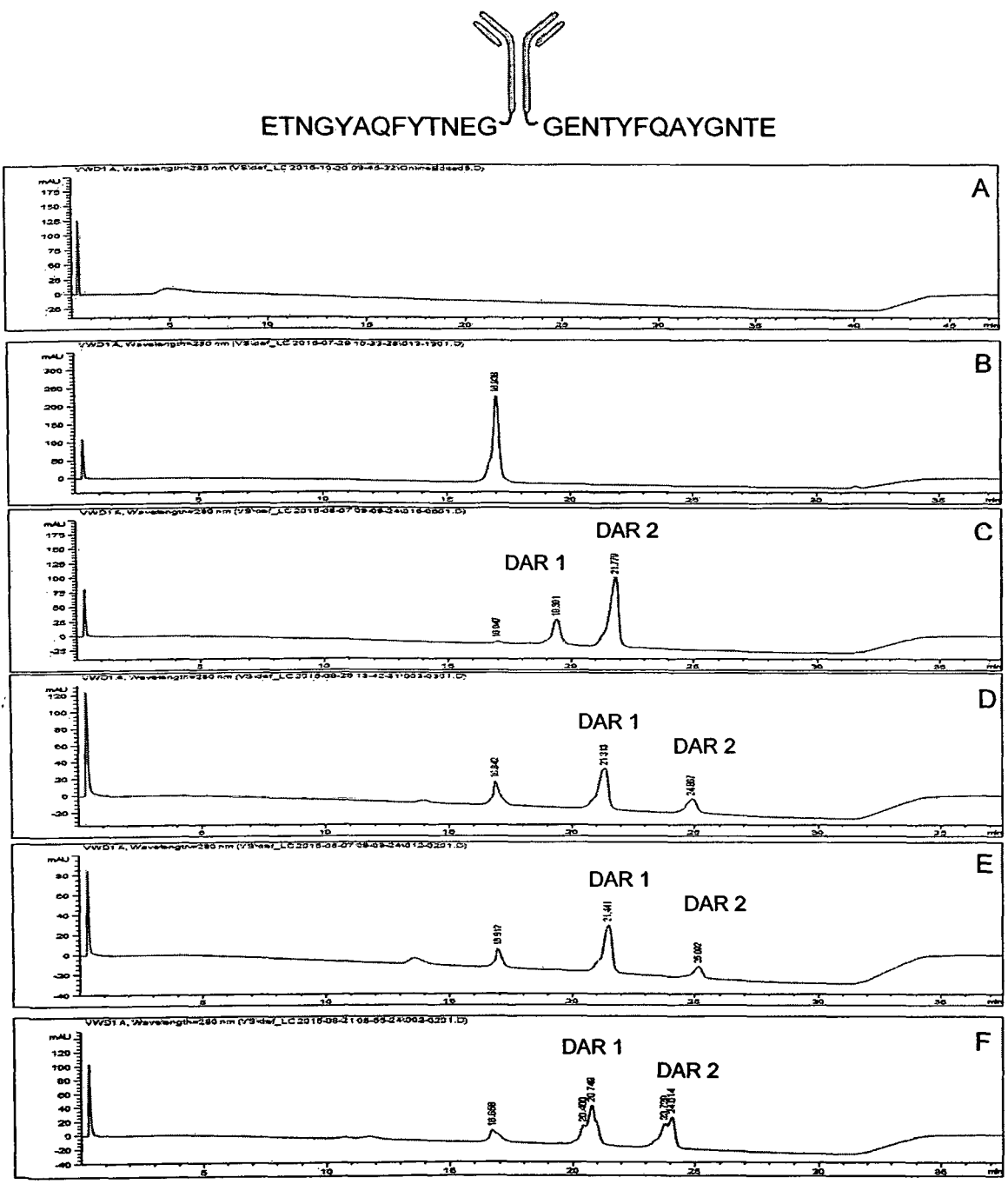
FIG. 16: Hydrophobic interaction chromatography (HIC) of antibody-drug-conjugates (ADCs) synthesized by catalysis of microbial transglutaminase (MTG). ADCs were generated by enzyme-mediated conjugation of cytotoxic payloads 1-4 as shown in FIG. 15 to an IgG1 antibody (cetuximab) with a carboxyterminal MTG-tag at each of its heavy chains. (A) Blank run, (B) Unconjugated antibody control, (C) ADCs with a different drug-to-antibody ratio (DAR) obtained by conjugation to payload 1, (D) ADCs with a different drug-to-antibody ratio (DAR) obtained by conjugation to payload 2, (E) ADCs with a different drug-to-antibody ratio (DAR) obtained by conjugation to payload 3, (F) ADCs with a different drug-to-antibody ratio (DAR) obtained by conjugation to payload 4.

Following the incubation for 3h at 22° C. the reaction was stopped by the addition of 2.5 µl of SDS loading dye and subsequent denaturation at 98° C. for 5 min. A 15% SDS polyacrylamide gel was loaded with the samples and run at 300V, 40 mA until the desired separation was achieved (see FIG. 14B). Western blotting was done (12V, 400 mA, 45 min). Fluorescent detection was done by placing the polyacryamide gel on a UV screen (λ=260-280 nm) (FIG. 14C).

Results:

Only cetuximab comprising the inventive MTG-tag1, or MTG-tag2 was fluorescently labeled, while wild-type cetuximab without the inventive polypeptide sequences according to SEQ ID NO:90, SEQ ID NO:246 is not fluorescently labeled indicating that the inventive MTG tags were efficiently recognized my mTG2.

Example 6

MTG-Promoted Conjugation Reactions

Antibody drug conjugates (ADCs) were synthesized in MTG-catalyzed reactions containing 1 mg/ml cetuximab tagged with SEQ ID NO: 246 (e.g. cetuximab comprising at SEQ ID NO: 246 at the carboxyterminus of each of the heavy chains), 20 equivalents of cytotoxic payload 1-4, and 0.1 equivalents of microbial transglutaminase (MTG). Reactions were performed in PBS pH 7.4 at 37° C. for 16 h and stopped by the addition of 1 volume of HIC buffer A.

ADC Analysis by Hydrophobic Interaction Chromatography (HIC)

ADCs were evaluated by hydrophobic interaction chromatography (HIC) on a TSKgel Butyl-NPR column (Tosoh Bioscience, 4.6 mm×3.5 cm, 2.5 µm) using an Agilent Infinity 1260 HPLC. The HIC method was applied using a mobile phase of 50 mM $NaH_2PO_4$, 1.5 M $(NH_4)_2SO_2$ pH 7.5 (Buffer A) and 50 mM $NaH_2PO_4$ pH 7.5 (Buffer B). ADCs (45 µg) in 0.75 M $(NH_4)_2SO_2$ were loaded and eluted with a gradient consisting of 2.5 min 0% Buffer B followed by a linear gradient into 100% Buffer B over 25 min with a flow rate of 0.9 ml/min.

The invention claimed is:

1. A protein comprising at least one acyl glutamine-containing amino donor sequence covalently linked via a γ-glutamyl-amide bond to an amino donor-comprising substrate, wherein the acyl glutamine-containing amino acid donor sequence comprises an amino acid sequence according to SEQ ID NO: 2 ($X_1X_2X_3$TYFQAYG $X_4X_5X_6$), wherein
   X1 is a hydrophobic amino acid,
   X2 is a negatively charged amino acid,
   X3 is C or N,
   X4 is C or N,
   X5 is one of an amino acid with a polar, uncharged side chains, and
   X6 is a negatively charged amino acid; and
wherein the protein is an antibody or antigen-binding fragment.

2. The protein according to claim 1, wherein the amino donor-comprising substrate comprises at least an 6-amino group, or at least one tripeptide having the sequence of GGG with a primary aminoterminal amino group.

3. The protein according to claim 1, wherein the amino donor-comprising substrate is a lysine residue, a lysine derivative, a polypeptide comprising at least one lysine residue.

4. The protein according to claim 1, wherein the amino donor-comprising substrate is covalently bound to a further molecule.

5. The protein according to claim 4, wherein the further molecule is one of a dye, radioisotope, drug, ribozyme, nanobody, enzyme, or linker.

6. The protein according to claim 5, wherein the linker is cleavable or non-cleavable and wherein the linker is coupled or covalently bound to a dye, radioisotope, or cytotoxin.

7. The protein according to claim 1, wherein
   X1 is any one of A, V, I, L, M or G,
   X2 is one of D, or E,
   X3 is C,
   X4 is C or N,
   X5, is S, T, or N,
   X6 is one of D, or E.

8. The protein according to claim 1, wherein
   X1 is any one of A, V, I, L, M or G,
   X2 is one of D, or E,
   X3 is C,
   X4 is C,
   X5, is S, T, or N,
   X6 is one of D, or E.

9. The protein according to claim 1, wherein
   X1 is any one of A, V, I, L, M or G,
   X2 is E,
   X3 is C,
   X4 is C,
   X5 is T, and
   X6 is E.

10. The protein according to claim 1, wherein
    X1 is G,
    X2 is E,
    X3 is C,
    X4 is C,
    X5 is T, and
    X6 is E (SEQ ID NO: 90).

11. A method of preparing a protein according to claim 1, comprising:
    contacting 1) an amino donor-comprising substrate with 2) an acyl glutamine-containing amino acid donor sequence comprising an amino acid sequence according to SEQ ID NO: 2 according to claim 1;
    in the presence of transglutaminase, to obtain a protein comprising said acyl glutamine-containing amino acid sequence covalently linked via a γ-glutamyl-amide bond to said amino donor comprising substrate;
    wherein the protein is an antibody or antigen-binding fragment.

12. Method according to claim 11, wherein the amino donor-comprising substrate is coupled or covalently bound to a dye, drug, ribozyme, nanobody, enzyme, or linker.

13. Method according to claim 12, wherein the linker is cleavable or non-cleavable and wherein the linker is coupled to a dye, radioisotope, or cytotoxin.

* * * * *

UNITED STATES PATENT AND TRADEMARK OFFICE
CERTIFICATE OF CORRECTION

PATENT NO. : 11,130,818 B2
APPLICATION NO. : 15/750725
DATED : September 28, 2021
INVENTOR(S) : Birgit Piater et al.

It is certified that error appears in the above-identified patent and that said Letters Patent is hereby corrected as shown below:

In the Claims

At Column 147, Claim 2, Line 49, the text "6-amino" should be changed to -- ε-amino --

At Column 147, Claim 2, Line 51, the text "aminoterminal" should be changed to -- amino-terminal --

Signed and Sealed this
Twenty-first Day of June, 2022

Katherine Kelly Vidal
*Director of the United States Patent and Trademark Office*